(12) United States Patent
Tang et al.

(10) Patent No.: US 8,084,621 B2
(45) Date of Patent: Dec. 27, 2011

(54) 3-PYRROLO[B]CYCLOHEXYLENE-2-DIHYDROINDOLINONE DERIVATIVES AND USES THEREOF

(75) Inventors: Feng Tang, Jiangsu (CN); Han Shen, Jiangsu (CN); Qiu Jin, Jiangsu (CN); Lei Ding, Jiangsu (CN); Jie Yang, Jiangsu (CN); Xiaojin Yin, Jiangsu (CN); Shiyue Lu, Jiangsu (CN)

(73) Assignee: Jiangsu Simcere Pharmaceutical R&D Co. Ltd., Nanjing, Jiangsu (CN)

( * ) Notice: Subject to any disclaimer, the term of this patent is extended or adjusted under 35 U.S.C. 154(b) by 0 days.

(21) Appl. No.: 12/517,351

(22) PCT Filed: Dec. 3, 2007

(86) PCT No.: PCT/CN2007/071161
§ 371 (c)(1),
(2), (4) Date: Jun. 2, 2009

(87) PCT Pub. No.: WO2008/067756
PCT Pub. Date: Jun. 12, 2008

(65) Prior Publication Data
US 2010/0160318 A1    Jun. 24, 2010

(30) Foreign Application Priority Data

Dec. 4, 2006  (CN) .......................... 2006 1 0098202
Dec. 15, 2006 (CN) .......................... 2006 1 0161220

(51) Int. Cl.
*C07D 209/02* (2006.01)
*A61K 31/40* (2006.01)
(52) U.S. Cl. ........................................ 548/455; 514/414
(58) Field of Classification Search .................... 548/516
See application file for complete search history.

(56) References Cited

U.S. PATENT DOCUMENTS
6,642,251 B1   11/2003  Tang et al.

FOREIGN PATENT DOCUMENTS

| WO | WO 00/12084 A1 | 3/2000 |
|---|---|---|
| WO | WO 01/37819 A2 | 5/2001 |
| WO | WO 01/60814 A2 | 8/2001 |
| WO | WO 02/092079 A1 | 11/2002 |
| WO | WO 03/035009 A2 | 5/2003 |
| WO | WO 2005/053686 A1 | 6/2005 |

*Primary Examiner* — Kamal Saeed
*Assistant Examiner* — Nyeemah A Grazier
(74) *Attorney, Agent, or Firm* — Global IP Services; Tianhua Gu

(57) ABSTRACT

3-pyrrolo[b]cyclohexylene-2-dihydro-indolinone derivatives of formula (I) or their pharmaceutically acceptable salts and uses thereof. The intermediates of formula (II) for preparing the above compounds. The bioassay shows that the above compounds and their pharmaceutically acceptable salts can modulate the activity of protein kinases (PKs), inhibit the activity of tyrosine kinases (PTKs) and inhibit many kinds of tumor cells as well as.

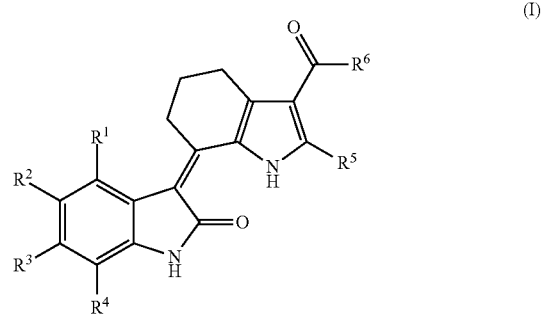

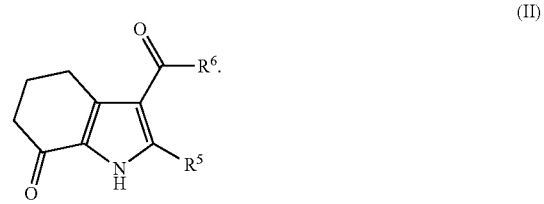

11 Claims, No Drawings

3-PYRROLO[B]CYCLOHEXYLENE-2-DIHYDROINDOLINONE DERIVATIVES AND USES THEREOF

CROSS REFERENCE TO RELATED PATENT APPLICATION

The present patent application is the US national stage of PCT/CN2007/071161 filed on Dec. 3, 2007, which claims the priority of the Chinese patent applications No. 200610098202.X filed on Dec. 4, 2006 and No. 200610161220.8 filed on Dec. 15, 2006 that two Chinese patent applications are incorporated herein by reference.

FIELD OF INVENTION

The present invention relates to 3-pyrrolo[b]cyclohexylene-2-dihydroindolinone derivatives and uses thereof. The present invention also relates to the method for preparing the compounds above and the intermediates thereof.

BACKGROUND OF THE INVENTION

The following is offered as background information only and is not admitted to be prior art to the present invention.

At present, many 2-dihydroindolinone derivatives have been attemped to identify as protein kinase inhibitors, which are widely used in the treatment of a variety of diseases associated with abnormal kinase activity, such as cancer, psoriasis, hepatocirrhosis, diabetes, angiogenesis, ophthalmological disease, rheumatoid arthritis and other inflammatory disorders, immune disease, cardiovascular disease, e.g. atherosclerosis, and a variety of kidney diseases. Of which, many indirubin derivatives (PCT WO2001037819, PCT WO2002092079), 3-methylenepyrrole-2-dihydroindolinone derivatives (U.S. Pat. No. 6,642,251, PCT WO2001060814, PCT WO2003035009, PCT WO2005053686), 3-pyrrolo[b] cyclopentylene-2-dihydroindolinone derivatives (PCT WO2005016875), and other 2-dihydroindolinone derivatives (PCT WO 2000012084) etc, all are described as the kinase inhibitors for treating cancer.

Mammalian cells have similar molecular mechanisms to regulate cell proliferation, differentiation and death in the entire cell cycle. Of these, protein phosphorylation is a major mechanism for transmembrane or intracellular signal transduction, with the function of cell cycle regulation, while phosphorylation is regulated by protein kinases (PKs) and protein phosphatases. Protein kinases are the largest known family of enzymes in humans, with a conserved catalytic domain and various regulation modes. Protein kinases are enzymes catalyzing the transfer of the terminal (γ) phosphoryl group of ATP to specific amino acid residues of substrate. According to the specificity of these amino acid residues, these kinases are divided into 4 types, of which the main two types are serine/threonine kinases (STKs) and protein tyrosine kinases (PTKs). In eukaryotes, there is physical segregation and distance between cell surface receptors and nuclear transcription. Extracellular signals affect the cascades of some protein kinases with multi-step phosphorylation, and finally alter the activity of transcription factors to activate or block gene transcription. Protein tyrosine kinases and protein serine/threonine kinases play an important role in the normal signal transduction process and their aberrant expression will result in a wide array of disorders and diseases such as cancer, arteriosclerosis, psoriasis, inflammatory responses and so on. Thus, it is a novel therapy strategy to regulate kinase activity and restore the physiological balance.

The family of protein tyrosine kinases, consisting of transmembrane receptors (receptor tyrosine kinases, RTKs) and cytoplasmic forms (non-receptor tyrosine kinases, CTKs), are involved in cellular signal transduction. The protein kinase complement of the human genome (kinome) consists of 30 tyrosine kinase families containing about 90 distinct protein tyrosine kinases (PTKs), of which 58 members are receptor tyrosine kinases. For a more complete discussion of tyrosine kinases, see Manning G, Science, 2002, 298:1912 which is incorporated by reference, including any drawings, as if fully set forth herein. Receptor tyrosine kinase is a class of transmembrane protein with cytoplasmic region and an extracellular portion which is composed of a very large protein domain binding to extracellular ligands e.g. a soluble or membrane-bound polypeptide, including insulin and a variety of growth factor. A Cytoplasmic portion contains the tyrosine kinase catalytic domain with autophosphorylation site, whose intrinsic catalytic activity that is activated upon ligand binding. Receptor tyrosine kinases include EGFR (epidermal growth factor receptor), VEGFR (vascular endothelial growth factor receptor), PDGFR (platelet-derived growth factor receptor), FGFR (fibroblast growth factor receptor) and so on. The most important downstream signaling cascades activated by RTKs include the Ras-extracellular ERK/MAPK pathway, the PI-3' kinase-AKT and the JAK/STAT pathway. PTKs provide communication signals that link all these pathways ultimately leading to regulation of gene transcription. Additional cascades may also be utilized. Through a different regulatory mechanism, non-receptor tyrosine kinases (CTKs) participate in response to extracellular signals by physically associating with transmembrane receptors (Grosios k, et al, Drugs Fut, 2003, 28:679).

These phosphorylated tyrosine residues serve as docking sites for phosphotyrosine binding domains (e.g., Src homology 2 and 3 [SH2 and SH3] and phosphotyrosine binding [PT-3] domains) found in a number of intracellular signaling proteins (e.g., Shc, Grb2, Src, Cbl, phospholipase Cg and phoshoinositol-3' [PI-3' kinase]). Assembly of activated complexes at the membrane initiates several cascades which are the key to downstream signaling and biological response. Formation of homo- or heterodimers is also possible. Receptors lacking catalytic activity can be coupled to nonreceptor PTKs via noncovalent association with the cytoplasmic domain of a receptor subunit, thus forming "binary" receptors. The most important downstream signaling cascades activated by RTKs include the Ras-extracellular regulated kinase (ERK)-mitogen activated (MAP) kinase pathway, the PI-3' kinase-AKT and the JAK/STAT pathway. PTKs provide communication signals that link all these pathways ultimately leading to regulation of gene transcription. Additional cascades may also be utilized. For example, the InsR utilizes the adenylyl cyclase signaling system which, in turn, activates cAMP-dependent serine-threonine specific protein kinases. (Grosios k, et al, Drugs Fut, 2003, 28:679)

Non-receptor tyrosine kinases (CTKs) participate in response to extracellular signals by physically associating with transmembrane receptors, such as hormone, cytokine and growth factor receptors. They are then activated when these receptors are bound by extracellular ligands or cell adhesion components at particular phases of the cell cycle.

In normal cells, activated RTKs are rapidly internalized away from the cell surface and are subject to modifications that inhibit their enzymatic activity. This ensures that activation of signal cascades are only transient and the cell returns to its non-stimulated state in a timely fashion. However, a variety of structural alterations ranging from single amino acid substitutions to large deletions, or deregulation of inhibitory signals and autocontrol mechanisms, can lock kinases into the activated form in which the kinase domain is always active. A number of diseases have been shown to be due to mutations that activate or lead to misexpression/overexpression of PTKs. During molecular characterization of malignancies, approximately half of all known PTKs such as EGF, ErbB2, Ret, Kit, Src, Abl, PDGFR, VEGF1/2/3, FGFR1/2/3, etc, have been found in either mutated or overexpressed forms including sporadic cases. Clinical studies also show overexpression or disorders of PTKs is of important reference value for the prognosis of cancer patients and symptoms prediction (Madhusudan S, et al, Clin Biochem, 2004, 37:618). In summary, tyrosine kinases are very important for physiological self-regulation and gene mutation/rearrangemen may lead to the disorder or over-expression of PTKs, then result in the occurrence of diseases, so the agonist or antagonist of PTKs can be used in the treatment.

Irrespective of the underlying genetic alteration, the outcome i.e., altered, aberrant or inappropriate receptor presence, gives rise to respective disease phenotypes (e.g., cancer). This is not however, maintained only by receptor deregulation but also in the context of the whole cell circuit and intra-/intercellular communications, i.e., a multitude of paracrine and autocrine communications. Growth factors (e.g., EGF, VEGF, PDGF) and their receptors are frequently overexpressed in cancers and their coexpression is often associated with tumor cell proliferation and other tumor parameters such as angiogenesis and metastasis.

Angiogenesis is a physiological process involving the growth of new blood vessels from pre-existing vessels. Normal angiogenesis only occurs in some particular short-term physiological processes, such as reproduction and wound healing etc. However aberrant angiogenesis is one of the pathological manifestations of some diseases including malignant tumor, rheumatoid arthritis, diabetic retinopathy and so on. Based on a large number of clinical practice and experiments, Folkman brought forth a hypothesis that tumor growth required angiogenesis: due to the lack of neovascularization, the diameter of tumors in the early stage of formation is limited in 2~3 mm and cells number is less than one million; when entering the angiogenesis stage through the mediation of tumor angiogenesis factor (Tumor-angiogenesis Factor, TAF) secreted by tumor cells, the tumor can grow rapidly with adequate supply of oxygen and nutrients (Folkman J, N Engl J Med, 1971, 285:1182). Thus anti-angiogenesis therapy is a new anti-cancer strategy by blocking TAF.

Tumor cells can secrete a variety of angiogenic factors, which interact with each other. Vascular endothelial growth factor (VEGF) is thereinto the most specific angiogenic factors with highest activity and other angiogenic factors exert angiogenic effect mostly by enhancing the expression of VEGF (Zhang Q X, et al, J Surg Res, 1997, 67:147). VEGF is expressed in the vast majority of tumor cells and a variety of tissues such as lung, spleen, kidney, liver, etc. The expression of VEGF is regulated by many factors, of which hypoxia is by far the strongest induced effect. In addition, the growth factors following such as basic fibroblast growth factor (bFGF), epidermal growth factor (EGF), platelet-derived growth factor (PDGF), keratinocyte growth factor (KGF), placental growth factor (PLGF), transforming growth factor $\beta$ (TGF$\beta$), insulin-like growth factor-1 (IGF-1), tumor necrosis factor $\alpha$ (TNF$\alpha$), interleukin (IL)-1$\beta$, IL-6 and NO can also promote the expression of VEGF. But interferon-$\alpha$ (IFN-$\alpha$), IL-10, IL-12, etc can inhibit the expression of VEGF. Furthermore, oncogene ras, raf, src, anti-oncogene vHL and p53 mutations can increase the expression of VEGF (Neufeld G, et al, FASEB J, 1999, 13:9).

VEGF receptor (VEGFR) are known to have three members: VEGFR-1/Flt-1, VEGFR-2 (Flk-1/KDR) and VEGFR-3/Flt-4, in which VEGFR-1 and VEGFR-2 are expressed specially in vascular endothelial cells and associated with angiogenesis closely. VEGFR, a member of receptor tyrosine kinase family, is a class of transmembrane protein with a cytoplasmic region, and its expression is induced by VEGF. Compared to a low level of expression in normal human tissues, both VEGF and its receptors (VEGFR) show the high expression level in the vast majority of malignant tumors. Furthermore, VEGFR is expressed not only in vascular endothelial cells, but also in tumor cells. So besides paracrine, it indicates the existence of autocrine pathway. As a vascular endothelial cell-specific mitogen, VEGF secreted by the malignant cells acts on VEGF receptor in vascular endothelial cells of adjacent stromal tissue, that promotes vascular endothelial cell division and proliferation, and induces tumor angiogenesis. Moreover, it also increases vascular permeability, promotes tumor growth and metastasis, then acts on tumor cells directly and stimulates tumor cell growth. (Rong L, Foreign Medical Sciences•Section of Pathophysiology and Clinical Medicine, 2002, 22:4475 and references cited)

Mutatioms in PKs and cross-talk in signal proteins are also involved in diseases other than cancer. Mutational inactivation of nonreceptor tyrosine kinase is observed in several immunodeficiencies. Inactivation of both copies of JAK3 causes severe combined immunodeficiency (Leonard W J, Nat Rev Immunol, 2001, 1:200; Leonard W J, Int J Hematol, 2001, 73:271). Mutation in the Bruton tyrosine kinase (BTK, also known as BPK or ATK), a member of the src family and a key regulator of B-cell maturation, causes X-linked Agammaglobulinemia (Cheng G, et al, Proc Natl Acad Sci USA, 1994, 91:8152; Maas A, et al, J Immunol, 1999, 162:6526). The physiological role of PTK in CNS signaling also suggests that deregulation of these proteins might also be involved in related disorders. This is supported by the observation that neuregulin-1 and ErbB4 immunoreactivity is associated with neuritic plaques in the Alzheimer's disease (Ferguson S S, Trends Neurosci, 2003, 26:119; Chaudhury A R, et al, J Neuropathol Exp Neurol, 2003, 62:42). Abnormal regulation of Insulin-like growth factor (IGFs) and its regulatory protein secreted by the cardiovascular system may lead to coronary atherosclerosis and the occurrence and development of restenosis. The role of IGFs is mediated by specific membrane receptors, in which IGF receptor-I shows tyrosine kinase activity and appears in smooth muscle cells, inflammatory cells and arterial endothelial cells in atherosclerotic injury (Bayes-genis A, et al, Circ Res, 2000, 86:125; Bayes-genis A, et al, Artherio Thromb and Vascu Biol, 2001, 21:335; Che W Y, et al, Circ Res, 2002, 90:1222). Vascular endothelial growth factor and its receptors expressed in a variety of rheumatoid arthritis cells are a key factor in the pathological angiogenesis of rheumatoid arthritis (De Bandt M, et al, J Immunol, 2003, 1712:4853). Jak2 is a cytoplasmic, non-receptor tyrosine kinase and its mutation causes at least three diseases, such as polycythemia vera (PV), idiopathic myelofibrosis (IMF), essential thrombocythemia (ET) as well as some other atypical myeloproliferative disorders (MPD). Mutation in the tyrosine kinase domain of fibroblast growth factor receptor would lead to the most common hereditary dwarfism—bone Dyschondroplasia (Shiang R, et al, Cell, 1994, 78: 335).

On the other hand, a number of diseases are due to insufficient PTK signaling, such as non-insulin-dependent diabetes and peripheral neuropathies, and in such cases methods to enhance signaling could serve as viable therapies (Hunter T, Cell, 2000, 100:111). This is also a very attractive possibility for other angiogenesis-related conditions, including certain cardiovascular diseases where stimulation of angiogenesis might be required rather than inhibition.

With the in-depth study on molecular biology, it is an effective way to inhibit tumor cell proliferation and treat cancer by regulating the cellular signal transduction, mediating the function of growth factor and regulating oncogene expression at the molecular level. It is effective to weaken the effect of abnormal signal pathway, inhibit tumor growth and promote tumor cell death. Up to now, more than half of proto-oncogenes encode tyrosine kinase proteins. They participate in cellular signal transduction by phosphorylation and dephosphorylation, while in the process of tumorigenesis, mutation or over-expression of PTK can transform normal cells into cancer cells and promote growth and mitosis of tumor cells.

At the same time, the growth and metastasis of malignant tumors rely on the adequate nutrient supply through the new peripheral blood vessels. The process of tumor angiogenesis can generally be divided into two stages: preangiogenesis period and angiogenesis period. Transformation of these two stages is called as "angiogenic switch". It is a key role in the process of deterioration that tumor cells switch to the angiogenic phenotype. Tumor cells can not get enough nutrients and discharge metabolites without peripheral angiogenesis, and mainly survive on oxygen and nutrients dispersed around cells, thus tumors can not grow beyond 1-2 mm in diameter. Once switch to angiogenic phenotype, tumors without blood vessels can grow rapidly utilizing the nutrients from the blood. Furthermore, these malignant cells can induce phenotypic changes of other cells, such as endothelial cells, then promote the formation of new blood vessels. Angiogenic factors participate in the regulation of angiogenic switch, cause endothelial cell migration, proliferation and morphological change, then initiate the generation of tumor blood vessels. All the known angiogenic factors mainly are the ligands of PTKs, such as VEGF, bFGF, PD-ECGF, etc (Bergers G, et al, Nat Rev Cancer, 2003, 3:401). Therefor it is an effective therapy to prevent the formation of tumor angiogenesis and control the growth of malignant tumors by using the tyrosine kinase inhibitors as anti-angiogenesis substances.

TKs play an important role in carcinogenic transformation of cells and relate to the occurrence and progress of tumors directly or indirectly, so it is especially appropriate for TKs inhibitors used in the treatment of tumors.

The serine/threonine kinases (STKs) are kinases family members that catalyze the phosphorylation of specific serine and threonine residues. STKs, like the non-receptor PTKs, are predominantly intracellular although there are a few receptor kinases of the STK type. STKs are the most common of the cytosolic kinases, i.e., kinases that perform their function in that part of the cytoplasm other than the cytoplasmic organelles and cytoskeleton. STKs affect the internal biochemistry of the cell, often as a down-line response to a PTK event. STKs have been implicated in the signaling process which initiates DNA synthesis and subsequent mitosis leading to cell proliferation. Additionally STKs are associated with many types of cancers, such as breast cancer etc. (Cance et al, Int. J. Cancer, 1993, 55, 571).

PTKs and STKs have all been implicated in a host of pathogenic conditions including, significantly, cancer. Other pathogenic conditions which have been associated with PKs include, without limitation, psoriasis, hepatocirrhosis, diabetes, angiogenesis, restenosis, ophthalmological disease, rheumatoid arthritis and other inflammatory disorders, immune disease, cardiovascular disease, e.g. atherosclerosis, and a variety of kidney diseases.

Presently, many 2-dihydroindolinone derivatives attemped to identify as protein kinase inhibitors, such as indirubin derivatives (PCT WO2001037819, PCT WO2002092079), 3-methylenepyrrole-2-dihydroindolinone derivatives (U.S. Pat. No. 6,642,251, PCT WO2001060814, PCT WO2003035009, PCT WO2005053686), 3-pyrrolo[b]cyclopentylene-2-dihydroindolinone derivatives (PCT WO2005016875), and other 2-dihydroindolinone derivatives (PCT WO 2000012084) etc, all are described as STK or PTK inhibitors for treating cancer.

SUMMARY OF THE INVENTION

The present invention is directed to novel 2-indolinone derivatives which modulate protein kinase activity and inhibit the proliferation of tumor cells. In addition, the present invention relates to the preparation method of disclosed compounds and their intermediates.

The terms "2-indolinone", "indolin-2-one" and "2-oxindole" are used interchangeably herein to refer to a molecule having the chemical structure of Formula (III):

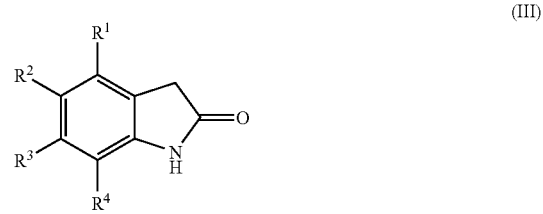

The term "pyrrolo[b]cyclohexylidene" refers to a molecule having the chemical structure:

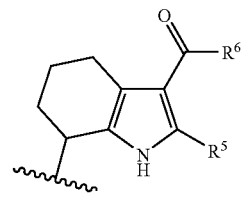

The term "3-pyrrolo[b]cyclohexylidene-2-indolinone" refers to a molecule having the chemical structure of Formula (I).

The term "pyrrolo[b]cyclohexanone" refers to a molecule having the chemical structure of Formula (II).

A "pharmaceutically acceptable salt" refers to those salts which retain the biological effectiveness and properties of the parent compound. Such salts include:

(1) Acid addition salt which is obtained by reaction of the free base of the parent compound with inorganic acids or organic acids. Inorganic acids include, but not limited to, hydrochloric acid, hydrobromic acid, nitric acid, phosphoric acid, metaphosphoric acid, sulfuric acid, sulfite acid and perchloric acid and the like. Organic acids include, but not limited to, acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, 1-naphthalenesulfonic acid, 2-naphthalenesulfonic acid, p-toluenesulfonic acid, salicylic acid, tartaric acid, citric acid, lactic acid, mandelic acid, succinic acid or malonic acid and the like.

(2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

1. Chemistry
A. General Structural Features

In one aspect, the present invention relates to the compounds having the chemical structure of Formula (I):

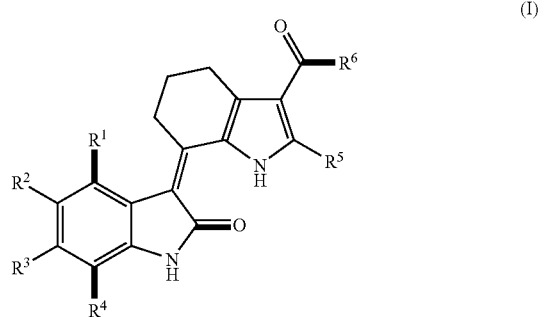

(I)

wherein:
$R^1$ is selected from the group consisting of hydrogen, halo, alkyl, cycloalkyl, aryl, heteroaryl, heteroalicyclic, hydroxy, alkoxy, —C(O)$R^7$, —N$R^8R^9$, —(CH$_2$)$_n R^{10}$ and —C(O)N$R^{11}R^{12}$;
$R^2$ is selected from the group consisting of hydrogen, halo, alkyl, haloalkyl, hydroxy, alkoxy, haloalkoxy, nitro, cyano, —N$R^8R^9$, —N$R^8$C(O)$R^9$, —C(O)$R^7$, aryl, heteroaryl, —C(O)N$R^{11}R^{12}$, —S(O)$_2$N$R^8R^9$ and —SO$_2R^{13}$;
$R^3$ is selected from the group consisting of hydrogen, halo, alkyl, haloalkyl, hydroxy, alkoxy, —C(O)$R^7$, —N$R^8R^9$, aryl, heteroaryl, —N$R^8$S(O)$_2R^9$, —S(O)$_2$N$R^8R^9$, —N$R^8$C(O)$R^9$, —N$R^8$C(O)O$R^9$ and —SO$_2R^{13}$;
$R^4$ is selected from the group consisting of hydrogen, halo, alkyl, hydroxy, alkoxy and —N$R^8R^9$;
$R^5$ is selected from the group consisting of hydrogen, alkyl and —C(O)$R^{14}$;
$R^6$ is selected from the group consisting of hydroxy, alkoxy, aryloxy, —N($R^{15}$)(CH$_2$)$_r R^{16}$, —N$R^8R^9$ and —N($R^{17}$)—CH($R^{18}$)—C$R^{19}$(OH)—CH($R^{20}$)Z;
$R^7$ is selected from the group consisting of hydrogen, hydroxy, alkoxy and aryloxy;
$R^8$ and $R^9$ are each independently selected from the group consisting of hydrogen, alkyl, cycloalkyl, aryl and heteroaryl; or $R^8$ and $R^9$ together with the atoms to which they are attached may form a heteroalicyclic ring;
$R^{10}$ is selected from the group consisting of hydroxy, —C(O)$R^7$, —N$R^8R^9$ and —C(O)N$R^8R^9$;
$R^{11}$ and $R^{12}$ are each independently selected from the group consisting of hydrogen, alkyl and aryl;
or $R^{11}$ and $R^{12}$ together with the nitrogen atom to which they are attached may form a heteroalicyclic ring;
$R^{13}$ is selected from the group consisting of alkyl, aryl, arylalkyl, heteroaryl and heteroarylalkyl;
$R^{14}$ is selected from the group consisting of hydroxy, alkoxy, aryloxy and —N$R^8R^9$;
$R^{15}$ is selected from the group consisting of hydrogen and alkyl;
$R^{16}$ is selected from the group consisting of hydroxy, —N$R^8R^9$, —C(O)$R^7$, aryl, heteroaryl, —N$^+$(O$^-$)$R^8R^9$, —N(OH)$R^8$ and —NHC(O)$R^a$, wherein $R^a$ is selected from the group consisting of unsubstituted alkyl, haloalkyl and arylalkyl;
$R^{17}$, $R^{18}$, $R^{19}$ and $R^{20}$ are each independently selected from the group consisting of hydrogen and alkyl;
Z is selected from the group consisting of aryl, heteroaryl and —N$R^8R^9$;
n and r are each independently an integer from 1 to 4.

Unless otherwise indicated, the following terms used in the specification and claims have the meanings discussed below:

As used herein, the term "alkyl" refers to a saturated aliphatic hydrocarbon including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). A lower alkyl is a alkyl having 1 to 4 carbon atoms. An unsubstituted lower alkyl is a lower alkyl without a substituent except hydrogen atoms. More preferably, it is a medium size alkyl having 1 to 10 carbon atoms e.g., methyl, ethyl, propyl, 2-propyl, n-butyl, iso-butyl, tert-butyl, pentyl, and the like. Most preferably, it is a lower alkyl having 1 to 4 carbon atoms e.g., methyl, ethyl, propyl, 2-propyl, n-butyl, iso-butyl, tert-butyl, and the like. Alkyl may be substituted or unsubstituted.

When substituted, the substituted group(s) is preferably one or more, more preferably one, two or three, most preferably one or two. The substituent group is individually selected from halo, hydroxy, lower alkoxy, aryl, aryloxy, heteroaryl, heteroalicyclic, —C(O)$R^7$, —N$R^8R^9$ and —C(O)N$R^{11}R^{12}$, with $R^7$, $R^8$, $R^9$, $R^{11}$ and $R^{12}$ as defined above.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and cycloheptatriene. A cycloalkyl group may be substituted or unsubstituted. When substituted, the substituent group(s) is preferably one or more individually selected from alkyl, aryl, heteroaryl, heteroalycyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —N$R^8R^9$, with $R^8$ and $R^9$ as defined above.

An "aryl" group refers to an all-carbon monocyclic or fused-ring polycyclic groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^8S(O)-$, $R^8S(O)_2-$, $-C(O)OR^8$, $R^8C(O)O-$, and $-NR^8R^9$, with $R^8$ and $R^9$ as defined above. Preferably, the aryl group is optionally substituted with one or two substituents independently selected from halo, lower alkyl, trihaloalkyl, hydroxy, mercapto, cyano, N-amido, mono or dialkylamino, carboxy, or N-sulfonamido.

"Heteroaryl" refers to a monocyclic or fused ring group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. When substituted, the substituted group(s) is preferably one or more, more preferably one, two, or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^8S(O)-$, $R^8S(O)_2-$, $-C(O)OR^8$, $R^8C(O)O-$, and $-NR^8R^9$, with $R^8$ and $R^9$ as defined above. Preferably, the heteroaryl group is optionally substituted with one or two substituents independently selected from halo, lower alkyl, trihaloalkyl, hydroxy, mercapto, cyano, N-amido, mono or dialkylamino, carboxy, or N-sulfonamido.

"Heteroalicyclic" refers to a monocyclic or fused ring group having in the ring(s) of 5 to 9 ring atoms in which one or two ring atoms are heteroatoms selected from N, O, or S(O)n (where n is an integer from 0 to 2), the remaining ring atoms being C. The rings may also have one or more double bonds. However, the rings do not have a completely conjugated pi-electron system. Examples, without limitation, of unsubstituted heteroalicyclic groups are pyrrolidino, piperidino, piperazino, morpholino, thiomorpholino, and the like. The heteroalicyclic ring may be substituted or unsubstituted. When substituted, the substituted group(s) is preferably one or more, more preferably one, two or three, even more preferably one or two, independently selected from the group consisting of lower alkyl, trihaloalkyl, halo, hydroxy, lower alkoxy, mercapto, (lower alkyl)thio, cyano, acyl, thioacyl, O-carbamyl, N-caxbamyl, O-thiocarbamyl, N-thiocarbamyl, C-amido, N-amido, nitro, N-sulfonamido, S-sulfonamido, $R^8S(O)-$, $R^8S(O)_2-$, $-C(O)OR^8$, $R^8C(O)O-$, and $-NR^8R^9$, with $R^8$ and $R^9$ as defined above. Preferably, the heteroalicyclic group is optionally substituted with one or two substituents independently selected from halo, lower alkyl, trihaloalkyl, hydroxy, mercapto, cyano, N-amido, mono or dialkylamino, carboxy, or N-sulfonamido.

"Heterocycle" means a saturated cyclic radical of 3 to 8 ring atoms in which one or two ring atoms are heteroatoms selected from N, O, or S(O)n (where n is an integer from 0 to 2), the remaining ring atoms being C, where one or two C atoms may optionally be replaced by a carbonyl group. The heterocyclyl ring may be optionally substituted independently with one, two, or three substituents selected from lower alkyl, optionally substituted one or two substituents independently selected from carboxy or ester group, haloalkyl, halo, nitro, cyano, hydroxy, alkoxy, amino, monoalkylamino, dialkylamino, aralkyl, heteroaralkyl, —C(O)R (where R is alkyl), and —(CH$_2$)nY (where Y is heteroalicyclic or $R^{10}$, with $R^{10}$ as defined above, and n is an integer from 0 to 2). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, tetrahydropyrimidin-2-one, and the derivatives thereof. Preferably, the heterocycle group is optionally substituted with one or two substituents independently selected from halo, lower alkyl, lower alkyl substituted with hydroxy, carboxy, or ester, lower alkyl substituted with heteroalicyclic group, hydroxy, mono or dialkylamino and heteroalicyclic group. Examples, without limitation, heteroalicyclic group is selected from the pyrrolidino, piperidino, piperazino, and the like.

"Hydroxy" refers to an —OH group.

"Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Mercapto" refers to an —SH group.

"Acyl" refers to a —C(O)—R' group, where R' is selected from the group consisting of hydrogen, unsubstituted lower alkyl, trihalomethyl, unsubstituted cycloalkyl, aryl optionally substituted with one or more, preferably one, two, or three substituents selected from the group consisting of unsubstituted lower alkyl, trihalomethyl, unsubstituted lower alkoxy, halo and —NR$^8$R$^9$ groups, heteroaryl (bonded through a ring carbon) optionally substituted with one or more, preferably one, two, or three substitutents selected from the group consisting of unsubstituted lower alkyl, trihalomethyl, unsubstituted lower alkoxy, halo and —NR$^8$R$^9$ groups and heteroalicyclic (bonded through a ring carbon) optionally substituted with one or more, preferably one, two, or three substituents selected from the group consisting of unsubstituted lower alkyl, trihalomethyl, unsubstituted lower alkoxy, halo and —NR$^8$R$^9$ groups with R$^8$ and R$^9$ as defined above. Representative acyl groups include, but are not limited to, acetyl, trifluoroacetyl, benzoyl, and the like.

"Thioacyl" refers to a —C(S)—R' group, with R' as defined above.

"Ester" refers to a —C(O)O—R' group with R' as defined above except that R' cannot be hydrogen.

"Acetyl" group refers to a —C(O)CH$_3$ group.

"Halo" group refers to fluorine, chlorine, bromine or iodine, preferably fluorine, chlorine or bromine.

"Trihalomethyl" group refers to a —CX$_3$ group wherein X is a halo as defined above.

"Cyano" refers to a —CN group.

"S-sulfonamido" refers to a —S(O)$_2$NR$^8$R$^9$ group, with R$^8$ and R$^9$ as defined above.

"N-sulfonamido" refers to a —NR$^8$S(O)$_2$R$^9$ group, with R$^8$ and R$^9$ as defined above.

"O-carbamyl" refers to a —OC(O)NR$^{11}$R$^{12}$ group, with R$^{11}$ and R$^{12}$ as defined above.

"N-carbarmyl" refers to a R⁸OC(O)NR⁹— group, with R⁸ and R⁹ as defined above.

"O-thiocarbamyl" refers to a —OC(S)NR¹¹R¹² group, with R¹¹ and R¹² as defined above.

"N-thiocarbarmyl" refers to a R⁸OC(S)NR⁹— group, with R⁸ and R⁹ as defined above.

"Amino" refers to a —NH₂ group.

"C-amido" refers to a —C(O)NR⁸R⁹ group, with R⁸ and R⁹ as defined above.

"N-amido" refers to a R⁸C(O)NR⁹— group, with R⁸ and R⁹ as defined above.

"Nitro" refers to a —NO₂ group.

"Haloalkyl" means an alkyl, preferably lower alkyl as defined above that is substituted with one or more same or different halo atoms, e.g., —CH₂Cl, —CF₃, —CH₂CF₃, —CH₂CCl₃, and the like.

"Haloalkoxy" means an alkoxy, preferably —O-alkyl as defined above wherein alkyl is substituted with one or more same or different halo atoms. Preferably trihalomethoxy is selected, e.g., —OCF₃.

"Aralkyl" means alkyl, preferably lower alkyl as defined above which is substituted with an aryl group as defined above, e.g., —CH₂phenyl, —(CH₂)₂phenyl, —(CH₂)₃phenyl, CH₃CH(CH₃)CH₂phenyl, and the like, and derivatives thereof.

"Heteroaralkyl" group means alkyl, preferably lower alkyl as defined above which is substituted with a heteroaryl group, e.g., —CH₂pyridinyl, —(CH₂)₂pyrimidinyl, —(CH₂)₃imidazolyl, and the like, and derivatives thereof.

"Monoalkylamino" means a radical —NHR where R is an alkyl or unsubstituted cycloalkyl group as defined above, e.g., methylamino, (1-methylethyl)amino, cyclohexylamino, and the like.

"Dialkylamino" means a radical —NRR where each R is independently an alkyl or unsubstituted cycloalkyl group as defined above, e.g., dimethylamino, diethylamino, N-methylcyclohexylamino, and the like.

A "piperazinyl" group refers to a group having the chemical structure:

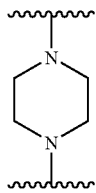

A "morpholinol" group refers to a group having the chemical structure:

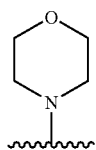

A "piperidino" group refers to a group having the chemical structure:

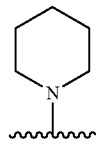

A "pyrrolidino" group refers to a group having the chemical structure:

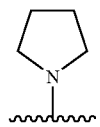

"Optional" or "optionally" means that the subsequently described event or circumstance may but need not occur, and that the description includes instances where the event or circumstance occurs and instances in which it does not. For example, "heteroaryl group optionally substituted with one or two substituents" means that the substituent of heteroaryl may but need not be one, and the description includes situations where the heteroaryl group is substituted with one substituent and situations where the heteroaryl group is substituted with two substituents.

B. Preferred Structural Features.

In one aspect, the present invention relates to the preferred compounds having the chemical structure of Formula (I). wherein:

$R^1$ is selected from the group consisting of hydrogen, halo, alkyl, cycloalkyl, aryl, heteroaryl, heteroalicyclic, hydroxy, alkoxy, —C(O)R⁷, —NR⁸R⁹, —(CH₂)ₙR¹⁰ and —C(O)NR¹¹R¹²;

$R^2$ is selected from the group consisting of hydrogen, halo, alkyl, trihalomethyl, hydroxy, alkoxy, trihalomethoxy, nitro, cyano, —NR⁸R⁹, —NR⁸C(O)R⁹, —C(O)R⁷, aryl, heteroaryl, —C(O)NR¹¹R¹², —S(O)₂NR⁸R⁹ and —SO₂R¹³;

$R^3$ is selected from the group consisting of hydrogen, halo, alkyl, trihalomethyl, hydroxy, alkoxy, —C(O)R⁷, —NR⁸R⁹, aryl, heteroaryl, —NR⁸S(O)₂R⁹, —S(O)₂NR⁸R⁹, —NR⁸C(O)R⁹, —NR⁸C(O)OR⁹ and —SO₂R¹³;

$R^4$ is selected from the group consisting of hydrogen, halo, alkyl, hydroxy, alkoxy and —NR⁸R⁹;

$R^5$ is selected from the group consisting of hydrogen, alkyl and —C(O)R¹⁴;

$R^6$ is selected from the group consisting of hydroxy, alkoxy, —NR⁸R⁹, —N(R¹⁵)(CH₂)ᵣR¹⁶ and —NHCH(R¹⁸)—CR¹⁹(OH)—CH(R²⁰)Z;

$R^7$ is selected from the group consisting of hydrogen, hydroxy, alkoxy and aryloxy;

$R^8$ and $R^9$ are each independently selected from the group consisting of hydrogen, alkyl, cycloalkyl, aryl and heteroaryl; or $R^8$ and $R^9$ together with the atoms to which they are attached may form a heteroalicyclic ring;

$R^{10}$ is selected from the group consisting of hydroxy, —C(O)R⁷, —NR⁸R⁹ and —C(O)NR⁸R⁹;

$R^{11}$ and $R^{12}$ are each independently selected from the group consisting of hydrogen, alkyl and aryl;

or $R^{11}$ and $R^{12}$ together with the nitrogen atom to which they are attached may form a heteroalicyclic ring;

$R^{13}$ is selected from the group consisting of alkyl, aryl, arylalkyl, heteroaryl and heteroarylalkyl;

$R^{14}$ is selected from the group consisting of hydroxy, alkoxy, aryloxy and —$NR^8R^9$;

$R^{15}$ is selected from the group consisting of hydrogen and alkyl;

$R^{16}$ is selected from the group consisting of hydroxy, aryl, heteroaryl and —$NR^8R^9$;

$R^{18}$, $R^{19}$ and $R^{20}$ are each independently selected from the group consisting of hydrogen and alkyl;

Z is selected from the group consisting of aryl, heteroaryl and —$NR^8R^9$;

n is an integer from 1 to 4;

r is an integer from 1 to 3.

C. Most Preferred Structural Features.

In one aspect, the present invention relates to the most preferred compounds having the chemical structure of Formula (I).

It is a presently preferred feature of this invention that $R^1$, $R^3$ and $R^4$ are each preferably independently selected from the group consisting of hydrogen, halo and alkyl.

It is also a presently preferred feature of this invention that $R^2$ is preferably selected from the group consisting of hydrogen, halo, alkyl, alkoxy, trihalomethoxy, nitro, —$NR^8C(O)R^9$, —$C(O)R^7$, —$S(O)_2NR^8R^9$ and —$C(O)NR^{11}R^{12}$, wherein $R^7$ is preferably selected from the group consisting of hydroxy, alkoxy and aryloxy, and $R^{11}$ and $R^{12}$ are each preferably independently selected from the group consisting of hydrogen, alkyl and aryl, or $R^{11}$ and $R^{12}$ together with the nitrogen atom to which they are attached may form a heteroalicyclic ring.

It is an another presently preferred feature of this invention that $R^5$ is methyl;

In yet another presently preferred feature of this invention, $R^6$ is preferably selected from the group consisting of hydroxy, —$NR^8R^9$, —$N(R^{15})(CH_2)_rR^{16}$ and —$NHCH_2CH(OH)CH_2$—$NR^8R^9$, wherein r is an integer from 1 to 3, $R^{15}$ is preferably selected from the group consisting of hydrogen and alkyl, $R^8$ and $R^9$ are each preferably independently selected from the group consisting of hydrogen, alkyl, cycloalkyl, aryl and heteroaryl, or $R^8$ and $R^9$ together with the atoms to which they are attached may form a heteroalicyclic ring, and $R^{16}$ is preferably selected from the group consisting of hydroxy, aryl, heteroaryl and —$NR^8R^9$. Wherein, —$NR^8R^9$ is preferably selected from the group consisting of —$N(CH_3)_2$, —$N(CH_2CH_3)_2$, morpholino, piperazino, piperidino, pyrrolidino, N-methylpiperazino, N-methylcyclohexylamino, 1,4'-dipiperidin-1'-yl, 2-(pyrrolin-1-methyl)-pyrrolin-1-yl, 4-(2-hydroxyethyl)-piperazin-1-yl, and the like.

2. Synthesis and Combinatorial Libraries

A. Combinatorial Libraries

An additional aspect of this invention is a combinatorial library of the compounds having the chemical structure of Formula (I) that can be formed by reacting 2-indolinones of Formula (III) with pyrrolo[b]cyclohexanones of Formula (II).

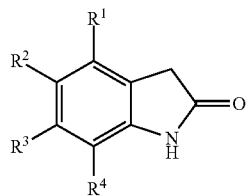

(III)

(II)

wherein $R^1$-$R^6$ have the meanings set forth in general structural features of (A).

As used herein, a "combinatorial library" refers to all the compounds formed by the reaction of each compound of one dimension with a compound in each of the other dimensions in a multi-dimensional array of compounds. In the context of the present invention, the array is two dimensional and one dimension represents all the 2-indolinones of the invention and the second dimension represents all the pyrrolo[b]cyclohexanones of the invention. Each 2-indolinone may be reacted with each and every pyrrolo[b]cyclohexanone in order to form a 3-pyrrolo[b]cyclohexylidene-2-indolinone compound having the chemical structure of Formula (I). All 3-pyrrolo[b]cyclohexylidene-2-indolinone compounds formed in this way are within the scope of the present invention. Also within the scope of the present invention are smaller combinatorial libraries formed by the reaction of some of the 2-indolinones with all of the pyrrolo[b]cyclohexanones, all of the 2-indolinones with some of the pyrrolo[b]cyclohexanones, or some of the 2-indolinones with some of the pyrrolo[b]cyclohexanones.

The 2-indolinone in the above combinatorial library is preferably selected from the group consisting of 2-indolinone itself and substituted 2-indolinones such as, without limitation, 5-fluoroindolin-2-one, 5-chloroindolin-2-one, 5-bromoindolin-2-one, 5-hydroxy-2-one, 5-methylindolin-2-one, 5-ethylindolin-2-one, 5-(n-butyl)indolin-2-one, 5-methoxyindolin-2-one, 5-trifluoromethoxyindolin-2-one, 5-ethoxyindolin-2-one, 5-nitroindolin-2-one, 5-aminoindolin-2-one, 5-acetylindolin-2-one, 5-(N-acetamido)indolin-2-one, 5-(4-fluorophenyl)aminosulfonylindolin-2-one, 5-aminosulfonylindolin-2-one, 5-isopropylaminosulfonylindolin-2-one, 5-dimethylaminosulfonylindolin-2-one, 5-trifluoromethylindolin-2-one, indolin-2-one-5-carboxy, methyl indolin-2-one-5-carboxylate, 6-fluoroindolin-2-one, 7-fluoroindolin-2-one, 6-methoxyindolin-2-one, 6-methylindolin-2-one, 6-chloroindolin-2-one, 4-fluoroindolin-2-one, 4-methylindolin-2-one, 4-methyl-5-chloroindolin-2-one, 5,7-dimethylindolin-2-one.

The pyrrolo[b]cyclohexanone in the above combinatorial library is preferably selected from the group consisting of, without limitation, 2-methyl-7-oxo-4,5,6,7-tetrahydro-1H-indole-3-carboxylic acid, ethyl 2-methyl-7-oxo-4,5,6,7-tetrahydro-1H-indole-3-carboxylate, N-(2-(diethylamino)ethyl)-2-methyl-7-oxo-4,5,6,7-tetrahydro-1H-indole-3-carboxamide, N-(2-(dimethylamino)ethyl)-2-methyl-7-oxo-4,5,6,7-tetrahydro-1H-indole-3-carboxamide, N-(2-hydroxyethyl)-2-methyl-7-oxo-4,5,6,7-tetrahydro-1H-indole-3-carboxamide, 2-methyl-3-(4-methylpiperazine-1-carbonyl)-7-oxo-4,5,6,7-tetrahydro-1H-indole, 2-methyl-3-(morpholine-4-carbonyl)-7-oxo-4,5,6,7-tetrahydro-1H-indole, 2-methyl-7-oxo-N-(2-(piperidin-1-yl)ethyl)-4,5,6,7-tetrahydro-1H-indole-3-carboxamide, 2-methyl-7-oxo-N-(2-(pyrrolidin-1-yl)ethyl)-4,5,6,7-tetrahydro-1H-indole-3-carboxamide, 2-methyl-N-(2-morpholinoethyl)-7-oxo-4,5,6,7-tetrahydro-1H-indole-3-carboxamide, 2-methyl-N-(2-(4- methylpiperazin-1-yl)ethyl)-7-oxo-4,5,6,7-tetrahydro-1H-indole-3-carboxamide, N-(3-(dimethylamino)propyl)-2-methyl-7-oxo-4,5,6,7-tetrahydro-1H-indole-3-carboxamide, 2-methyl-7-oxo-N-(3-(pyrrolidin-1-yl)propyl)-4,5,6,7-tetrahydro-1-indole-3-carboxamide, 2-methyl-7-oxo-N-(3-(piperidin-1-yl)propyl)-4,5,6,7-tetrahydro-1H-indole-3-carboxamide, 2-methyl-N-(3-morpholinopropyl)-7-oxo-4,5,6,7-tetrahydro-1H-indole-3-carboxamide, 2-methyl-N-(3-(4-methylpiperazin-1-yl)propyl)-7-oxo-4,5,6,7-tetrahydro-1H-indole-3-carboxamide, N-(3-(diethylamino)propyl)-2-methyl-7-oxo-4,5,6,7-tetrahydro-1H-indole-3-carboxamide, N-(3-(diethylamino)-2-hydroxypropyl)-2-methyl-7-oxo-4,5,6,7-tetrahydro-1H-indole-3-carboxamide, N-(3-(dimethylamino)-2-hydroxypropyl)-2-methyl-7-oxo-4,5,6,7-tetrahydro-1H-indole-3-carboxamide, N-(2-hydroxy-3-morpholinopropyl)-2-methyl-7-oxo-4,5,6,7-tetrahydro-1H-indole-3-carboxamide, N-(2-hydroxy-3-(pyrrolidin-1-yl)propyl)-2-methyl-7-oxo-4,5,6,7-tetrahydro-1H-indole-3-carboxamide, N-(2-hydroxy-3-(piperidin-1-yl)propyl)-2-methyl-7-oxo-4,5,6,7-tetrahydro-1H-indole-3-carboxamide, N-(2-hydroxy-3-(4-methylpiperazin-1-yl)propyl)-2-methyl-7-oxo-4,5,6,7-tetrahydro-1H-indole-3-carboxamide, N-(3-(cyclohexyl(methyl)amino)-2-hydroxypropyl)-2-methyl-7-oxo-4,5,6,7-tetrahydro-1H-indole-3-carboxamide, N-(2-(dimethylamino)ethyl)-N,2-dimethyl-7-oxo-4,5,6,7-tetrahydro-1H-indole-3-carboxamide, 2-methyl-3-(1,4'-bipiperidin-1'-carbonyl)-7-oxo-4,5,6,7-tetrahydro-1H-indole, 2-methyl-3-[4-(2-hydroxyethyl)-piperazin-1-carbonyl]-7-oxo-4,5,6,7-tetrahydro-1H-indole, 2-methyl-3-[(S)-2-(pyrrolidin-1-ylmethyl)pyrrolidin-1-carbonyl)]-7-oxo-4,5,6,7-tetrahydro-1H-indole, N-(2-(pyridin-2-yl)ethyl)-2-methyl-7-oxo-4,5,6,7-tetrahydro-1H-indole-3-carboxamide.

B. General synthetic Method (1) An Intermediate of Formula (II)

In one more aspect, the present invention relates to pyrrolo[b]cyclohexanone, the intermediate of Formula (II), which is synthesized by the route outlined below: 6-amino-5-oxohexanoic acid hydrochloride(S1) and ethyl acetoacetate were refluxed in a.q. sodium dihydrogen phosphate to generate substituted pyrrole(S2). Then the compound S2 was solved in polyphosphoric acid (PPA), $P_2O_5$ used as dehydrant, reacted to generate ethyl 2-methyl-7-oxo-4,5,6,7-tetrahydro-1H-indole-3-carboxylate (S3) at 70° C. 2-methyl-7-oxo-4,5,6,7-tetrahydro-1H-indole-3-carboxylic acid (S4) is obtained by the hydrolysis of (S3) in 1 mol/L a.q. LiOH. Finally, S4 is reacted with H—$R^6$ at room temperature for 24 hours in DMF to give pyrrolo[b]cyclohexanone of Formula (II) by using a condensation reagent.

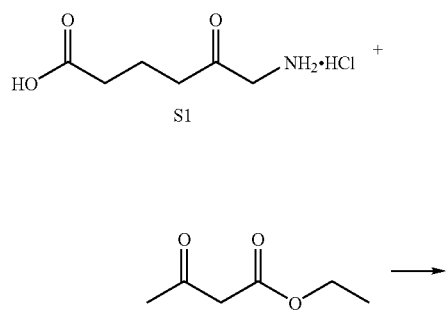

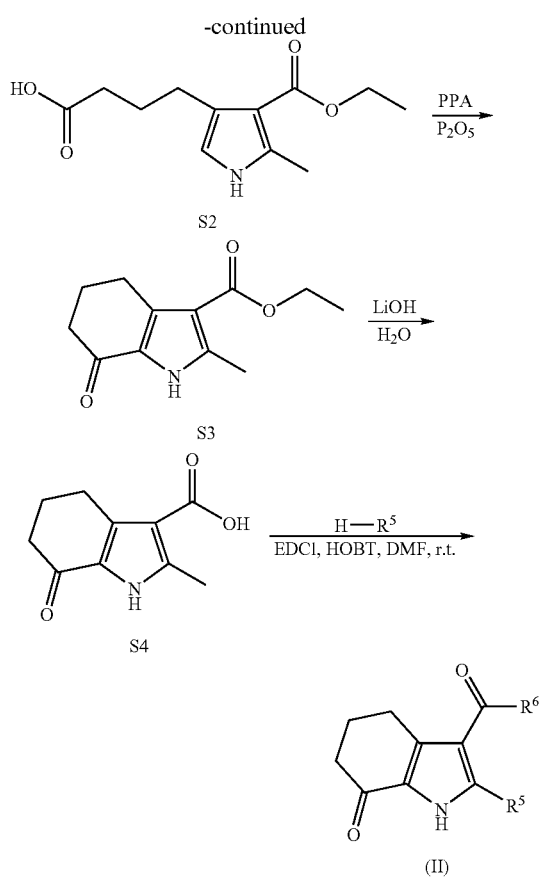

The present invention relates to the intermediates having the chemical structure of Formula (II), Wherein:

$R^5$ is selected from the group consisting of hydrogen, alkyl and —C(O)$R^{14}$;

$R^6$ is selected from the group consisting of hydroxy, alkoxy, —N($R^{15}$)(CH$_2$)$_r R^{16}$, —N$R^8 R^9$ and —NHCH($R^{18}$)—C$R^{19}$(OH)—CH($R^{20}$)Z;

$R^8$ and $R^9$ are each independently selected from the group consisting of hydrogen, alkyl, cycloalkyl, aryl and heteroaryl; or $R^8$ and $R^9$ together with the atoms to which they are attached may form a heteroalicyclic ring;

$R^{14}$ is selected from the group consisting of hydroxy, alkoxy, aryloxy and —N$R^8 R^9$;

$R^{15}$ is selected from the group consisting of hydrogen and alkyl;

$R^{16}$ is selected from the group consisting of hydroxy, —N$R^8 R^9$ and heteroaryl;

$R^{18}$, $R^{19}$ and $R^{20}$ are each independently selected from the group consisting of hydrogen and alkyl;

Z is selected from the group consisting of aryl, heteroaryl and —N$R^8 R^9$;

r is an integer 2 or 3.

The present invention relates to the preferred intermediates, wherein:

$R^5$ is methyl;

$R^6$ is selected from the group consisting of —N($R^{15}$)(CH$_2$)$_r R^{16}$, —N$R^8 R^9$ and —NHCH$_2$CH(OH)CH$_2$—N$R^8 R^9$, or $R^6$ is ethoxy (S3), or $R^6$ is hydroxy (S4);

$R^8$ and $R^9$ are each independently selected from the group consisting of hydrogen, alkyl, cycloalkyl, aryl and heteroaryl; or $R^8$ and $R^9$ together with the atoms to which they are attached may form a heteroalicyclic ring;

R[15] is hydrogen or alkyl;
R[16] is selected from the group consisting of hydroxy, —NR[8]R[9] and heteroaryl;
r is 2 or 3.

Condensation reagents include, but are not limited to, N,N'-Dicyclohexylcarbodiimide(DCC), N,N'-Dissopropyl-carbodiimide(DIC), 1-(3-Dimethylaminopropyl)-3-ethylcarbodiimide hydrochloride(EDCI), 2-Chloro-4,6-dimethoxy-1,3,5-triazine(CDMT), 2,4-Dichloro-6-methoxy-1,3,5-triazine(DCMT), 1,1'-Carbonyldiimidazole(CDI) and 1-Hydroxybenzotriazole(HOBt). Preferably they are EDCI and HOBt.

The reaction described above is carried out at room temperature. The temperature is preferably from 20 to 25° C.

(2) A Compound of Formula (I)

In one aspect of the present invention, provided is method (A) for the synthesis of 3-pyrrolo[b]cyclohexylidene-2-indolinone of Formula (I). As method described above, 2-indolinones of Formula (III) and pyrrolo[b]cyclohexanones of Formula (II) are reacted in the solvent by using a catalyst, wherein the substitutents are described above in the part of "A. General Structural Features". Preferably, R[1], R[3] and R[4] are each preferably independently selected from the group consisting of hydrogen, halo and alkyl;
R[2] is selected from the group consisting of hydrogen, halo, alkyl, alkoxy, trihalomethoxy, nitro, —NR[8]C(O)R[9], —C(O)R[7], —S(O)$_2$NR[8]R[9] and —C(O)NR[11]R[12];
R[5] is methyl;
R[6] is selected from the group consisting of hydroxy, alkoxy, —NR[8]R[9], —N(R[15])(CH$_2$)$_r$R[16] and —NHCH$_2$CH(OH)CH$_2$—NR[8]R[9];
R[7] is selected from the group consisting of hydroxy, alkoxy and aryloxy;
R[8] and R[9] are each independently selected from the group consisting of hydrogen, alkyl, cycloalkyl, aryl and heteroaryl; or R[8] and R[9] together with the atoms to which they are attached may form a heteroalicyclic ring;
R[11] and R[12] are each independently selected from the group consisting of hydrogen, alkyl and aryl;
or R[11] and R[12] together with the nitrogen atom to which they are attached may form a heteroalicyclic ring;
R[15] is hydrogen or alkyl;
R[16] is selected from the group consisting of hydroxy, aryl, heteroaryl and —NR[8]R[9];
r is an integer from 1 to 3.

Method (A)

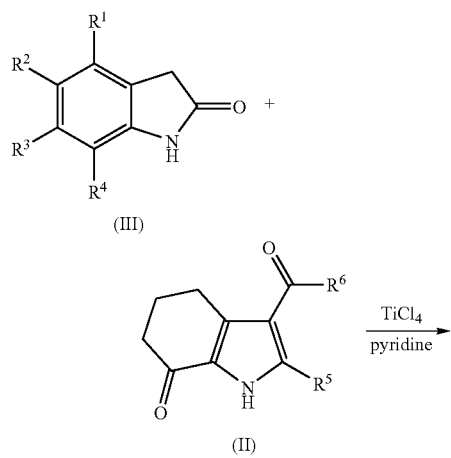

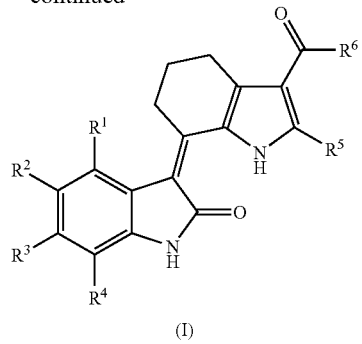

The reaction may be carried out under catalyst, wherein the catalyst is Lewis acid, including but not limited to AlCl$_3$, BF$_3$, SnCl$_4$, SnCl$_2$, ZnCl$_2$, TiCl$_4$. In a presently preferred embodiment of this invention, Lewis acid described above is preferably TiCl$_4$.

The solvent in which the reaction is carried out is an aprotic solvent. An "aprotic solvent" is a solvent that does not exchange protons, which may be divided into non-proton protophilic solvent and inert solvent. It is the feature of a "non-proton protophilic solvent" that is non-acid compared with water, does not have amphiprotic property and contain any active proton, in addition that has a weak tendency to accept proton and is capable of hydrogen bonding in varying degrees. Examples, without limitation, of non-proton protophilic solvents are amides, ketones, nitriles, DMSO and pyridine. An "inert solvent" does not have acid or basic property, and shows a very weak acid-base property, in addition proton transfer process can not occur and the solvent molecules don't participate in reaction. Examples, without limitation, of inert solvent are pentane, hexane, cyclohexane, benzene and toluene.

In a presently preferred embodiment of this invention, the solvent is a non-proton solvent, preferably pyridine.

The reaction is carried out at temperatures greater than room temperature. The temperature is generally from 50° C. to 150° C., preferably 85° C. to 120° C., most preferably 100° C. to 110° C.

The time of reaction carried out herein is 1-20 hours, preferably 5-13 hours, most preferably 8-10 hours.

In another aspect of the present invention, provided is method (B) for the synthesis of 3-pyrrolo[b]cyclohexylidene-2-indolinone of Formula (I). According to the reaction conditions of method (A) described above, 2-indolinones of Formula (III) and 2-methyl-7-oxo-4,5,6,7-tetrahydro-1H-indole-3-carboxylic acid (S4) are reacted to give the compounds of Formula (IV). Then S4 and H—R[6] are treated together in the solvent DMF for 24 hours at room temperature by using a catalyst, wherein R[1], R[2], R[3], R[4] and R[6] are defined as above in method (A).

Method (B)

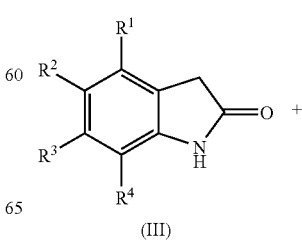

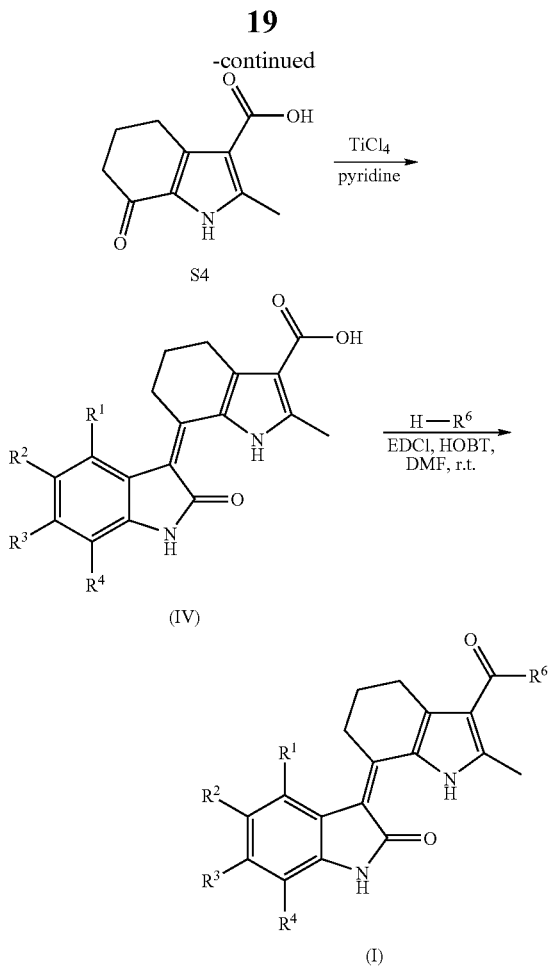

Condensation reagents used in the reaction above include, but are not limited to, N,N'-Dicyclohexylcarbodiimide (DCC), N,N'-Dissopropylcarbodiimide(DIC), 1-(3-Dimethylaminopropyl)-3-ethylcarbodiimide hydrochloride (EDCI), 2-Chloro-4,6-dimethoxy-1,3,5-triazine(CDMT), 2,4-Dichloro-6-methoxy-1,3,5-triazine(DCMT), 1,1'-Carbonyldiimidazole(CDI) and 1-Hydroxybenzotriazole(HOBt), preferably EDCI and HOBt.

Additionally, the compound S1 of the present invention may be synthesized using techniques reported in literatures of the chemical arts, e.g., Lartillot, Serge. et al, Bulletin de la Societe Chimique de France, 1964, 4:783; MacGee, J. et al. Biochem Med, 1977, 17:31; Evans D A, et al, J. C. S. Chem. Comm, 1978, 17:753, and related references cited thereof. The compounds of $HNR^8R^9$, $HN(R^{15})(CH_2)_rR^{16}$ and $H_2NCH_2CH(OH)CH_2—NR^8R^9$ are commercially available amines or may be synthesized using techniques or similar methods reported in literatures in the art, e.g., patent GB 276012, U.S. Pat. No. 1,790,096, patent CA 975364 and patent PCT WO2002066463 etc., and related references cited thereof. 2-indolinones of Formula (III) in Method (A) of the present invention are commercially available or may be synthesized using techniques or similar methods reported in literatures and books in the art, e.g., "Rodd's Chemistry of Carbon Compounds" 2nd, S. Coffey, Vol. IV, A section, 1973, pp. 448-450; Gassman P G, et al, J Org Chem, 1977, 42:1340; Wright W B et al, J Am Chem Soc, 1956, 78:221; Kisteneva, M S. Zhurnal Obshchei Khimii, 1956, 26:2251; Beckett A H, et al, Tetrahedron, 1968, 24:6093; Walker G N, J Am Chem Soc, 1955, 77:3844; Protiva M, et al, Collect Czech Chem Commun, 1979, 44:2108; McEvoy F J, et al, J Org Chem, 1973, 38:3350; Simet L, J Org Chem, 1963, 28:3580; Wieland T, et al, Chem Ber, 1963, 96:253; patent U.S. Pat. Nos. 3,882,236, 4,006,161 and 4,160,032, patent CN200410067904.2, and related references cited thereof.

At the same time, it will be appreciated by those skilled in the art that other synthetic pathways for forming the compounds of the invention are available and that the following is offered by way of example and not limitation.

3. Biological Evaluation

It is another aspect of this present invention that a compound herein, or its salt is used as a pharmaceutical composition for treating a protein kinase related disorder in an organism. A protein kinase related disorder described above is selected from the group consisting of a receptor tyrosine kinase related disorder, a non-receptor tyrosine kinase related disorder and a serine-threonine kinase related disorder. A protein kinase related disorder described above is selected from the group consisting of a VEGFR related disorder, an EGFR related disorder, a PDGFR related disorder, an IGFR related disorder and a flk related disorder. A protein kinase related disorder described above is selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, glioma, colorectal cancer, hepatic cancer, renal cancer, genitourinary cancer, pancreatic cancer and gastrointestinal cancer. A protein kinase related disorder described above is selected from the group consisting of diabetes, a hyperproliferation disorder, angiogenesis, an inflammatory disorder, an immunological disorder and a cardiovascular disorder. An organism described above is a mammal or a human.

It is also an aspect of the present invention that a pharmaceutical composition for treating a protein kinase related disorder in an organism comprises a compound of this invention or pharmaceutically acceptable salt and a pharmaceutically acceptable carrier or excipient 3.1 Enzyme Assay An ELISA (Enzyme-Linked Immunosorbent Sandwich Assay) procedure may be used to detect and measure the level of protein tyrosine kinase activity. Tyrosine kinases such as VEGFR-2, PDGFR-β and c-Kit etc. catalyze the phosphorylation reaction of ATP and biotin-labeled peptide substrate, which will be ceased when the kinase activity is inhibited. According to the principle of ELISA, a monoclonal antibody can react with phosphorylated substrate specially, so biotin-labeled substrate is binded to streptavidin-coated ELISA plate, and then binded to a HRP-labeled goat anti-mouse antibody. Finally TMB is added for a color reaction and the value of A450-A630 is read by ELISA plate reader. The OD value can reflect the inhibitory activity of the VEGFR-2, PDGFR-β, c-Kit tyrosine kinases etc. treated with the test compounds at the different concentrations. So, the assay may be used to measure the inhibition ratio of the compounds for the tyrosine kinase activity. Similar assays can be designed along the same lines for any PK using techniques well known in the art.

3.2 Tumor Cell Proliferation Assay (MTT Assay)

The assay used generally is the blue tetrazolium bromide (MTT) method. The yellow 3-(4,5-dimethylthiazolyl-2)-2,5-diphenyltetrazolium bromide (MTT) can be reduced to purple insoluble formazan by the succinodehydrogenase in the mitochondria of the active cells, but the dead cells do not have the same function. The amount of formazan can be detected by the microplate reader through the absorption value at 570 nm. The amount of formazan product generated is proportional to the number of living cells in the sample, so the OD value may reflect the number of living cells and the ability of a test drug to inhibit or kill cells. The MTT assay may be used in determining the ability of different compounds of the present invention to inhibit one or more cancer cells proliferation. Similar assays can be designed along the same lines for any cancer cell using techniques well known in the art.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of 2-methyl-7-oxo-4,5,6,7-tetrahydro-1H-indole-3-carboxylic acid (S4)

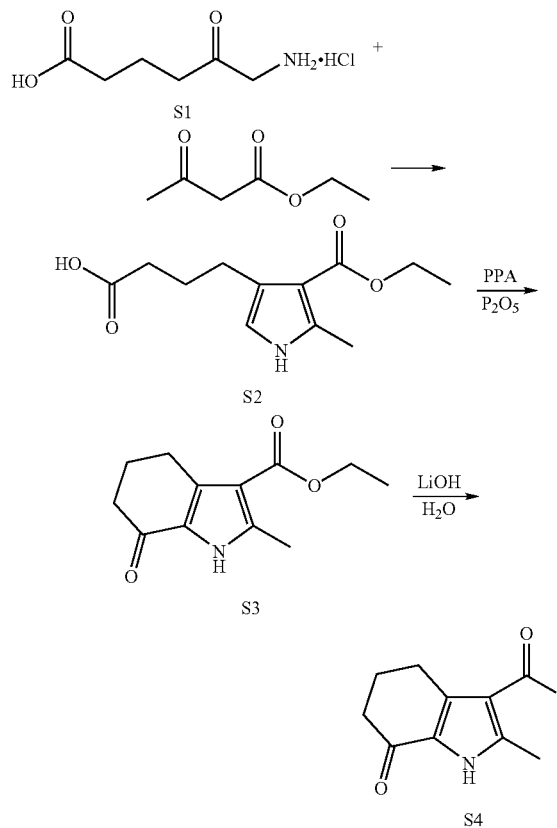

Step 1

6-amino-5-oxohexanoic acid hydrochloride (S1) 22.44 g (0.12 mol) (Lartillot, Serge. et al, Bulletin de la Societe Chimique de France, 1964, 4:783) was solved in about 6.1 L sodium dihydrogen phosphate buffer (300 g sodium dihydrogen phosphate was solved in 6 L water, then Saturated sodium hydroxide aqueous solution was added until a pH of about 6.5 was reached), and ethyl acetoacetate 16.12 g (0.12 mol) was added to the above-mentioned solution. The reaction solution was refluxed for half an hour, cooled to room temperature and $Na_2CO_3$ was added until a pH of about 8 was reached. The mixture was extracted with 100 ml $CHCl_3$ and Aqueous phase was acidified with 6 mol/L HCl to pH 1. The brown solid was collected by filtration, washed with water and dried in vacuum condition to give 20.29 g (71%) 4-(4-(ethoxycarbonyl)-5-methyl-1H-pyrrol-3-yl)butanoic acid (S2).

$^1$HNMR (500 MHz, DMSO-$d_6$) δ 11.89 (s, 1H, —COOH), 10.90 (s, 1H, —NH-1), 6.38 (s, 1H, pyrrole-2), 4.14 (q, 2H, —CH$_2$CH$_3$), 2.56 (t, 2H, —CH$_2$CH$_2$CH$_2$COOH), 2.36 (s, 3H, —CH$_3$-5), 2.18 (t, 2H, —CH$_2$CH$_2$—COOH), 1.71 (m, 2H, —CH$_2$CH$_2$CH$_2$COOH), 1.25 (t, 3H, —CH$_2$CH$_3$).

Step 2

$P_2O_5$ 7.1 g was added into polyphosphoric acid 142 g, then after the mixture was stirred for 30 minutes at 70° C., 4-(4-(ethoxycarbonyl)-5-methyl-1H-pyrrol-3-yl)butanoic acid (S2) 6.3 g (0.026 mol) was added and stirred for 48 hours. The mixture was poured into the ice water and adjusted pH to 8 with saturated sodium carbonate solution, then extracted with ethyl acetate. The organic phase was washed with water and saturated sodium chloride solution, then dried over anhydrous $Na_2SO_4$ and concentrated to saturated solutions in vacuo. The residue was colded to −5° C., then the white solid was collected by filtration and dried in vacuum to give 3.5 g (61%) ethyl 2-methyl-7-oxo-4,5,6,7-tetrahydro-1H-indole-3-carboxylate (S3).

$^1$HNMR (500 MHz, CDCl$_3$) δ 10.23 (s, 1H, —NH-1), 4.30 (q, 2H, —CH$_2$CH$_3$), 3.00 (t, 2H, —CH$_2$-4), 2.59 (s, 3H, —CH$_3$-2), 2.50 (t, 2H, —CH$_2$-6), 2.12 (m, 2H, —CH$_2$-5), 1.36 (t, 3H, —CH$_2$CH$_3$);

ESI-MS: 222.1 [M+H]$^+$; 220.1 [M−H]$^-$.

Step 3 ethyl 2-methyl-7-oxo-4,5,6,7-tetrahydro-1H-indole-3-carboxylate (S3) 1.0 g (4.5 mmol) in 25 ml aq. LiOH solution (1 mol/L) was stirred for 48 hours at 70° C. The mixture was poured into the ice water, then acidified with 6 mol/L HCl to pH 1 to 2. The gray solid was collected by filtration, washed with water and dried in vacuum condition to give 0.64 g (74%) of the titled compound.

$^1$HNMR (500 MHz, DMSO-$d_6$) δ 12.03 (bs, 2H, —NH-1, —COOH), 2.87 (t, 2H, —CH$_2$-4), 2.42 (s, 3H, —CH$_3$-2), 2.34 (t, 2H, —CH$_2$-6), 1.98 (m, 2H, —CH$_2$-5);

ESI-MS: 194.1 [M+H]$^+$.

Example 2

Synthesis of N-(2-(diethylamino)ethyl)-2-methyl-7-oxo-4,5,6,7-tetrahydro-1H-indole-3-carboxamide (II-1)

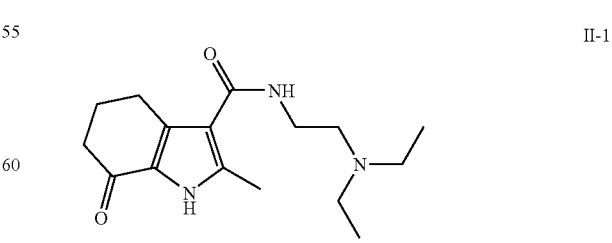

A mixture of 2-methyl-7-oxo-4,5,6,7-tetrahydro-1H-indole-3-carboxylic acid (S4) 0.2 g (1.0 mmol), HOBt 0.16 g (1.2 mmol), EDCI 0.24 g (1.2 mmol) and triethylamine 0.2 g (2.0 mmol) in 10 ml DMF was stirred at room temperature for 20 min, then $N^1,N^1$-diethylethane-1,2-diamine 0.24 g (2.1 mmol) was added. After stirred at room temperature for 24 hours, the mixture was poured into the ice water and extracted with $CH_2Cl_2$. The organic layer separated was washed with water and saturated sodium chloride solution, then dried over anhydrous $Na_2SO_4$ and concentrated in vacuo. The residue was purified by a silica gel column, eluted with $CH_2Cl_2$/MeOH (30:1), to give 0.23 g (79%) of the titled compound as a white solid.

$^1$HNMR (500 MHz, CDCl$_3$) δ 9.67 (s, 1H, —NH-1), 6.41 (s, 1H, —CONH—), 3.46 (bs, 2H, —CONHCH$_2$CH$_2$—), 2.93 (t, 2H, —CH$_2$-4), 2.64~2.59 (m, 6H, —NHCH$_2$CH$_2$N(CH$_2$CH$_3$)$_2$), 2.58 (s, 3H, —CH$_3$-2), 2.49 (t, 2H, —CH$_2$-6), 2.16 (m, 2H, —CH$_2$-5), 1.04 (s, 6H, —(CH$_2$CH$_3$)$_2$);

ESI-MS: 292.2 [M+H]$^+$, 314.2[M+Na]$^+$; 290.3 [M−H]$^−$.

Example 3

Synthesis of N-(2-hydroxyethyl)-2-methyl-7-oxo-4,5,6,7-tetrahydro-1H-indole-3-carboxamide (II-2)

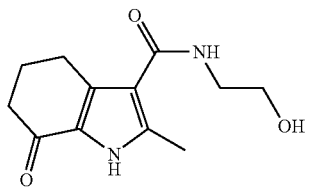

II-2

Similar procedure as Example 2, 2-methyl-7-oxo-4,5,6,7-tetrahydro-1H-indole-3-carboxylic acid (S4) 0.2 g (1.0 mmol) and 2-aminoethanol 0.13 g (2.1 mmol) was reacted. The reaction solution was concentrated and purified by a silica gel column, eluted with $CH_2Cl_2$/MeOH (10:1), to give 0.20 g (85%) of the titled compound as a white solid.

$^1$HNMR (300 MHz, DMSO-d$_6$) δ 11.84 (s, 1H, —NH-1), 7.17 (t, 1H, —CONH—), 4.69 (t, 1H, —OH), 3.48 (q, 2H, —CONHCH$_2$CH$_2$—), 3.28 (q, 2H, —CH$_2$OH), 2.79 (t, 2H, —CH$_2$-4), 2.34~2.31 (m, 5H, —CH$_3$-2, —CH$_2$-6), 1.97 (m, 2H, —CH$_2$-5);

ESI-MS: 237.1 [M+H]$^+$, 259.1[M+Na]$^+$.

Example 4

Synthesis of N-(2-(dimethylamino)ethyl)-2-methyl-7-oxo-4,5,6,7-tetrahydro-1H-indole-3-carboxamide (II-3)

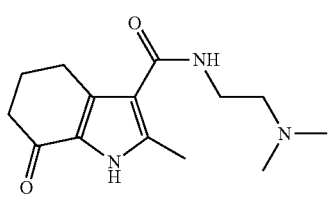

II-3

Similar procedure as Example 2, 2-methyl-7-oxo-4,5,6,7-tetrahydro-1H-indole-3-carboxylic acid (S4) 0.2 g (1.0 mmol) and $N^1,N^1$-dimethylethane-1,2-diamine 0.19 g (2.1 mmol) was reacted to give 0.21 g (80%) of the titled compound as a white solid.

$^1$HNMR (300 MHz, CDCl$_3$) δ 10.80 (s, 1H, —NH-1), 6.17 (s, 1H, —CONH—), 3.51 (q, 2H, —CONHCH$_2$CH$_2$—), 2.80 (t, 2H, —CH$_2$-4), 2.55 (t, 2H, —CH$_2$-6), 2.51 (s, 3H, —CH$_3$-2), 2.46 (t, 2H, —CH$_2$N(CH$_3$)$_2$), 2.29 (s, 6H, —CH$_2$N(CH$_3$)$_2$), 2.09 (m, 2H, —CH$_2$-5);

ESI-MS: 264.1 [M+H]$^+$, 286.2[M+Na]$^+$.

Example 5

Synthesis of N-(3-(dimethylamino)propyl)-2-methyl-7-oxo-4,5,6,7-tetrahydro-1H-indole-3-carboxamide (II-4)

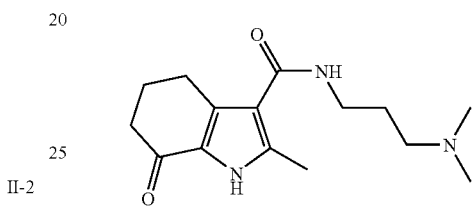

II-4

Similar procedure as Example 2, 2-methyl-7-oxo-4,5,6,7-tetrahydro-1H-indole-3-carboxylic acid (S4) 0.2 g (1.0 mmol) and $N^1,N^1$-dimethylpropane-1,3-diamine 0.21 g (2.1 mmol) was reacted to give 0.23 g (83%) of the titled compound as a white solid.

$^1$HNMR (300 MHz, CDCl$_3$) δ 10.76 (s, 1H, —NH-1), 7.11 (s, 1H, —CONH—), 3.50 (t, 2H, —CONHCH$_2$CH$_2$CH$_2$—), 2.89 (t, 2H, —CH$_2$-4), 2.56 (s, 3H, —CH$_3$-2), 2.50~2.41 (m, 4H, —CH$_2$-6, —CH$_2$N(CH$_3$)$_2$), 2.21 (s, 6H, —CH$_2$N(CH$_3$)$_2$), 2.13 (m, 2H, —CH$_2$-5), 1.72 (m, 2H, —CONHCH$_2$CH$_2$CH$_2$—);

ESI-MS: 278.2 [M+H]$^+$, 300.1[M+Na]$^+$.

Example 6

Synthesis of 2-methyl-N-(2-morpholinoethyl)-7-oxo-4,5,6,7-tetrahydro-1H-indole-3-carboxamide (II-5)

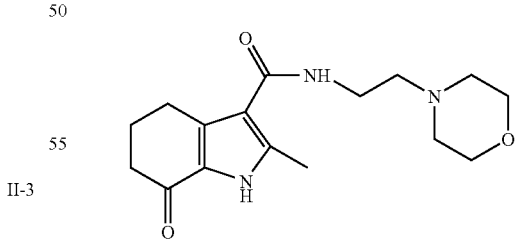

II-5

Similar procedure as Example 2, 2-methyl-7-oxo-4,5,6,7-tetrahydro-1H-indole-3-carboxylic acid (S4) 0.2 g (1.0 mmol) and 2-morpholinoethanamine 0.27 g (2.1 mmol) was reacted to give 0.25 g (82%) of the titled compound as a white solid.

$^1$HNMR (300 MHz, CDCl$_3$) δ 6.32 (bs, 1H, —CONH—), 3.75 (t, 4H, —CH$_2$N(CH$_2$CH$_2$)$_2$O), 3.52 (q, 2H, —CONH

CH$_2$), 2.93 (t, 2H, —CH$_2$-4), 2.59 (t, 5H, —CH$_3$-2, —CH$_2$-6), 2.53 (m, 6H, —CH$_2$N(CH$_2$CH$_2$)$_2$O), 2.16 (m, 2H, —CH$_2$-5);

ESI-MS: 306.2 [M+H]$^+$.

Example 7

Synthesis of 2-methyl-7-oxo-N-(2-(piperidin-1-yl)ethyl)-4,5,6,7-tetrahydro-1H-indole-3-carboxamide (II-6)

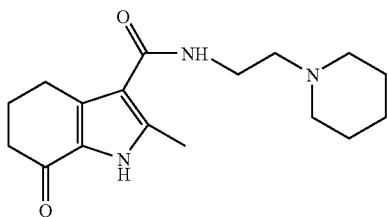

II-6

Similar procedure as Example 2, 2-methyl-7-oxo-4,5,6,7-tetrahydro-1H-indole-3-carboxylic acid (S4) 0.2 g (1.0 mmol) and 2-(piperidin-1-yl)ethanamine 0.27 g (2.1 mmol) was reacted to give 0.26 g (86%) of the titled compound as a white solid.

$^1$HNMR (300 MHz, CDCl$_3$) δ 10.21 (bs, 1H, —NH-1), 6.47 (bs, 1H, —CONH—), 3.48 (q, 2H, —CONHCH$_2$CH$_2$—), 2.93 (t, 2H, —CH$_2$-4), 2.58 (s, 3H, —CH$_3$-2), 2.51 (m, 4H, —CH$_2$-6, —NHCH$_2$CH$_2$N(CH$_2$CH$_2$)$_2$CH$_2$), 2.43 (s, 4H, —NHCH$_2$CH$_2$N(CH$_2$CH$_2$)$_2$CH$_2$), 2.15 (m, 2H, —CH$_2$-5), 1.59 (m, 4H, —N(CH$_2$CH$_2$)$_2$CH$_2$), 1.46 (m, 2H, —N(CH$_2$CH$_2$)$_2$CH$_2$);

ESI-MS: 304.2 [M+H]$^+$.

Example 8

Synthesis of 2-methyl-7-oxo-N-(2-(pyrrolidin-1-yl)ethyl)-4,5,6,7-tetrahydro-1H-indole-3-carboxamide (II-7)

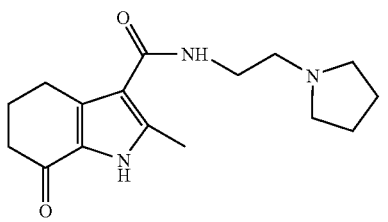

II-7

Similar procedure as Example 2, 2-methyl-7-oxo-4,5,6,7-tetrahydro-1H-indole-3-carboxylic acid (S4) 0.2 g (1.0 mmol) and 2-(pyrrolidin-1-yl)ethanamine 0.24 g (2.1 mmol) was reacted to give 0.21 g (73%) of the titled compound as a white solid.

$^1$HNMR (300 MHz, CDCl$_3$) δ 10.81 (bs, 1H, —NH-1), 6.33 (bs, 1H, —CONH—), 3.55 (q, 2H, —CONHCH$_2$), 2.82 (m, 4H, —CH$_2$-4, —CH$_2$N(CH$_2$CH$_2$)$_2$), 2.68 (s, 4H, —CH$_2$N(CH$_2$CH$_2$)), 2.50 (s, 3H, —CH$_3$-2), 2.46 (t, 2H, —CH$_2$-6), 2.09 (m, 2H, —CH$_2$-5), 1.82 (m, 4H, —CH$_2$N(CH$_2$CH$_2$)$_2$,);

ESI-MS: 290.1 [M+H]$^+$; 312.1 [M+Na]$^+$.

Example 9

Synthesis of 2-methyl-N-(3-morpholinopropyl)-7-oxo-4,5,6,7-tetrahydro-1H-indole-3-carboxamide (II-8)

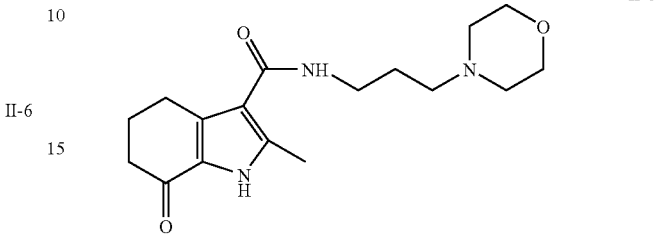

II-8

Similar procedure as Example 2, 2-methyl-7-oxo-4,5,6,7-tetrahydro-1H-indole-3-carboxylic acid (S4) 0.2 g (1.0 mmol) and 3-morpholinopropan-1-amine 0.30 g (2.1 mmol) was reacted to give 0.27 g (85%) of the titled compound as a white solid.

$^1$HNMR (300 MHz, CDCl$_3$) δ 10.29 (bs, 1H, —NH-1), 6.19 (bs, 1H, —CONH—), 3.62 (t, 4H, —CH$_2$N(CH$_2$CH$_2$)$_2$O), 3.46 (q, 2H, —CONHCH$_2$), 2.93 (t, 2H, —CH$_2$-4), 2.57 (s, 3H, —CH$_3$-2), 2.48 (m, 8H, —CH$_2$-6, —CH$_2$CH$_2$N(CH$_2$CH$_2$)$_2$O), 2.15 (m, 2H, —CH$_2$-5), 1.78 (m, 2H, —CH$_2$CH$_2$N(CH$_2$CH$_2$)$_2$O);

ESI-MS: 320.2 [M+H]$^+$; 342.2 [M+Na]$^+$.

Example 10

Synthesis of N-(3-(diethylamino)propyl)-2-methyl-7-oxo-4,5,6,7-tetrahydro-1H-indole-3-carboxamide (II-9)

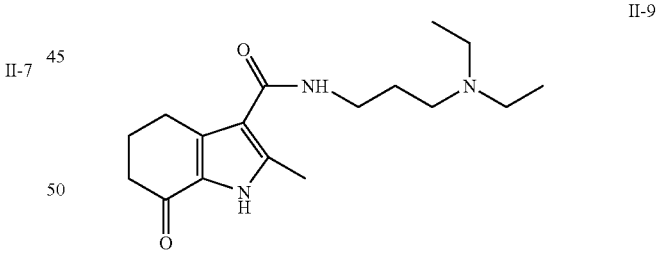

II-9

Similar procedure as Example 2, 2-methyl-7-oxo-4,5,6,7-tetrahydro-1H-indole-3-carboxylic acid (S4) 0.2 g (1.0 mmol) and N$^1$,N$^1$-diethylpropane-1,3-diamine 0.27 g (2.1 mmol) was reacted to give 0.26 g (85%) of the titled compound as a white solid.

$^1$HNMR (300 MHz, CDCl$_3$) δ 9.98 (bs, 1H, —NH-1), 6.95 (bs, 1H, —CONH—), 3.52 (q, 2H, —CONHCH$_2$CH$_2$—), 2.90 (t, 2H, —CH$_2$-4), 2.55 (m, 11H, —CH$_2$CH$_2$N(CH$_2$CH$_3$)$_2$, —CH$_2$-6, —CH$_3$-2), 2.12 (m, 2H, —CH$_2$-5), 1.74 (m, 2H, —NHCH$_2$CH$_2$CH$_2$—), 1.01 (t, 6H, —(CH$_2$CH$_3$)$_2$);

ESI-MS: 306.2 [M+H]$^+$.

Example 11

Synthesis of 2-methyl-7-oxo-N-(3-(pyrrolidin-1-yl)propyl)-4,5,6,7-tetrahydro-1H-indole-3-carboxamide (II-10)

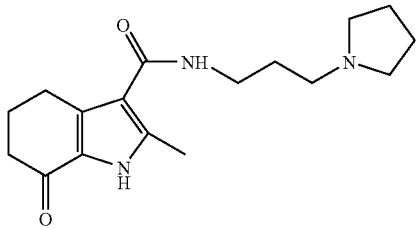

Similar procedure as Example 2, 2-methyl-7-oxo-4,5,6,7-tetrahydro-1H-indole-3-carboxylic acid (S4) 0.2 g (1.0 mmol) and 3-(pyrrolidin-1-yl)propan-1-amine 0.27 g (2.1 mmol) was reacted to give 0.25 g (82%) of the titled compound as a white solid.

$^1$HNMR (300 MHz, CDCl$_3$) δ 10.06 (bs, 1H, —NH-1), 6.92 (bs, 1H, —CONH—), 3.51 (q, 2H, —CONHCH$_2$), 2.90 (t, 2H, —CH$_2$-4), 2.61 (t, 2H, —CH$_2$-6), 2.56 (s, 3H, —CH$_3$-2), 2.50 (m, 6H, —CH$_2$N(CH$_2$CH$_2$)$_2$), 2.13 (m, 2H, —CH$_2$-5), 1.76 (m, 6H, —CH$_2$CH$_2$N(CH$_2$CH$_2$)$_2$);

ESI-MS: 304.2 [M+H]$^+$; 326.2 [M+Na]$^+$.

Example 12

Synthesis of 2-methyl-N-(3-(4-methylpiperazin-1-yl)propyl)-7-oxo-4,5,6,7-tetrahydro-1H-indole-3-carboxamide (II-11)

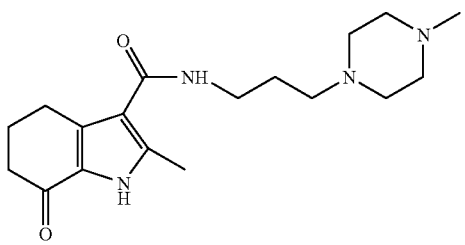

Similar procedure as Example 2, 2-methyl-7-oxo-4,5,6,7-tetrahydro-1H-indole-3-carboxylic acid (S4) 0.2 g (1.0 mmol) and 3-(4-methylpiperazin-1-yl)propan-1-amine 0.33 g (2.1 mmol) was reacted to give 0.26 g (78%) of the titled compound as a white solid.

$^1$HNMR (300 MHz, CDCl$_3$) δ 10.43 (bs, 1H, —NH-1), 6.44 (bs, 1H, —CONH—), 3.49 (q, 2H, —CONH CH$_2$CH$_2$—), 2.91 (t, 2H, —CH$_2$-4), 2.67 (m, 10H, —CH$_2$N(CH$_2$CH$_2$)$_2$NCH$_3$), 2.56 (s, 3H, —CH$_3$-2), 2.44 (t, 2H, —CH$_2$-6), 2.37 (s, 3H, —NCH$_3$), 2.10 (m, 2H, —CH$_2$-5), 1.85 (m, 2H, —CH$_2$CH$_2$CH$_2$—);

ESI-MS: 306.2 [M+H]$^+$.

Example 13

Synthesis of N-(3-(diethylamino)-2-hydroxypropyl)-2-methyl-7-oxo-4,5,6,7-tetrahydro-1H-indole-3-carboxamide (II-12)

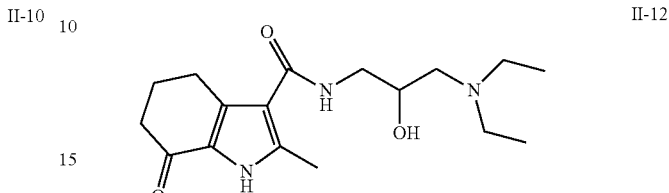

A mixture of 2-methyl-7-oxo-4,5,6,7-tetrahydro-1H-indole-3-carboxylic acid (S4) 0.2 g (1.0 mmol), HOBt 0.16 g (1.2 mmol), EDCI 0.24 g (1.2 mmol) and triethylamine 0.2 g (2.0 mmol) in 10 ml DMF was stirred at room temperature for 20 min, then 1-amino-3-(diethylamino)propan-2-ol 0.31 g (2.1 mmol) was added. After stirred at room temperature for 24 hours, the mixture was poured into the ice water and extracted with CH$_2$Cl$_2$. The organic layer separated was washed with water and saturated sodium chloride solution, then dried over anhydrous Na$_2$SO$_4$ and concentrated in vacuo. The residue was purified by a silica gel column, eluted with CH$_2$Cl$_2$/MeOH (3:1), to give 0.26 g (81%) of the titled compound as a white solid.

$^1$HNMR (300 MHz, CDCl$_3$) δ 10.09 (s, 1H, —NH-1), 6.74 (t, 1H, —CONH—), 4.40 (m, 1H, —CONHCH(H)—), 3.83 (m, 1H, —CONHCH(H)—), 3.58 (m, 1H, —CH(OH)—), 3.26~3.15 (m, 6H, —CH$_2$N(CH$_2$CH$_3$)$_2$), 3.00 (t, 2H, —CH$_2$-4), 2.56 (s, 3H, —CH$_3$-2), 2.46 (t, 2H, —CH$_2$-6), 2.15 (m, 2H, —CH$_2$-5), 1.44 (t, 6H, —CH$_2$N(CH$_2$CH$_3$)$_2$);

ESI-MS: 322.2 [M+H]$^+$.

Example 14

Synthesis of N-(3-(dimethylamino)-2-hydroxypropyl)-2-methyl-7-oxo-4,5,6,7-tetrahydro-1H-indole-3-carboxamide (II-13)

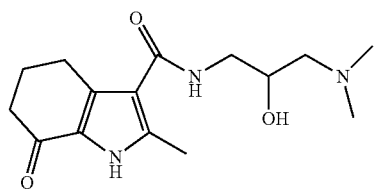

Similar procedure as Example 13, 2-methyl-7-oxo-4,5,6,7-tetrahydro-1H-indole-3-carboxylic acid (S4) 0.2 g (1.0 mmol) and 1-amino-3-(dimethylamino)propan-2-ol 0.25 g (2.1 mmol) was reacted to give 0.24 g (82%) of the titled compound as a white solid.

$^1$HNMR (300 MHz, CDCl$_3$) δ 10.43 (s, 1H, —NH-1), 6.23 (t, 1H, —CONH—), 3.86 (m, 1H, —CONHCH(H)—), 3.69 (m, 1H, —CONHCH(H)—), 3.32 (m, 1H, —CH(OH)—), 2.93 (t, 2H, —CH₂-4), 2.58 (s, 3H, —CH₃-2), 2.49 (t, 2H, —CH₂-6), 2.40~2.30 (m, 8H, —CH₂N(CH₃)₂), 2.14 (m, 2H, —CH₂-5);

ESI-MS: 294.1 [M+H]⁺.

Example 15

Synthesis of N-(2-hydroxy-3-morpholinopropyl)-2-methyl-7-oxo-4,5,6,7-tetrahydro-1H-indole-3-carboxamide (II-14)

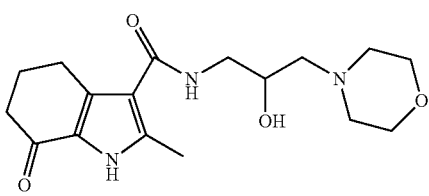

II-14

¹HNMR (300 MHz, CDCl₃) δ 10.00 (s, 1H, —NH-1), 6.08 (s, 1H, —CONH—), 3.94 (s, 1H, —CONHCH(H)—), 3.75~3.71 (m, 6H, —OH, —CONHCH(H)—, —CH₂N(CH₂CH₂)₂O), 3.33 (m, 1H, —CH(OH)—), 2.90 (t, 2H, —CH₂-4), 2.67 (m, 2H, —CH₂N(CH₂CH₂)₂O), 2.58 (s, 3H, —CH₃-2), 2.51~2.40 (m, 6H, —CH₂-6, —CH₂N(CH₂CH₂)₂O), 2.15 (m, 2H, —CH₂-5);

ESI-MS: 336.0 [M+H]⁺, 358.0[M+Na]⁺.

Example 16

Synthesis of N-(2-hydroxy-3-(pyrrolidin-1-yl)propyl)-2-methyl-7-oxo-4,5,6,7-tetrahydro-1H-indole-3-carboxamide (II-15)

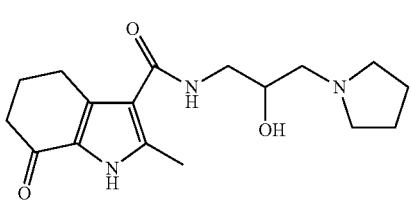

II-15

Similar procedure as Example 13, 2-methyl-7-oxo-4,5,6,7-tetrahydro-1H-indole-3-carboxylic acid (S4) 0.2 g (1.0 mmol) and 1-amino-3-(pyrrolidin-1-yl)propan-2-ol 0.30 g (2.1 mmol) was reacted to give 0.26 g (82%) of the titled compound as a white solid.

¹HNMR (300 MHz, CDCl₃) δ 9.61 (s, 1H, —NH-1), 6.20 (s, 1H, —CONH—), 3.92 (m, 1H, —CONHCH(H)—), 3.76 (m, 1H, —CONHCH(H)—), 3.39 (m, 1H, —CH(OH)—), 2.96 (t, 2H, —CH₂-4), 2.75 (m, 3H, alkyl), 2.60~2.46 (m, 8H, —CH₂-6, —CH₃-2, alkyl), 2.20 (m, 2H, —CH₂-5), 1.84 (s, 4H, —CH₂N(CH₂CH₂CH₂CH₂));

ESI-MS: 320.2[M+H]⁺, 342.1[M+Na]⁺; 318.2 [M−H]⁻.

Example 17

Synthesis of N-(2-hydroxy-3-(piperidin-1-yl)propyl)-2-methyl-7-oxo-4,5,6,7-tetrahydro-1H-indole-3-carboxamide (II-16)

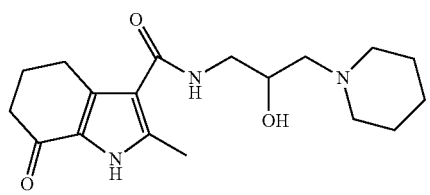

II-16

Similar procedure as Example 13, 2-methyl-7-oxo-4,5,6,7-tetrahydro-1H-indole-3-carboxylic acid (S4) 0.2 g (1.0 mmol) and 1-amino-3-(piperidin-1-yl)propan-2-ol 0.34 g (2.1 mmol) was reacted to give 0.26 g (78%) of the titled compound as a white solid.

¹HNMR (300 MHz, CDCl₃) δ 10.33 (s, 1H, —NH-1), 6.11 (t, 1H, —CONH—), 3.88 (m, 1H, —CONHCH(H)—), 3.68 (m, 1H, —CONHCH(H)—), 3.29 (m, 1H, —CH(OH)—), 2.92 (t, 2H, —CH₂-4), 2.63~2.57 (m, 5H, —CH₂N(CH₂)₅, —CH₃-2), 2.49 (t, 2H, —CH₂-6), 2.36 (m, 4H, —CH₂N(CH₂CH₂CH₂CH₂CH₂)), 2.17 (m, 2H, —CH₂-5), 1.58 (m, 4H, —N(CH₂CH₂CH₂CH₂CH₂)), 1.46 (m, 2H, —N(CH₂CH₂CH₂CH₂CH₂));

ESI-MS: 334.2[M+H]⁺, 356.3[M+Na]⁺; 332.3 [M−H]⁻.

Example 18

Synthesis of N-(2-hydroxy-3-(4-methylpiperazin-1-yl)propyl)-2-methyl-7-oxo-4,5,6,7-tetrahydro-1H-indole-3-carboxamide (II-17)

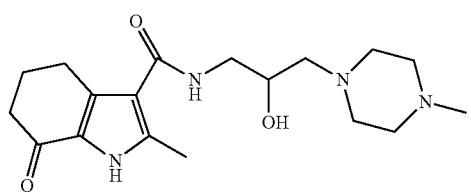

II-17

Similar procedure as Example 13, 2-methyl-7-oxo-4,5,6,7-tetrahydro-1H-indole-3-carboxylic acid (S4) 0.2 g (1.0 mmol) and 1-amino-3-(4-methylpiperazin-1-yl)propan-2-ol 0.36 g (2.1 mmol) was reacted to give 0.25 g (72%) of the titled compound as a white solid.

¹HNMR (300 MHz, CDCl₃) δ 9.53 (s, 1H, —NH-1), 6.09 (s, 1H, —CONH—), 3.93 (m, 1H, —CONHCH(H)—), 3.69 (m, 1H, —CONHCH(H)—), 3.33 (m, 1H, —CH(OH)—), 2.92 (t, 2H, —CH₂-4), 2.78 (bs, 2H, —CH₂N(CH₂CH₂)₂NCH₃), 2.56~2.40 (m, 13H, —CH₃-2, —CH₂N(CH₂CH₂)₂NCH₃, —CH₂-6), 2.33 (s, 3H, —N(CH₂CH₂)₂NCH₃), 2.15 (m, 2H, —CH₂-5);

ESI-MS: 349.2 [M+H]⁺.

Example 19

Synthesis of N-(3-(cyclohexyl(methyl)amino)-2-hydroxypropyl)-2-methyl-7-oxo-4,5,6,7-tetrahydro-1H-indole-3-carboxamide (II-18)

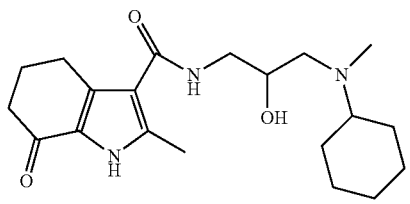

II-18

Step 1

A mixture of 2-(3-chloro-2-hydroxypropyl)isoindoline-1,3-dione 7.2 g (0.03 mol) (Weizmann, M. et al. Bull. soc. chim. 1930, 47:356-61) and N-methylcyclohexanamine 6.8 g (0.06 mol) in 25 ml ethanol was refluxed for 6 hours, then evaporated in vacuo. The oil residue was added into 60 ml 20% aq. HCl and refluxed for another 3 hours. After cooled to room temperature, the precipitate was filtered off. The filtrate was concentrated to about 15 ml in vacuo, then basified to pH 13 to 14 with solid NaOH and extracted with $CH_2Cl_2$. The organic layer separated was dried over anhydrous $Na_2SO_4$ and concentrated in vacuo to give 1.75 g (31%) 1-amino-3-(cyclohexyl(methyl)amino)propan-2-ol as a colorless liquid.

ESI-MS: 187.1 [M+H]$^+$.

Step 2

Similar procedure as Example 13, 2-methyl-7-oxo-4,5,6,7-tetrahydro-1H-indole-3-carboxylic acid (S4) 0.2 g (1.0 mmol) and 1-amino-3-(cyclohexyl(methyl)amino)propan-2-ol 0.39 g (2.1 mmol) were reacted to give 0.30 g (83%) of the titled compound as a white solid.

$^1$HNMR (300 MHz, CDCl$_3$) δ 9.91 (s, 1H, —NH-1), 6.43 (s, 1H, —CONH—), 4.16 (m, 1H, —CONHCH(H)—), 3.77 (m, 1H, —CONHCH(H)—), 3.47 (m, 1H, —CH(OH)—), 2.97~2.87 (m, 4H, —CH$_2$-4, —CH(OH)—CH$_2$N—), 2.62 (s, 3H, —CH$_3$), 2.58 (s, 3H, —CH$_3$), 2.48 (t, 2H, —CH$_2$-6), 2.18~2.01 (m, 4H, —CH$_2$-5, cyclohexyl), 1.90 (d, 2H, cyclohexyl), 1.71 (d, 1H, cyclohexyl), 1.41~1.22 (m, 5H, cyclohexyl), 1.10 (m, 1H, cyclohexyl);

ESI-MS: 362.3[M+H]$^+$.

Example 20

Synthesis of 2-methyl-7-[1,2-dihydro-2-oxo-3H-indol-(Z)-3-ylidene]-4,5,6,7-tetrahydro-1H-indole-3-carboxylic acid (IV-1)

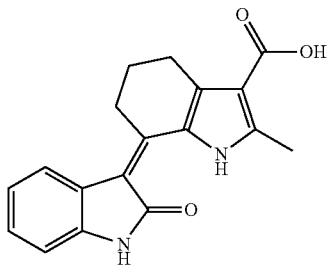

IV-1

TiCl$_4$ 0.4 ml was added into a mixture of indolin-2-one 0.37 g (2.8 mmol) and 2-methyl-7-oxo-4,5,6,7-tetrahydro-1H-indole-3-carboxylic acid (S4) 0.5 g (2.6 mmol) in 15 ml anhydrous pyridine. After stirred for 10 hours at 100 to 110° C., the mixture was poured into ice water, then acidified with 6 mol/L HCl to pH 1 to 2. The precipitate was collected by filtration, washed with water and dried in vacuum condition to give 0.58 g (74%) of the titled compound as a yellow brown solid. Recrystallization of the crude product in DMF and water gave 0.43 g (54%) of the titled compound as a yellow solid.

$^1$HNMR (300 MHz, DMSO-d$_6$) δ 14.64 (s, 1H, —NH-1), 12.03 (s, 1H, —COOH), 10.91 (s, 1H, —NH-1'), 7.63 (d, 1H, J=7.56 Hz, H-4'), 7.14 (t, 1H, H-6'), 6.99 (t, 1H, H-5'), 6.91 (d, 1H, J=6.69 Hz, H-7'), 3.12 (t, 2H, —CH$_2$-4), 2.92 (t, 2H, —CH$_2$-6), 2.53 (s, 3H, —CH$_3$-2), 1.94 (m, 2H, —CH$_2$-5);

ESI-MS: 307.2 [M–H]$^-$.

Example 21

Synthesis of 2-methyl-7-[1,2-dihydro-5-fluoro-2-oxo-3H-indol-(Z)-3-ylidene]-4,5,6,7-tetrahydro-1H-indole-3-carboxylic acid (IV-2)

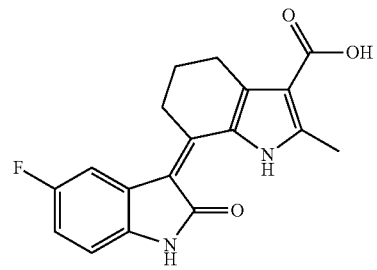

IV-2

Similar procedure as Example 20, 5-fluoroindolin-2-one 0.42 g (2.8 mmol) and 2-methyl-7-oxo-4,5,6,7-tetrahydro-1H-indole-3-carboxylic acid (S4) 0.5 g (2.6 mmol) were reacted for 20 hours at 50 to 60° C., and 0.30 g (35%) of the titled compound as a yellow solid was obtained.

$^1$HNMR (300 MHz, DMSO-d$_6$) δ 14.68 (s, 1H, —NH-1), 12.08 (s, 1H, —COOH), 10.93 (s, 1H, —NH-1'), 7.45 (dd, 1H, J=11.91 Hz, H-4'), 6.97 (t, 1H, H-6'), 6.87 (t, 1H, H-7'), 3.08 (t, 2H, —CH$_2$-4), 2.92 (t, 2H, —CH$_2$-6), 2.54 (s, 3H, —CH$_3$-2), 1.94 (m, 2H, —CH$_2$-5);

ESI-MS: 325.2 [M–H]$^-$.

Example 22

Synthesis of 2-methyl-7-[1,2-dihydro-5-chloro-2-oxo-3H-indol-(Z)-3-ylidene]-4,5,6,7-tetrahydro-1H-indole-3-carboxylic acid (IV-3)

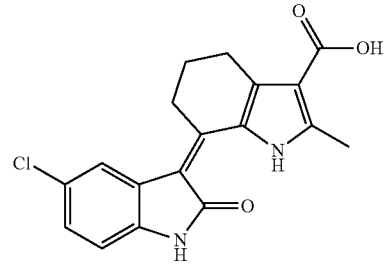

IV-3

Similar procedure as Example 20, 5-chloroindolin-2-one 0.47 g (2.8 mmol) and 2-methyl-7-oxo-4,5,6,7-tetrahydro-1H-indole-3-carboxylic acid (S4) 0.5 g (2.6 mmol) were reacted for 1 hour at 145 to 150° C., and 0.28 g (31%) of the titled compound as a yellow solid was obtained.

¹HNMR (500 MHz, DMSO-d₆) δ 14.60 (s, 1H, —NH-1), 12.04 (s, 1H, —COOH), 11.04 (s, 1H, —NH-1'), 7.60 (s, 1H, H-4'), 7.42 (d, 1H, J=8.5 Hz, H-6'), 6.91 (d, 1H, J=8.2 Hz, H-7'), 3.08 (t, 2H, —CH₂-4), 2.93 (t, 2H, —CH₂-6), 2.54 (s, 3H, —CH₃-2), 1.96 (m, 2H, —CH₂-5);

ESI-MS: 341.1 [M−H]⁻.

Example 23

Synthesis of 2-methyl-7-[1,2-dihydro-5-methyl-2-oxo-3H-indol-(Z)-3-ylidene]-4,5,6,7-tetrahydro-1H-indole-3-carboxylic acid (IV-4)

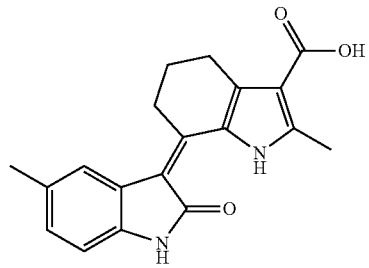

IV-4

Similar procedure as Example 20, 5-methylindolin-2-one 0.41 g (2.8 mmol) and 2-methyl-7-oxo-4,5,6,7-tetrahydro-1H-indole-3-carboxylic acid (S4) 0.5 g (2.6 mmol) were reacted for 13 hours at 80 to 90° C., and 0.39 g (46%) of the titled compound as a yellow solid was obtained.

¹HNMR (500 MHz, DMSO-d₆) δ 14.66 (s, 1H, —NH-1), 12.03 (s, 1H, —COOH), 10.82 (s, 1H, —NH-1'), 7.46 (s, 1H, H-4'), 6.96 (d, 1H, J=7.70 Hz, H-6'), 6.80 (d, 1H, J=7.75 Hz, H-7'), 3.10 (t, 2H, —CH₂-4), 2.93 (t, 2H, —CH₂-6), 2.53 (s, 3H, —CH₃-2), 2.32 (s, 3H, —CH₃-5'), 1.95 (m, 2H, —CH₂-5);

ESI-MS: 323.2 [M+H]⁺; 321.1 [M−H]⁻.

Example 24

Synthesis of ethyl 2-methyl-7-[1,2-dihydro-5-fluoro-2-oxo-3H-indol-(Z)-3-ylidene]-4,5,6,7-tetrahydro-1H-indole-3-carboxylate (I-1)

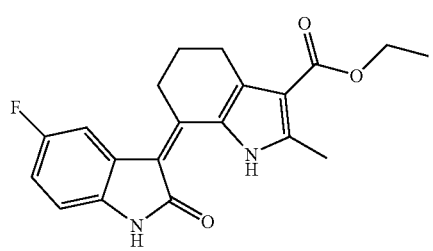

I-1

Similar procedure as Example 20, 5-fluoroindolin-2-one 0.39 g (2.6 mmol) and ethyl 2-methyl-7-oxo-4,5,6,7-tetrahydro-1H-indole-3-carboxylate (S3) 0.5 g (2.3 mmol) were reacted for 6 hours at 115 to 120° C., then the mixture was poured into ice water and extracted with CH₂Cl₂. The organic layer separated was washed with water and saturated sodium chloride solution, then dried over anhydrous Na₂SO₄ and concentrated in vacuo. The residue was purified by a silica gel column, eluted with CH₂Cl₂/EtOAc (4:1), to give 0.22 g (27%) of the titled compound as a yellow solid.

¹HNMR (500 MHz, CDCl₃) δ 14.36 (s, 1H, —NH-1), 7.74 (s, 1H, —NH-1'), 7.36 (d, 1H, J=10.53 Hz, H-4'), 6.86~6.79 (m, 2H, H-6', H-5'), 4.31 (q, 2H, —CH₂CH₃), 3.10 (t, 2H, —CH₂-4), 3.05 (t, 2H, —CH₂-6), 2.62 (s, 3H, —CH₃-2), 2.05 (m, 2H, —CH₂-5), 1.38 (t, 3H, —CH₂CH₃).

ESI-MS: 355.3 [M+H]⁺, 377.2 [M+Na]⁺; 353.2 [M−H]⁻.

Example 25

Synthesis of N-(2-(diethylamino)ethyl)-2-methyl-7-[1,2-dihydro-5-fluoro-2-oxo-3H-indol-(Z)-3-ylidene]-4,5,6,7-tetrahydro-1H-indole-3-carboxamide (I-2)

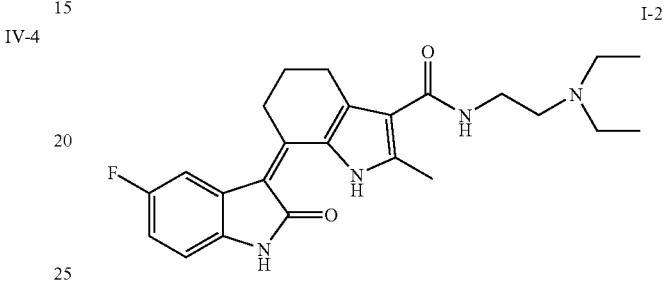

I-2

TiCl₄ 0.2 ml was added into a mixture of 5-fluoroindolin-2-one 0.12 g (0.79 mmol) and N-(2-(diethylamino)ethyl)-2-methyl-7-oxo-4,5,6,7-tetrahydro-1H-indole-3-carboxamide (II-1) 0.2 g (0.69 mmol) in 10 ml anhydrous pyridine. After stirred for 10 hours at 100 to 110° C., the mixture was poured into ice water and extracted with CH₂Cl₂. The organic layer separated was washed with water and saturated sodium chloride solution, then dried over anhydrous Na₂SO₄ and concentrated in vacuo. The residue was purified by a silica gel column, eluted with CH₂Cl₂/MeOH (30:1), to give 0.09 g (31%) of the titled compound as a yellow solid.

s¹HNMR (300 MHz, CDCl₃) δ 14.32 (s, 1H, —NH-1), 7.70 (s, 1H, —NH-1'), 7.36 (dd, 1H, J=10.62 Hz, H-4'), 6.91~6.78 (m, 2H, H-6', H-7'), 6.44 (bs, 1H, —CONH—), 3.51 (bs, 2H, —CONHCH₂CH₂—), 3.11 (t, 2H, —CH₂-4), 2.97 (t, 2H, —CH₂-6), 2.62 (bs, 9H, —CH₃-2, —NHCH₂CH₂N(CH₂CH₃)₂), 2.08 (m, 2H, —CH₂-5), 1.07 (bs, 6H, —(CH₂CH₃)₂);

ESI-MS: 425.1 [M+H]⁺.

Example 26

Synthesis of N-(2-(diethylamino)ethyl)-2-methyl-7-[1,2-dihydro-5-chloro-2-oxo-3H-indol-(Z)-3-ylidene]-4,5,6,7-tetrahydro-1H-indole-3-carboxamide (I-3)

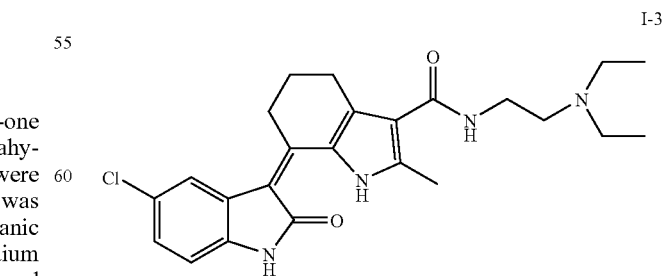

I-3

Similar procedure as Example 25, 5-chloroindolin-2-one 0.13 g (0.78 mmol) and N-(2-(diethylamino)ethyl)-2-methyl- 7-oxo-4,5,6,7-tetrahydro-1H-indole-3-carboxamide (II-1) 0.2 g (0.69 mmol) were reacted to give 0.08 g (26%) of the titled compound as a yellow solid.

¹HNMR (500 MHz, CDCl₃) δ 14.25 (s, 1H, —NH-1), 8.55 (s, 1H, —NH-1'), 7.55 (s, 1H, H-4'), 7.10 (dd, 1H, J=8.2 Hz, H-6'), 6.81 (d, 1H, J=8.2 Hz, H-7'), 6.48 (s, 1H, —CONH—), 3.51 (s, 2H, —CONHCH₂CH₂—), 3.06 (t, 2H, —CH₂-4), 2.89 (t, 2H, —CH₂-6), 2.68 (s, 2H, —CONHCH₂CH₂—), 2.60 (m, 7H, —CH₃-2, —NHCH₂CH₂N(CH₂CH₃)₂), 2.03 (m, 2H, —CH₂-5), 1.05 (t, 6H, —(CH₂CH₃)₂);

ESI-MS: 441.1 [M+H]⁺, 463.3[M+Na]⁺; 439.2 [M−H]⁻.

Example 27

Synthesis of N-(2-(diethylamino)ethyl)-2-methyl-7-[1,2-dihydro-5-methyl-2-oxo-3H-indol-(Z)-3-ylidene]-4,5,6,7-tetrahydro-1H-indole-3-carboxamide (I-4)

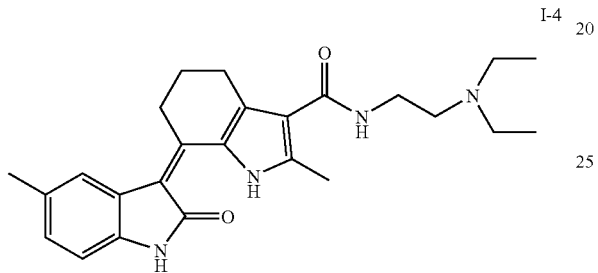

I-4

Similar procedure as Example 25, 5-methylindolin-2-one 0.12 g (0.82 mmol) and N-(2-(diethylamino)ethyl)-2-methyl-7-oxo-4,5,6,7-tetrahydro-1H-indole-3-carboxamide (II-1) 0.2 g (0.69 mmol) were reacted to give 0.09 g (31%) of the titled compound as a yellow solid.

¹HNMR (300 MHz, CDCl₃) δ 14.30 (s, 1H, —NH-1), 8.11 (s, 1H, —NH-1'), 7.42 (s, 1H, H-4'), 6.97 (d, 1H, J=7.92 Hz, H-6'), 6.80 (d, 1H, J=7.83 Hz, H-7'), 6.47 (bs, 1H, —CONH—), 3.51 (m, 2H, —CONHCH₂CH₂—), 3.14 (t, 2H, —CH₂-4), 2.94 (t, 2H, —CH₂-6), 2.68~2.57 (m, 9H, —CH₃-2,—NHCH₂CH₂N(CH₂CH₃)₂), 2.38 (s, 3H, —CH₃-5'), 2.03 (m, 2H, —CH₂-5), 1.05 (t, 6H, —(CH₂CH₃)₂);

ESI-MS: 421.1 [M+H]⁺.

Example 28

Synthesis of N-(2-(diethylamino)ethyl)-2-methyl-7-[1,2-dihydro-2-oxo-3H-indol-(Z)-3-ylidene]-4,5,6,7-tetrahydro-1H-indole-3-carboxamide (I-5)

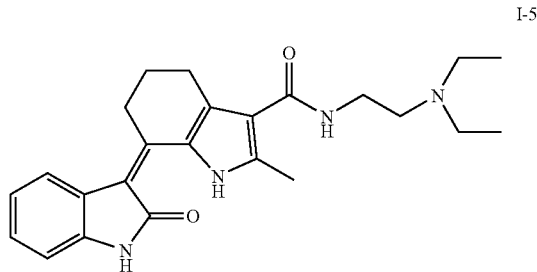

I-5

Similar procedure as Example 25, indolin-2-one 0.11 g (0.83 mmol) and N-(2-(diethylamino)ethyl)-2-methyl-7-oxo-4,5,6,7-tetrahydro-1H-indole-3-carboxamide (II-1) 0.2 g (0.69 mmol) were reacted to give 0.09 g (32%) of the titled compound as a yellow solid.

¹HNMR (300 MHz, CDCl₃) δ 14.27 (s, 1H, —NH-1), 8.06 (s, 1H, —NH-1'), 7.62 (s, 1H, J=7.71 Hz, H-4'), 7.15 (t, 1H, H-6'), 7.04 (t, 1H, H-5'), 6.91 (d, 1H, J=7.56 Hz, H-7'), 6.46 (bs, 1H, —CONH—), 3.51 (m, 2H, —CONHCH₂CH₂—), 3.15 (t, 2H, —CH₂-4), 2.93 (t, 2H, —CH₂-6), 2.67~2.59 (m, 9H, —CH₃-2, —NHCH₂CH₂N(CH₂CH₃)₂), 2.05 (m, 2H, —CH₂-5), 1.05 (t, 6H, —(CH₂CH₃)₂);

ESI-MS: 407.3 [M+H]⁺.

Example 29

Synthesis of N-(2-(dimethylamino)ethyl)-2-methyl-7-[1,2-dihydro-5-fluoro-2-oxo-3H-indol-(Z)-3-ylidene]-4,5,6,7-tetrahydro-1H-indole-3-carboxamide (I-6)

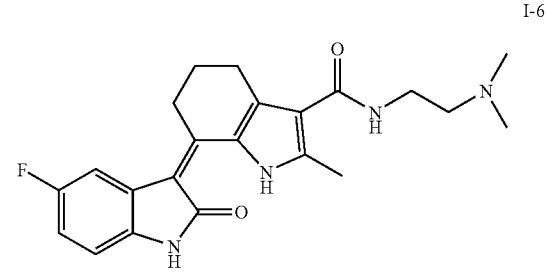

I-6

Similar procedure as Example 25, 5-fluoroindolin-2-one 0.13 g (0.86 mmol) and N-(2-(dimethylamino)ethyl)-2-methyl-7-oxo-4,5,6,7-tetrahydro-1H-indole-3-carboxamide (II-3) 0.18 g (0.68 mmol) were reacted to give 0.09 g (33%) of the titled compound as a yellow solid.

¹HNMR (300 MHz, CDCl₃) δ 14.21 (s, 1H, —NH-1), 8.70 (s, 1H, —NH-1'), 7.32 (d, 1H, J=12.07 Hz, H-4'), 6.87~6.76 (m, 2H, H-6', H-7'), 6.59 (bs, 1H, —CONH—), 3.57 (m, 2H, —CONHCH₂CH₂—), 2.99 (t, 2H, —CH₂-4), 2.76 (t, 2H, —CH₂-6), 2.65 (s, 2H, —NHCH₂CH₂N(CH₃)₂), 2.57 (s, 3H, —CH₃-2), 2.38 (s, 6H, —N(CH₃)₂), 1.94 (m, 2H, —CH₂-5);

ESI-MS: 397.3 [M+H]⁺.

Example 30

Synthesis of N-(3-(dimethylamino)propyl)-2-methyl-7-[1,2-dihydro-5-chloro-2-oxo-3H-indol-(Z)-3-ylidene]-4,5,6,7-tetrahydro-1H-indole-3-carboxamide (I-7)

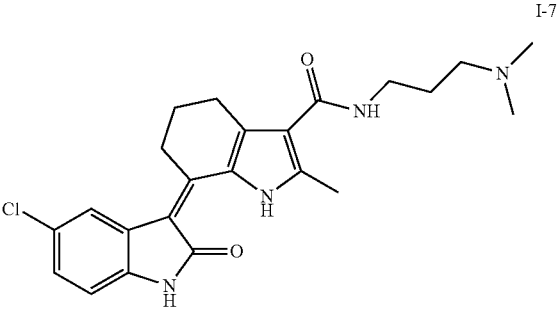

I-7

Similar procedure as Example 25, 5-chloroindolin-2-one 0.13 g (0.78 mmol) and N-(3-(dimethylamino)propyl)-2-methyl-7-oxo-4,5,6,7-tetrahydro-1H-indole-3-carboxamide (II-4) 0.2 g (0.72 mmol) were reacted to give 0.10 g (33%) of the titled compound as a yellow solid.

¹HNMR (300 MHz, CDCl₃) δ 14.25 (s, 1H, —NH-1), 7.83 (s, 1H, —NH-1'), 7.59 (s, 1H, H-4'), 7.12 (m, 2H, H-6', —CONH—), 6.83 (d, 1H, J=8.28 Hz, H-7'), 3.54 (s, 2H, —CONHCH₂CH₂CH₂—), 3.11 (s, 2H, —CH₂-4), 2.94 (s, 2H, —CH₂-6), 2.60 (s, 3H, —CH₃-2), 2.51 (s, 2H, —CONHCH₂CH₂CH₂—), 2.28 (s, 6H, —N(CH₃)₂), 2.07 (m, 2H, —CH₂-5), 1.79 (bs, 2H, —CONHCH₂CH₂CH₂—);
ESI-MS: 427.2 [M+H]⁺.

Example 31

Synthesis of N-(2-hydroxyethyl)-2-methyl-7-[1,2-dihydro-2-oxo-3H-indol-(Z)-3-ylidene]-4,5,6,7-tetrahydro-1H-indole-3-carboxamide (I-8)

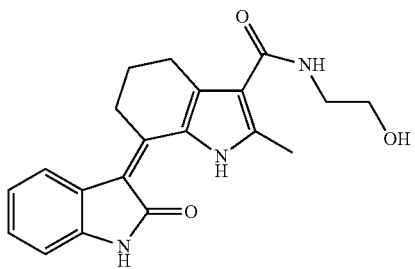

I-8

Similar procedure as Example 25, indolin-2-one 0.11 g (0.83 mmol) and N-(2-hydroxyethyl)-2-methyl-7-oxo-4,5,6,7-tetrahydro-1H-indole-3-carboxamide 0.17 g (0.72 mmol) were reacted to give 0.07 g (28%) of the titled compound as a yellow solid.
¹HNMR (300 MHz, CDCl₃) δ 14.49 (s, 1H, —NH-1), 10.83 (s, 1H, —NH-1'), 7.64 (d, 1H, J=7.83 Hz, H-4'), 7.26 (t, 1H, —CONH—), 7.13 (t, 1H, H-6'), 7.01~6.91 (m, 2H, H-5', H-7'), 4.65 (bs, 1H, —OH), 3.51 (s, 2H, —CONHCH₂CH₂—), 3.31 (m, 2H, —CONHCH₂CH₂—), 3.13 (t, 2H, —CH₂-4), 2.84 (t, 2H, —CH₂-6), 2.46 (s, 3H, —CH₃-2), 1.99 (m, 2H, —CH₂-5);
ESI-MS: 352.3 [M+H]⁺, 374.1[M+Na]⁺; 350.2 [M–H]⁻.

Example 32

Synthesis of N-(2-hydroxyethyl)-2-methyl-7-[1,2-dihydro-5-fluoro-2-oxo-3H-indol-(Z)-3-ylidene]-4,5,6,7-tetrahydro-1H-indole-3-carboxamide (I-9)

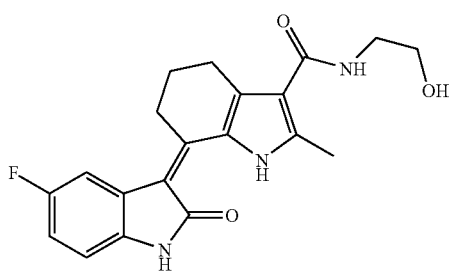

I-9

Similar procedure as Example 25, 5-fluoroindolin-2-one 0.13 g (0.86 mmol) and N-(2-hydroxyethyl)-2-methyl-7-oxo-4,5,6,7-tetrahydro-1H-indole-3-carboxamide (II-2) 0.17 g (0.72 mmol) were reacted to give 0.08 g (30%) of the titled compound as a yellow solid.
¹HNMR (300 MHz, CDCl₃) δ 14.54 (s, 1H, —NH-1), 10.84 (s, 1H, —NH-1'), 7.44 (dd, 1H, J=10.9 Hz, H-4'), 7.26 (t, 1H, —CONH—), 6.98~6.85 (m, 2H, H-6', H-7'), 4.63 (t, 1H, —OH), 3.52 (q, 2H, —CONHCH₂CH₂—), 3.32 (m, 2H, —CONHCH₂CH₂—), 3.08 (t, 2H, —CH₂-4), 2.85 (t, 2H, —CH₂-6), 2.47 (s, 3H, —CH₃-2), 1.98 (m, 2H, —CH₂-5);
ESI-MS: 368.1 [M–H]⁻.

Example 33

Synthesis of 2-methyl-3-(morpholine-4-carbonyl)-7-[1,2-dihydro-5-fluoro-2-oxo-3H-indol-(Z)-3-ylidene]-4,5,6,7-tetrahydro-1H-indole (I-10)

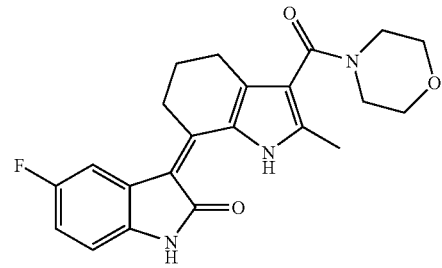

I-10

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.15 g (0.46 mmol) and morpholine 0.13 g (1.5 mmol) were reacted to give 0.12 g (66%) of the titled compound as a yellow solid.
¹HNMR (300 MHz, CDCl₃) δ 14.23 (s, 1H, —NH-1), 7.95 (s, 1H, —NH-1'), 7.35 (dd, 1H, J=10.58 Hz, H-4'), 6.88~6.77 (m, 2H, H-6', H-7'), 3.69 (s, 4H, —N(CH₂CH₂)₂O), 3.63 (s, 4H, —N(CH₂CH₂)₂O), 3.09 (t, 2H, —CH₂-4), 2.70 (t, 2H, —CH₂-6), 2.42 (s, 3H, —CH₃-2), 2.06 (m, 2H, —CH₂-5);
ESI-MS: 396.2 [M+H]⁺, 418.2[M+Na]⁺, 434.0[M+K]⁺; 394.2[M–H]⁻.

Example 34

Synthesis of 2-methyl-3-(morpholine-4-carbonyl)-7-[1,2-dihydro-5-chloro-2-oxo-3H-indol-(Z)-3-ylidene]-4,5,6,7-tetrahydro-1H-indole (I-11)

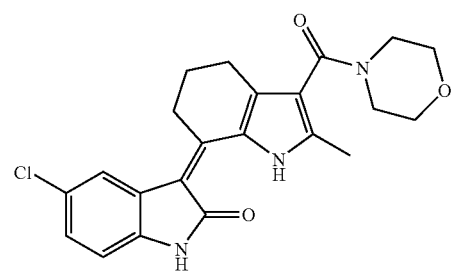

I-11

Similar procedure as Example 2, 2-methyl-7-[1,2-dihydro-5-chloro-2-oxo-3H-indol-(Z)-3-ylidene]-4,5,6,7-tetrahydro-1H-indole-3-carboxylic acid (IV-3) 0.15 g (0.44 mmol) and morpholine 0.12 g (1.4 mmol) were reacted to give 0.13 g (72%) of the titled compound as a yellow solid.
¹HNMR (500 MHz, CDCl₃) δ 14.19 (s, 1H, —NH-1), 7.90 (s, 1H, —NH-1'), 7.59 (s, 1H, H-4'), 7.12 (dd, 1H, J=8.19 Hz, H-6'), 6.82 (d, 1H, J=8.23 Hz, H-7'), 3.70 (s, 4H, —N(CH₂CH₂)₂O), 3.63 (s, 4H, —N(CH₂CH₂)₂O), 3.12 (s, 2H, —CH₂-4), 2.71 (s, 2H, —CH₂-6), 2.43 (s, 3H, —CH₃-2), 2.06 (m, 2H, —CH₂-5);
ESI-MS: 412.2 [M+H]⁺, 434.1[M+Na]⁺; 410.2[M–H]⁻.

Example 35

Synthesis of 2-methyl-3-(morpholine-4-carbonyl)-7-[1,2-dihydro-2-oxo-3H-indol-(Z)-3-ylidene]-4,5,6,7-tetrahydro-1H-indole (I-12)

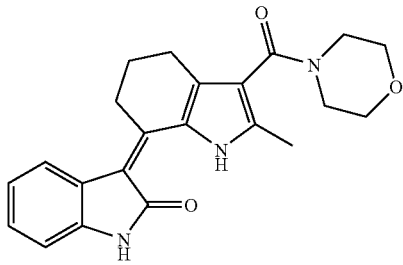

I-12

Similar procedure as Example 2, 2-methyl-7-[1,2-dihydro-2-oxo-3H-indol-(Z)-3-ylidene]-4,5,6,7-tetrahydro-1H-indole-3-carboxylic acid (IV-1) 0.14 g (0.45 mmol) and morpholine 0.13 g (1.5 mmol) were reacted to give 0.12 g (71%) of the titled compound as a yellow solid.

$^1$HNMR (300 MHz, CDCl$_3$) δ 14.20 (s, 1H, —NH-1), 8.07 (s, 1H, —NH-1'), 7.63 (d, 1H, J=7.86 Hz, H-4'), 7.16 (t, 1H, H-6'), 7.05 (t, 1H, H-5'), 6.90 (dd, 1H, J=7.63 Hz, H-7'), 3.70 (s, 4H, —N(CH$_2$CH$_2$)$_2$O), 3.64 (s, 4H, —N(CH$_2$CH$_2$)$_2$O), 3.15 (t, 2H, —CH$_2$-4), 2.70 (s, 2H, —CH$_2$-6), 2.42 (s, 3H, —CH$_3$-2), 2.05 (m, 2H, —CH$_2$-5);

ESI-MS: 378.1 [M+H]$^+$; 376.2[M−H]$^-$.

Example 36

Synthesis of 2-methyl-3-(4-methylpiperazine-1-carbonyl)-7-[1,2-dihydro-2-oxo-3H-indol-(Z)-3-ylidene]-4,5,6,7-tetrahydro-1H-indole (I-13)

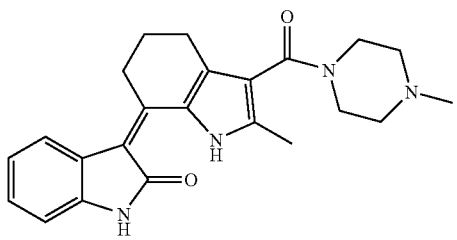

I-13

Similar procedure as Example 2, 2-methyl-7-[1,2-dihydro-2-oxo-3H-indol-(Z)-3-ylidene]-4,5,6,7-tetrahydro-1H-indole-3-carboxylic acid (IV-1) 0.15 g (0.49 mmol) and 1-methylpiperazine 0.15 g (1.5 mmol) were reacted to give 0.14 g (73%) of the titled compound as a yellow solid.

$^1$HNMR (300 MHz, CDCl$_3$) δ 14.17 (s, 1H, —NH-1), 7.90 (s, 1H, —NH-1'), 7.64 (d, 1H, J=7.83 Hz, H-4'), 7.15 (t, 1H, H-6'), 7.05 (t, 1H, H-5'), 6.91 (d, 1H, J=7.60 Hz, H-7'), 3.65 (s, 4H, —N(CH$_2$CH$_2$)$_2$NCH$_3$), 3.16 (t, 2H, —CH$_2$-4), 2.70 (s, 2H, —CH$_2$-6), 2.41 (s, 7H, —CH$_3$-2, —N(CH$_2$CH$_2$)$_2$NCH$_3$), 2.33 (s, 3H, —N(CH$_2$CH$_2$)$_2$NCH$_3$), 2.06 (m, 2H, —CH$_2$-5);

ESI-MS: 391.2 [M+H]$^+$; 389.2[M−H]$^-$.

Example 37

Synthesis of 2-methyl-3-(4-methylpiperazine-1-carbonyl)-7-[1,2-dihydro-5-fluoro-2-oxo-3H-indol-(Z)-3-ylidene]-4,5,6,7-tetrahydro-1H-indole (I-14)

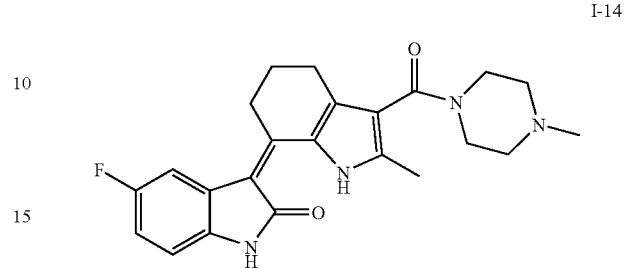

I-14

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.15 g (0.46 mmol) and 1-methylpiperazine 0.15 g (1.5 mmol) were reacted to give 0.14 g (75%) of the titled compound as a yellow solid.

$^1$HNMR (300 MHz, CDCl$_3$) δ 14.21 (s, 1H, —NH-1), 7.70 (s, 1H, —NH-1'), 7.36 (dd, 1H, J=10.61 Hz, H-4'), 6.89~6.78 (m, 2H, H-6', H-7'), 3.66 (bs, 4H, —N(CH$_2$CH$_2$)$_2$NCH$_3$), 3.11 (t, 2H, —CH$_2$-4), 2.71 (s, 2H, —CH$_2$-6), 2.42 (s, 7H, —CH$_3$-2, —N(CH$_2$CH$_2$)$_2$NCH$_3$), 2.35 (s, 3H, —N(CH$_2$CH$_2$)$_2$NCH$_3$), 2.06 (m, 2H, —CH$_2$-5);

ESI-MS: 409.3 [M+H]$^+$; 407.3[M−H]$^-$.

Example 38

Synthesis of N,N,2-trimethyl-7-[1,2-dihydro-2-oxo-3H-indol-(Z)-3-ylidene]-4,5,6,7-tetrahydro-1H-indole-3-carboxamide (I-15)

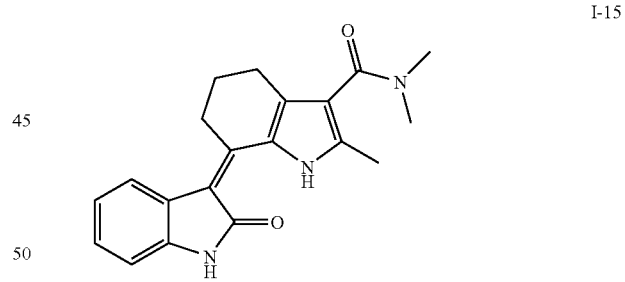

I-15

Similar procedure as Example 2, 2-methyl-7-[1,2-dihydro-2-oxo-3H-indol-(Z)-3-ylidene]-4,5,6,7-tetrahydro-1H-indole-3-carboxylic acid (IV-1) 0.10 g (0.32 mmol), dimethylamine hydrochloride 0.12 g (1.5 mmol) and DBU 0.23 g (1.5 mmol) were reacted to give 50 mg (47%) of the titled compound as a yellow solid.

$^1$HNMR (500 MHz, CDCl$_3$) δ 14.14 (s, 1H, —NH-1), 7.85 (bs, 1H, —NH-1'), 7.63 (s, 1H, J=7.90 Hz, H-4'), 7.15 (t, 1H, H-6'), 7.04 (t, 1H, H-5'), 6.90 (d, 1H, J=7.64 Hz, H-7'), 3.16 (s, 2H, —CH$_2$-4), 3.06 (s, 3H, —NCH$_3$(CH$_3$)), 2.71 (s, 2H, —CH$_2$-6), 2.40 (s, 3H, —CH$_3$-2), 2.04 (m, 2H, —CH$_2$-5), 1.57 (s, 3H, —NCH$_3$ (CH$_3$));

ESI-MS: 336.1 [M+H]$^+$; 334.2 [M−H]$^-$.

Example 39

Synthesis of N-(2-morpholinoethyl)-2-methyl-7-[1,2-dihydro-5-methyl-2-oxo-3H-indol-(Z)-3-ylidene]-4,5,6,7-tetrahydro-1H-indole-3-carboxamide (I-16)

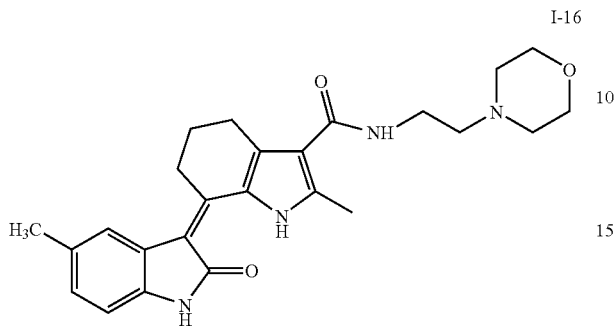

Similar procedure as Example 25, 5-methylindolin-2-one 0.12 g (0.82 mmol) and 2-methyl-N-(2-morpholinoethyl)-7-oxo-4,5,6,7-tetrahydro-1H-indole-3-carboxamide (II-5) 0.21 g (0.69 mmol) were reacted to give 0.10 g (33%) of the titled compound as a yellow solid.

$^1$HNMR (300 MHz, CDCl$_3$) δ 14.34 (s, 1H, —NH-1), 7.70 (s, 1H, —NH-1'), 7.45 (s, 1H, H-4'), 6.99 (d, 1H, J=7.71 Hz, H-6'), 6.82 (d, 1H, J=7.83 Hz, H-7'), 6.35 (bs, 1H, —CONH—), 3.75 (s, 4H, —CH$_2$N(CH$_2$CH$_2$)$_2$O), 3.56 (s, 2H, —CONHCH$_2$), 3.16 (s, 2H, —CH$_2$-4), 2.99 (s, 2H, —CH$_2$-6), 2.63~2.55 (m, 9H, —CH$_3$-2, —CH$_2$N(CH$_2$CH$_2$)$_2$O), 2.40 (s, 3H, —CH$_3$-6'), 2.07 (m, 2H, —CH$_2$-5);

ESI-MS: 435.2 [M+H]$^+$; 457.2 [M+Na]$^+$; 473.2 [M+K]$^+$.

Example 40

Synthesis of N-(2-morpholinoethyl)-2-methyl-7-[1,2-dihydro-5-methyl-2-oxo-3H-indol-(Z)-3-ylidene]-4,5,6,7-tetrahydro-1H-indole-3-carboxamide (I-17)

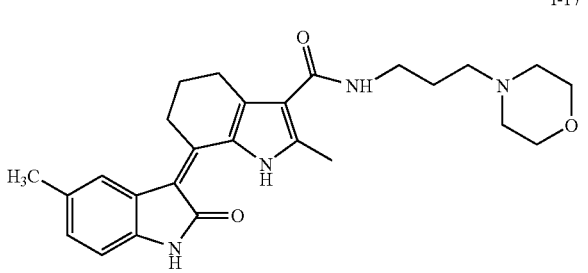

Similar procedure as Example 25, 5-methylindolin-2-one 0.15 g (1.02 mmol) and 2-methyl-N-(3-morpholinopropyl)-7-oxo-4,5,6,7-tetrahydro-1H-indole-3-carboxamide (II-8) 0.27 g (0.85 mmol) were reacted to give 0.13 g (34%) of the titled compound as a yellow solid.

$^1$HNMR (300 MHz, CDCl$_3$) δ 14.32 (s, 1H, —NH-1), 7.70 (s, 1H, —NH-1'), 7.45 (s, 1H, H-4'), 6.99 (d, 1H, J=7.26 Hz, H-6'), 6.82 (d, 1H, J=7.80 Hz, H-7'), 6.18 (bs, 1H, —CONH—), 3.71 (bs, 4H, —CH$_2$N(CH$_2$CH$_2$)$_2$O), 3.57 (m, 2H, —CONHCH$_2$), 3.19 (t, 2H, —CH$_2$-4), 2.97 (t, 2H, —CH$_2$-6), 2.61 (s, 3H, —CH$_3$-2), 2.49 (bs, 6H, —CH$_2$N(CH$_2$CH$_2$)$_2$O), 2.40 (s, 3H, —CH$_3$-6'), 2.13 (m, 2H, —CH$_2$-5), 1.82 (s, 2H, —CH$_2$CH$_2$N(CH$_2$CH$_2$)$_2$O);

ESI-MS: 449.2 [M+H]$^+$; 471.2 [M+Na]$^+$.

Example 41

Synthesis of N-(2-morpholinoethyl)-2-methyl-7-[1,2-dihydro-2-oxo-3H-indol-(Z)-3-ylidene]-4,5,6,7-tetrahydro-1H-indole-3-carboxamide (I-18)

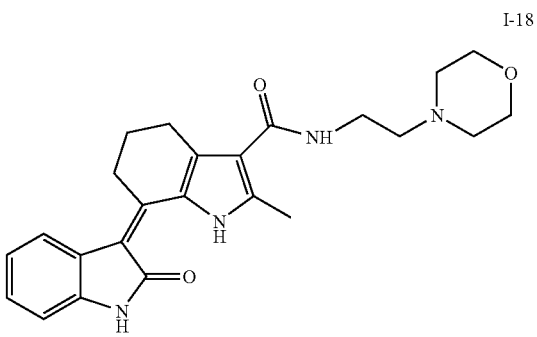

Similar procedure as Example 25, indolin-2-one 0.11 g (0.83 mmol) and 2-methyl-N-(2-morpholino ethyl)-7-oxo-4,5,6,7-tetrahydro-1H-indole-3-carboxamide (II-5) 0.20 g (0.65 mmol) were reacted to give 0.10 g (37%) of the titled compound as a yellow solid.

$^1$HNMR (300 MHz, CDCl$_3$) δ 14.33 (s, 1H, —NH-1), 7.87 (s, 1H, —NH-1'), 7.64 (d, 1H, J=7.89 Hz, H-4'), 7.17 (t, 1H, H-6'), 7.09 (t, 1H, H-5'), 6.94 (d, 1H, J=7.09 Hz, H-7'), 6.34 (bs, 1H, —CONH—), 3.77 (bs, 4H, —CH$_2$N(CH$_2$CH$_2$)$_2$O), 3.58 (bs, 2H, —CONHCH$_2$), 3.19 (t, 2H, —CH$_2$-4), 2.97 (s, 2H, —CH$_2$-6), 2.63~2.56 (m, 9H, —CH$_3$-2, —CH$_2$N(CH$_2$CH$_2$)$_2$O), 2.09 (m, 2H, —CH$_2$-5);

ESI-MS: 421.2 [M+H]$^+$; 443.2 [M+Na]$^+$.

Example 42

Synthesis of N-(2-morpholinoethyl)-2-methyl-7-[1,2-dihydro-5-chloro-2-oxo-3H-indol-(Z)-3-ylidene]-4,5,6,7-tetrahydro-1H-indole-3-carboxamide (I-19)

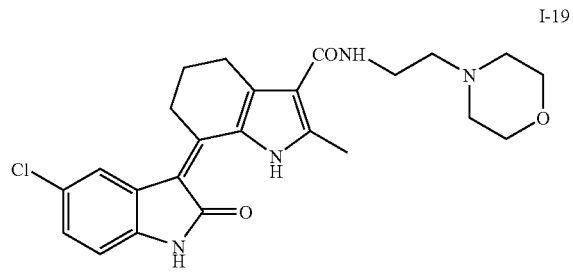

Similar procedure as Example 25, 5-chloroindolin-2-one 0.15 g (0.90 mmol) and 2-methyl-N-(2-morpholino ethyl)-7-oxo-4,5,6,7-tetrahydro-1H-indole-3-carboxamide (II-5) 0.23 g (0.75 mmol) were reacted to give 0.11 g (32%) of the titled compound as a yellow solid.

$^1$HNMR (300 MHz, CDCl$_3$) δ 14.29 (s, 1H, —NH-1), 7.80 (bs, 1H, —NH-1'), 7.62 (s, 1H, H-4'), 7.15 (dd, 1H, J=8.15 Hz, H-6'), 6.83 (d, 1H, J=8.19 Hz, H-7'), 6.35 (bs, 1H, —CONH—), 3.74 (s, 4H, —CH$_2$N(CH$_2$CH$_2$)$_2$O), 3.56 (s, 2H, —CONHCH$_2$), 3.13 (t, 2H, —CH$_2$-4), 2.98 (t, 2H,

—CH$_2$-6), 2.63~2.55 (m, 9H, —CH$_3$-2, —CH$_2$N(CH$_2$CH$_2$)$_2$O), 2.12 (m, 2H, —CH$_2$-5);

ESI-MS: 455.1 [M+H]$^+$.

Example 43

Synthesis of N-(2-morpholinoethyl)-2-methyl-7-[1,2-dihydro-5-fluoro-2-oxo-3H-indol-(Z)-3-ylidene]-4,5,6,7-tetrahydro-1H-indole-3-carboxamide (I-20)

I-20

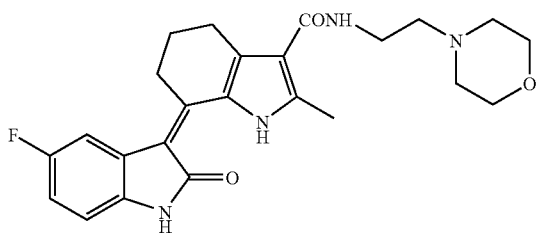

Similar procedure as Example 25, 5-fluoroindolin-2-one 0.15 g (1.0 mmol) and 2-methyl-N-(2-morpholino ethyl)-7-oxo-4,5,6,7-tetrahydro-1H-indole-3-carboxamide (II-5) 0.23 g (0.75 mmol) were reacted to give 0.12 g (36%) of the titled compound as a yellow solid.

$^1$HNMR (300 MHz, CDCl$_3$) δ 14.40 (s, 1H, —NH-1), 7.73 (bs, 1H, —NH-1'), 7.42 (dd, 1H, J=10.6 Hz, H-4'), 6.95 (m, 2H, H-6', H-7'), 6.37 (bs, 1H, —CONH—), 3.78 (m, 4H, —CH$_2$N(CH$_2$CH$_2$)$_2$O), 3.58 (s, 2H, —CONHCH$_2$), 3.19 (t, 2H, —CH$_2$-4), 3.04 (t, 2H, —CH$_2$-6), 2.67~2.51 (m, 9H, —CH$_3$-2, —CH$_2$N(CH$_2$CH$_2$)$_2$O), 2.16 (m, 2H, —CH$_2$-5);

ESI-MS: 439.2 [M+H]$^+$; 461.2 [M+Na]$^+$.

Example 44

Synthesis of N-(3-morpholinopropyl)-2-methyl-7-[1,2-dihydro-5-fluoro-2-oxo-3H-indol-(Z)-3-ylidene]-4,5,6,7-tetrahydro-1H-indole-3-carboxamide (I-21)

I-21

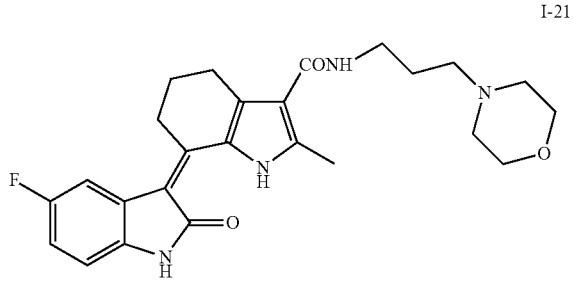

Similar procedure as Example 25, 5-fluoroindolin-2-one 0.15 g (1.0 mmol) and 2-methyl-N-(3-morpholinopropyl)-7-oxo-4,5,6,7-tetrahydro-1H-indole-3-carboxamide (II-8) 0.23 g (0.75 mmol) were reacted to give 0.11 g (30%) of the titled compound as a yellow solid.

$^1$HNMR (300 MHz, CDCl$_3$) δ 7.65 (s, 1H, —NH-1'), 7.29 (d, 1H, J=9.2 Hz, H-4'), 6.82~6.72 (m, 2H, H-6', H-7'), 6.15 (bs, 1H, —CONH—), 3.62 (s, 4H, —CH$_2$N(CH$_2$CH$_2$)$_2$O), 3.46 (m, 2H, —CONHCH$_2$), 3.05 (t, 2H, —CH$_2$-4), 2.87 (t, 2H, —CH$_2$-6), 2.53 (s, 3H, —CH$_3$-2), 2.49 (bs, 6H, —CH$_2$CH$_2$N(CH$_2$CH$_2$)$_2$O), 2.01 (m, 2H, —CH$_2$-5), 1.76 (s, 2H, —CH$_2$CH$_2$N(CH$_2$CH$_2$)$_2$O);

ESI-MS: 453.2 [M+H]$^+$; 475.2 [M+Na]$^+$; 491.2 [M+K]$^+$.

Example 45

Synthesis of N-(3-morpholinopropyl)-2-methyl-7-[1,2-dihydro-5-bromo-2-oxo-3H-indol-(Z)-3-ylidene]-4,5,6,7-tetrahydro-1H-indole-3-carboxamide (I-22)

I-22

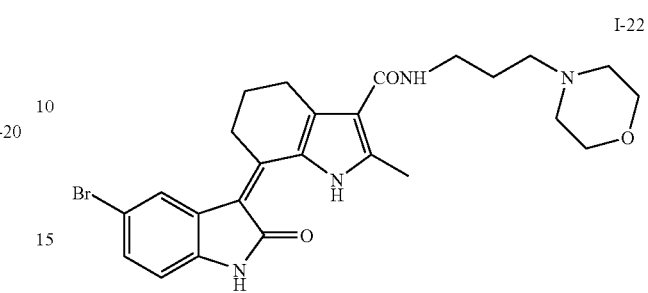

Similar procedure as Example 25, 5-bromoindolin-2-one 0.21 g (1.0 mmol) and 2-methyl-N-(3-morpholinopropyl)-7-oxo-4,5,6,7-tetrahydro-1H-indole-3-carboxamide (II-8) 0.26 g (0.81 mmol) were reacted to give 0.10 g (24%) of the titled compound as a yellow solid.

$^1$HNMR (300 MHz, CDCl$_3$) δ 14.27 (s, 1H, —NH-1), 7.76~7.72 (d, 2H, —NH-1', H-4'), 7.27 (m, 1H, H-6'), 6.80 (d, 1H, J=8.21 Hz, H-7'), 6.24 (bs, 1H, —CONH—), 3.70 (bs, 4H, —CH$_2$N(CH$_2$CH$_2$)$_2$O), 3.56 (m, 2H, —CONHCH$_2$), 3.13 (t, 2H, —CH$_2$-4), 2.95 (t, 2H, —CH$_2$-6), 2.60 (s, 3H, —CH$_3$-2), 2.50 (bs, 6H, —CH$_2$CH$_2$N(CH$_2$CH$_2$)$_2$O), 2.10 (m, 2H, —CH$_2$-5), 1.83 (s, 2H, —CH$_2$CH$_2$CH$_2$—);

ESI-MS: 514.2 [M+H]$^+$.

Example 46

Synthesis of N-(2-morpholinoethyl)-2-methyl-7-[1,2-dihydro-7-fluoro-2-oxo-3H-indol-(Z)-3-ylidene]-4,5,6,7-tetrahydro-1H-indole-3-carboxamide (I-23)

I-23

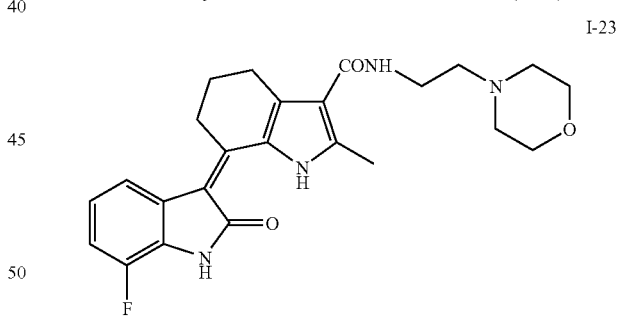

Similar procedure as Example 25, 7-fluoroindolin-2-one 0.15 g (1.0 mmol) and 2-methyl-N-(2-morpholinoethyl)-7-oxo-4,5,6,7-tetrahydro-1H-indole-3-carboxamide (II-5) 0.23 g (0.75 mmol) were reacted to give 0.11 g (33%) of the titled compound as a yellow solid.

$^1$HNMR (300 MHz, DMSO-d$_6$) δ 14.47 (s, 1H, —NH-1), 11.37 (s, 1H, —NH-1'), 7.47 (d, 1H, J=7.2 Hz, H-4'), 7.32 (t, 1H, —CONH—), 7.01 (m, 2H, H-5', H-6'), 3.58 (t, 4H, —CH$_2$N(CH$_2$CH$_2$)$_2$O), 3.31 (q, 2H, —CONHCH$_2$), 3.11 (t, 2H, —CH$_2$-4), 2.85 (t, 2H, —CH$_2$-6), 2.51 (m, 5H, —CH$_3$-2, —CONHCH$_2$CH$_2$—), 2.42 (m, 4H, —CH$_2$N(CH$_2$CH$_2$)$_2$O), 1.96 (m, 2H, —CH$_2$-5);

ESI-MS: 439.2 [M+H]$^+$; 461.2 [M+Na]$^+$.

Example 47

Synthesis of N-(2-(pyrrolidin-1-yl)ethyl)-2-methyl-7-[1,2-dihydro-2-oxo-3H-indol-(Z)-3-ylidene]-4,5,6,7-tetrahydro-1H-indole-3-carboxamide (I-24)

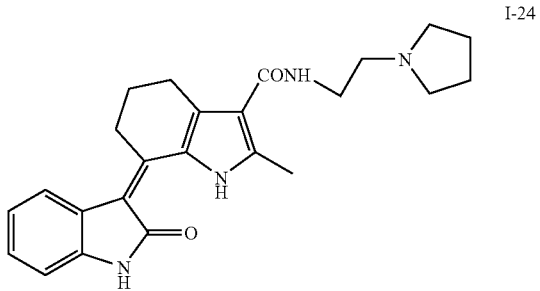

I-24

Similar procedure as Example 25, indolin-2-one 0.15 g (1.12 mmol) and 2-methyl-7-oxo-N-(2-(pyrrolidin-4,5,6,7-tetrahydro-1H-indole-3-carboxamide (II-7) 0.26 g (0.90 mmol) were reacted to give 0.15 g (41%) of the titled compound as a yellow solid.

$^1$HNMR (300 MHz, CDCl$_3$) δ 14.16 (s, 1H, —NH-1), 8.90 (s, 1H, —NH-1'), 7.60 (d, 1H, J=7.75 Hz, H-4'), 7.16 (t, 1H, H-6'), 7.07 (t, 1H, H-5'), 6.90 (dd, 1H, J=7.58 Hz, H-7'), 6.61 (bs, 1H, —CONH—), 3.61 (d, 2H, J=4.29 Hz, —CONHCH$_2$), 3.03 (t, 2H, —CH$_2$-4), 2.82 (s, 2H, —CH$_2$-6), 2.70 (s, 6H, —CH$_2$N(CH$_2$CH$_2$)$_2$), 2.57 (s, 3H, —CH$_3$-2), 1.95~1.85 (m, 6H, —CH$_2$N(CH$_2$CH$_2$)$_2$, —CH$_2$-5);

ESI-MS: 405.2 [M+H]$^+$; 427.2 [M+Na]$^+$.

Example 48

Synthesis of N-(2-(piperidin-1-yl)ethyl)-2-methyl-7-[1,2-dihydro-2-oxo-3H-indol-(Z)-3-ylidene]-4,5,6,7-tetrahydro-1H-indole-3-carboxamide (I-25)

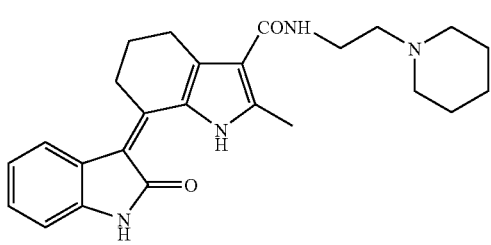

I-25

Similar procedure as Example 25, indolin-2-one 0.15 g (1.12 mmol) and 2-methyl-7-oxo-N-(2-(piperidin-1-yl)ethyl)-4,5,6,7-tetrahydro-1H-indole-3-carboxamide (II-6) 0.27 g (0.90 mmol) were reacted to give 0.14 g (37%) of the titled compound as a yellow solid.

$^1$HNMR (300 MHz, DMSO-d$_6$) δ 14.51 (s, 1H, —NH-1), 10.89 (s, 1H, —NH-1'), 7.64 (d, 1H, J=7.85 Hz, H-4'), 7.21 (t, 1H, —CONH—), 7.12 (t, 1H, H-6'), 6.97 (t, 1H, H-5'), 6.92 (d, 1H, J=7.53 Hz, H-7'), 3.32 (m, 2H, —CONHCH$_2$), 3.10 (t, 2H, —CH$_2$-4), 2.84 (t, 2H, —CH$_2$-6), 2.46 (s, 3H, —CH$_3$-2), 2.40 (m, 6H, —CH$_2$N(CH$_2$CH$_2$)$_2$CH$_2$), 1.94 (m, 2H, —CH$_2$-5); 1.51 (m, 4H, —CH$_2$N(CH$_2$CH$_2$)$_2$CH$_2$); 1.39 (m, 2H, —CH$_2$N(CH$_2$CH$_2$)$_2$CH$_2$);

ESI-MS: 419.2 [M+H]$^+$.

Example 49

Synthesis of N-(2-(piperidin-1-yl)ethyl)-2-methyl-7-[1,2-dihydro-5-fluoro-2-oxo-3H-indol-(Z)-3-ylidene]-4,5,6,7-tetrahydro-1H-indole-3-carboxamide (I-26)

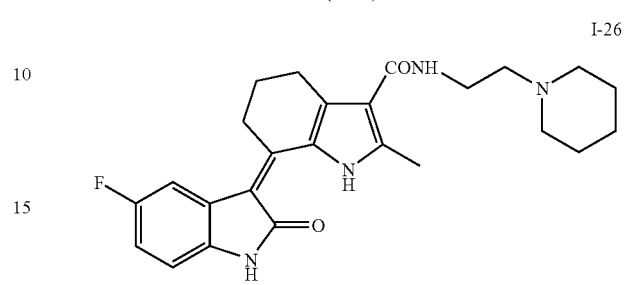

I-26

Similar procedure as Example 25, 5-fluoroindolin-2-one 0.15 g (1.0 mmol) and 2-methyl-7-oxo-N-(2-(piperidin-1-yl)ethyl)-4,5,6,7-tetrahydro-1H-indole-3-carboxamide (II-6) 0.24 g (0.80 mmol) were reacted to give 0.14 g (40%) of the titled compound as a yellow solid.

$^1$HNMR (300 MHz, CDCl$_3$) δ 8.32 (s, 1H, —NH-1'), 7.27 (d, 1H, J=10.7 Hz, H-4'), 6.81~6.70 (m, 2H, H-6', H-7'), 6.47 (bs, 1H, —CONH—), 3.48 (q, 2H, —CONHCH$_2$CH$_2$—), 2.98 (t, 2H, —CH$_2$-4), 2.81 (t, 2H, —CH$_2$-6), 2.53~2.41 (m, 9H, —CH$_3$-2, —NHCH$_2$CH$_2$N(CH$_2$CH$_2$)$_2$CH$_2$), 1.94 (m, 2H, —CH$_2$-5), 1.53 (s, 6H, —N(CH$_2$CH$_2$)$_2$CH$_2$);

ESI-MS: 437.2 [M+H]$^+$; 459.2 [M+Na]$^+$.

Example 50

Synthesis of N-(2-(pyrrolidin-1-yl)ethyl)-2-methyl-7-[1,2-dihydro-5-fluoro-2-oxo-3H-indol-(Z)-3-ylidene]-4,5,6,7-tetrahydro-1H-indole-3-carboxamide (I-27)

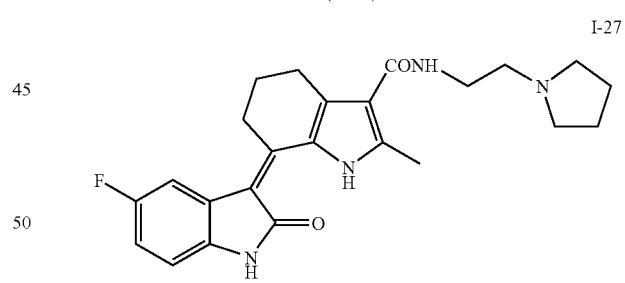

I-27

Similar procedure as Example 25, 5-fluoroindolin-2-one 0.15 g (1.0 mmol) and 2-methyl-7-oxo-N-(2-(pyrrolidin-1-yl)ethyl)-4,5,6,7-tetrahydro-1H-indole-3-carboxamide (II-7) 0.23 g (0.80 mmol) were reacted to give 0.12 g (35%) of the titled compound as a yellow solid.

$^1$HNMR (300 MHz, DMSO-d$_6$) δ 14.53 (s, 1H, —NH-1), 10.90 (s, 1H, —NH-1'), 7.42 (m, 2H, —CONH—, H-4'), 6.92~6.82 (m, 2H, H-6', H-7'), 3.37 (q, 2H, —CONHCH$_2$), 3.06 (t, 2H, —CH$_2$-4), 2.81 (t, 2H, —CH$_2$-6), 2.70 (s, 6H, —CH$_2$N(CH$_2$CH$_2$)$_2$), 2.43 (s, 3H, —CH$_3$-2), 1.91 (m, 2H, —CH$_2$-5), 1.72 (s, 4H, —CH$_2$N(CH$_2$CH$_2$);

ESI-MS: 423.1 [M+H]$^+$; 445.1 [M+Na]$^+$.

Example 51

Synthesis of N-(3-(pyrrolidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide (I-28)

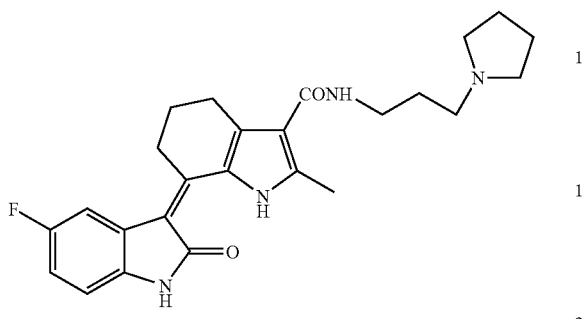

I-28

Similar procedure as Example 25, 5-fluoroindolin-2-one 0.15 g (1.0 mmol) and 2-methyl-7-oxo-N-(3-(pyrrolidin-1-yl)propyl)-4,5,6,7-tetrahydro-1H-indole-3-carboxamide (II-10) 0.23 g (0.75 mmol) were reacted to give 0.10 g (31%) of the titled compound as a yellow solid.

$^1$HNMR (300 MHz, DMSO-$d_6$) δ 14.55 (s, 1H, —NH-1), 10.91 (s, 1H, —NH-1'), 7.51 (t, 1H, —CONH—), 7.46 (dd, 1H, J=10.87 Hz, H-4'), 6.95 (t, 1H, H-6'), 6.89 (dd, 1H, J=8.5 Hz, H-7'), 3.28 (q, 2H, —CONHCH$_2$), 3.09 (t, 2H, —CH$_2$-4), 2.84 (t, 2H, —CH$_2$-6), 2.50~2.45 (m, 9H, —CH$_3$-2, —CH$_2$N(CH$_2$CH$_2$)$_2$), 1.96 (m, 2H, —CH$_2$-5), 1.69 (m, 6H, —CH$_2$CH$_2$N(CH$_2$CH$_2$)$_2$);

ESI-MS: 437.2 [M+H]$^+$; 459.2 [M+Na]$^+$.

Example 52

Synthesis of N-(3-(4-methylpiperazin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide (I-29)

I-29

Similar procedure as Example 25, 5-fluoroindolin-2-one 0.15 g (1.0 mmol) and 2-methyl-N-(3-(4-methylpiperazin-1-yl)propyl)-7-oxo-4,5,6,7-tetrahydro-1H-indole-3-carboxamide (II-11) 0.27 g (0.81 mmol) were reacted to give 0.12 g (32%) of the titled compound as a yellow solid.

$^1$HNMR (300 MHz, DMSO-$d_6$) δ 14.54 (s, 1H, —NH-1), 10.91 (s, 1H, —NH-1'), 7.46 (m, 2H, —CONH—, H-4'), 6.95 (t, 1H, H-6'), 6.87 (dd, 1H, J=8.4 Hz, H-7'), 3.22 (q, 2H, —CONHCH$_2$CH$_2$—), 3.07 (t, 2H, —CH$_2$-4), 2.82 (t, 2H, —CH$_2$-6), 2.44 (s, 3H, CH$_3$-2), 2.34 (m, 10H, —CH$_2$N(CH$_2$CH$_2$)$_2$NCH$_3$), 2.14 (s, 3H, —NCH$_3$), 1.93 (m, 2H, —CH$_2$-5), 1.64 (m, 2H, —NHCH$_2$CH$_2$CH$_2$—);

ESI-MS: 466.3 [M+H]$^+$.

Example 53

Synthesis of N-(3-(pyrrolidin-1-yl)propyl)-2-methyl-7-[1,2-dihydro-5-bromo-2-oxo-3H-indol-(Z)-3-ylidene]-4,5,6,7-tetrahydro-1H-indole-3-carboxamide (I-30)

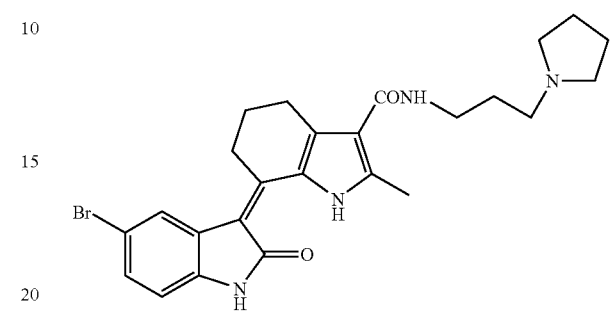

I-30

Similar procedure as Example 25, 5-bromoindolin-2-one 0.21 g (1.0 mmol) and 2-methyl-7-oxo-N-(3-(pyrrolidin-1-yl)propyl)-4,5,6,7-tetrahydro-1H-indole-3-carboxamide (II-10) 0.23 g (0.75 mmol) were reacted to give 0.10 g (27%) of the titled compound as a yellow solid.

$^1$HNMR (300 MHz, DMSO-$d_6$) δ 14.49 (s, 1H, —NH-1), 11.02 (s, 1H, —NH-1'), 7.72 (s, 1H, H-4'), 7.50 (t, 1H, —CONH—), 7.29 (dd, 1H, J=8.2 Hz, H-6'), 6.87 (d, 1H, J=8.2 Hz, H-7'), 3.26 (q, 2H, —CONHCH$_2$), 3.08 (t, 2H, —CH$_2$-4), 2.83 (t, 2H, —CH$_2$-6), 2.49 (m, 9H, —CH$_3$-2, —CH$_2$N(CH$_2$CH$_2$)$_2$), 1.95 (m, 2H, —CH$_2$-5), 1.67 (m, 6H, —CH$_2$CH$_2$N(CH$_2$CH$_2$)$_2$);

ESI-MS: 498.2 [M+H]$^+$.

Example 54

Synthesis of N-(2-(piperidin-1-yl)ethyl)-2-methyl-7-[1,2-dihydro-6-chloro-2-oxo-3H-indol-(Z)-3-ylidene]-4,5,6,7-tetrahydro-1H-indole-3-carboxamide (I-31)

I-31

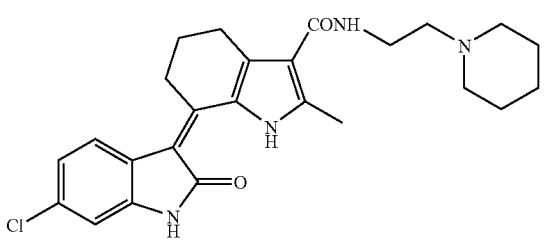

Similar procedure as Example 25, 6-chloroindolin-2-one 0.17 g (1.0 mmol) and 2-methyl-7-oxo-N-(2-(piperidin-1-yl)ethyl)-4,5,6,7-tetrahydro-1H-indole-3-carboxamide (II-6) 0.24 g (0.80 mmol) were reacted to give 0.13 g (36%) of the titled compound as a yellow solid.

$^1$HNMR (300 MHz, DMSO-$d_6$) δ 14.38 (s, 1H, —NH-1), 11.03 (s, 1H, —NH-1'), 7.63 (d, 1H, J=8.6 Hz, H-4'), 7.25 (t, 1H, —CONH—), 7.02 (dd, 1H, J=8.4 Hz, H-5'), 6.90 (d, 1H, J=2.1 Hz, H-7'), 3.32 (q, 2H, —CONHCH$_2$CH$_2$—), 3.08 (t,

2H, —CH₂-4), 2.84 (t, 2H, —CH₂-6), 2.46 (s, 3H, —CH₃-2), 2.40 (m, 6H, —NHCH₂CH₂N(CH₂CH₂)₂CH₂), 1.93 (m, 2H, —CH₂-5), 1.51 (m, 4H, —N(CH₂CH₂)₂CH₂), 1.38 (m, 2H, —N(CH₂CH₂)₂CH₂);

ESI-MS: 453.2 [M+H]⁺.

Example 55

Synthesis of N-(3-(pyrrolidin-1-yl)propyl)-2-methyl-7-[1,2-dihydro-4-fluoro-2-oxo-3H-indol-(Z)-3-ylidene]-4,5,6,7-tetrahydro-1H-indole-3-carboxamide (I-32)

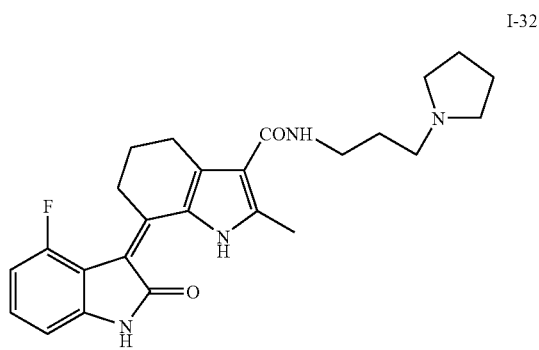

I-32

Similar procedure as Example 25, 4-fluoroindolin-2-one 0.15 g (1.0 mmol) and 2-methyl-7-oxo-N-(3-(pyrrolidin-1-yl)propyl)-4,5,6,7-tetrahydro-1H-indole-3-carboxamide (II-10) 0.24 g (0.80 mmol) were reacted to give 0.12 g (34%) of the titled compound as a yellow solid.

¹HNMR (300 MHz, DMSO-d₆) δ 14.31 (s, 1H, —NH-1), 11.04 (s, 1H, —NH-1'), 7.63 (m, 1H, H-5'), 7.51 (t, 1H, CONH—), 6.79 (t, 1H, H-6'), 6.72 (dd, 1H, J=9.0 Hz, H-7'), 3.27 (q, 2H, —CONHCH₂), 3.07 (t, 2H, —CH₂-4), 2.81 (t, 2H, —CH₂-6), 2.53 (m, 6H, —CH₂N(CH₂CH₂)₂), 2.49 (s, 3H, —CH₃-2), 1.95 (m, 2H, —CH₂-5), 1.70 (m, 6H, —NHCH₂CH₂CH₂—, —CH₂N(CH₂CH₂)₂);

ESI-MS: 437.2 [M+H]⁺; 459.2 [M+Na]⁺.

Example 56

Synthesis of N-(3-(pyrrolidin-1-yl)propyl)-2-methyl-7-[1,2-dihydro-7-fluoro-2-oxo-3H-indol-(Z)-3-ylidene]-4,5,6,7-tetrahydro-1H-indole-3-carboxamide (I-33)

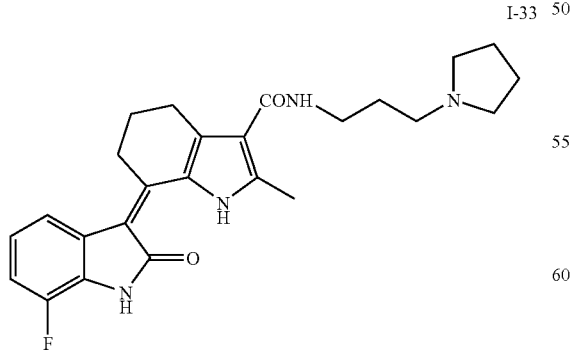

I-33

Similar procedure as Example 25, 4-fluoroindolin-2-one 0.15 g (1.0 mmol) and 2-methyl-7-oxo-N-(3-(pyrrolidin-1-yl)propyl)-4,5,6,7-tetrahydro-1H-indole-3-carboxamide (II-10) 0.24 g (0.80 mmol) were reacted to give 0.11 g (32%) of the titled compound as a yellow solid.

¹HNMR (300 MHz, DMSO-d₆) δ 14.52 (s, 1H, —NH-1), 11.49 (s, 1H, —NH-1'), 7.44 (m, 2H, H-4', H-6'), 6.90 (m, 2H, H-5', —CONH—), 3.25 (q, 2H, —CONHCH₂), 3.09 (t, 2H, —CH₂-4), 2.81 (t, 2H, —CH₂-6), 2.48 (m, 9H, —CH₃-2, —CH₂N(CH₂CH₂)₂), 1.93 (m, 2H, —CH₂-5), 1.67 (m, 6H, —CH₂CH₂N(CH₂CH₂)₂);

ESI-MS: 437.3 [M+H]⁺.

Example 57

Synthesis of N-(2-(diethylamino)ethyl)-2-methyl-7-[1,2-dihydro-5,7-dimethyl-2-oxo-3H-indol-(Z)-3-ylidene]-4,5,6,7-tetrahydro-1H-indole-3-carboxamide (I-34)

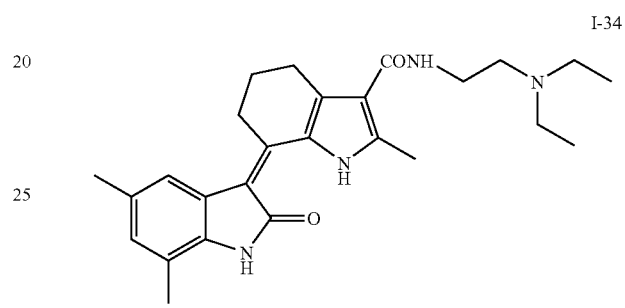

I-34

Similar procedure as Example 25, 5,7-dimethylindolin-2-one 0.14 g (0.87 mmol) and N-(2-(diethylamino)ethyl)-2-methyl-7-oxo-4,5,6,7-tetrahydro-1H-indole-3-carboxamide (II-1) 0.22 g (0.75 mmol) were reacted to give 0.11 g (34%) of the titled compound as a yellow solid.

¹HNMR (300 MHz, DMSO-d₆) δ 14.58 (s, 1H, —NH-1), 10.75 (s, 1H, —NH-1'), 7.29 (s, 1H, H-4'), 7.18 (t, 1H, —CONH—), 6.77 (s, 1H, H-6'), 3.28 (q, 2H, —CONHCH₂), 3.06 (t, 2H, —CH₂-4), 2.82 (t, 2H, —CH₂-6), 2.50~2.41 (m, 9H, —CH₃-2, —CH₂N(CH₂CH₃)₂), 2.28 (s, 3H, —CH₃-5'), 2.20 (s, 3H, —CH₃-7'), 1.93 (m, 2H, —CH₂-5), 0.96 (t, 6H, —CH₂N(CH₂CH₃)₂);

ESI-MS: 435.2 [M+H]⁺.

Example 58

Synthesis of N-(2-(diethylamino)ethyl)-2-methyl-7-[N-isopropyl-1,2-dihydro-2-oxo-3H-indol-5-sulfonamide-(Z)-3-ylidene]-4,5,6,7-tetrahydro-1H-indole-3-carboxamide (I-35)

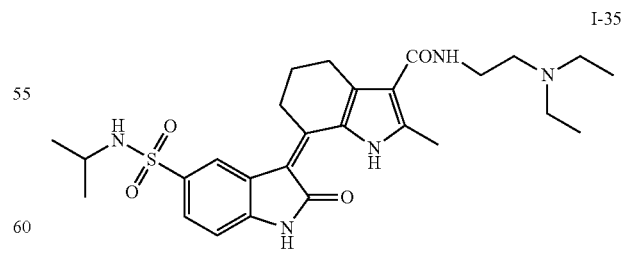

I-35

Similar procedure as Example 25, N-isopropyl-2-oxoindoline-5-sulfonamide 0.26 g (1.0 mmol) and N-(2-(diethylamino)ethyl)-2-methyl-7-oxo-4,5,6,7-tetrahydro-1H-indole-3-carboxamide (II-1) 0.26 g (0.90 mmol) were reacted to give 0.08 g (17%) of the titled compound as a yellow solid.

¹HNMR (300 MHz, DMSO-d₆) δ 14.42 (s, 1H, —NH-1), 11.30 (s, 1H, —NH-1'), 8.03 (s, 1H, —SO₂NH—), 7.60 (dd, 1H, J=8.2 Hz, H-6'), 7.46 (d, 1H, J=7.0 Hz, H-4'), 7.29 (t, 1H, —CONH—), 7.06 (d, 1H, J=8.2 Hz, H-7'), 3.28 (m, 2H, —CONHCH₂), 3.16 (m, 3H, —CH—, —CH₂-4), 2.87 (t, 2H, —CH₂-6), 2.51 (m, 9H, —CH₃-2, —CH₂N(CH₂CH₃)₂), 1.99 (m, 2H, —CH₂-5), 0.97 (m, 12H, —CH(CH₃)₂, —CH₂N(CH₂CH₃)₂);

ESI-MS: 528.3 [M+H]⁺.

Example 59

Synthesis of N-(2-(diethylamino)ethyl)-2-methyl-7-[1,2-dihydro-5-bromo-2-oxo-3H-indol-(Z)-3-ylidene]-4,5,6,7-tetrahydro-1H-indole-3-carboxamide (I-36)

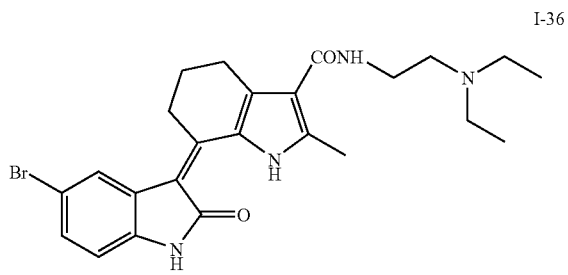

I-36

Similar procedure as Example 25, 5-bromoindolin-2-one 0.21 g (1.0 mmol) and N-(2-(diethylamino)ethyl)-2-methyl-7-oxo-4,5,6,7-tetrahydro-1H-indole-3-carboxamide (II-1) 0.22 g (0.75 mmol) were reacted to give 0.10 g (27%) of the titled compound as a yellow solid.

¹HNMR (300 MHz, CDCl₃) δ 14.23 (s, 1H, —NH-1), 8.23 (s, 1H, —NH-1'), 7.71 (s, 1H, H-4'), 7.24 (d, 1H, J=1.75 Hz, H-6'), 6.79 (d, 1H, J=8.2 Hz, H-7'), 6.47 (bs, 1H, —CONH—), 3.50 (q, 2H, —CONHCH₂CH₂—), 3.09 (t, 2H, —CH₂-4), 2.92 (t, 2H, —CH₂-6), 2.68~2.55 (m, 9H, —CH₃-2, —NHCH₂CH₂N(CH₂CH₃)₂), 2.08 (m, 2H, —CH₂-5), 1.03 (t, 6H, —(CH₂CH₃)₂);

ESI-MS: 486.1 [M+H]⁺.

Example 60

Synthesis of N-(2-(diethylamino)ethyl)-2-methyl-7-[1,2-dihydro-5-nitro-2-oxo-3H-indol-(Z)-3-ylidene]-4,5,6,7-tetrahydro-1H-indole-3-carboxamide (I-37)

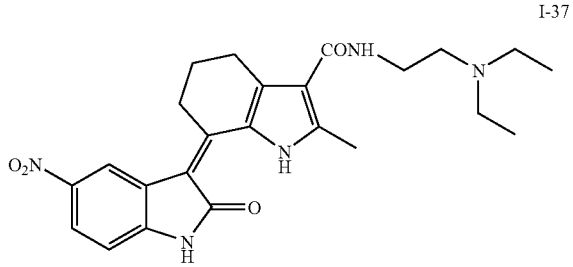

I-37

Similar procedure as Example 25, 5-nitroindolin-2-one 0.18 g (1.0 mmol) and N-(2-(diethylamino)ethyl)-2-methyl-7-oxo-4,5,6,7-tetrahydro-1H-indole-3-carboxamide (II-1) 0.22 g (0.75 mmol) were reacted to give 0.12 g (35%) of the titled compound as a yellow solid.

¹HNMR (300 MHz, DMSO-d₆) δ 14.29 (s, 1H, —NH-1), 11.51 (bs, 1H, —NH-1'), 8.38 (s, 1H, H-4'), 8.06 (dd, 1H, J=8.6 Hz, H-6'), 7.31 (t, 1H, —CONH—), 7.04 (d, 1H, J=8.6 Hz, H-7'), 3.27 (q, 2H, —CONHCH₂), 3.18 (t, 2H, —CH₂-4), 2.86 (t, 2H, —CH₂-6), 2.56~2.49 (m, 6H, —CH₂N(CH₂CH₃)₂), 2.47 (s, 3H, —CH₃-2), 1.98 (m, 2H, —CH₂-5), 0.98 (t, 6H, —CH₂N(CH₂CH₃)₂);

ESI-MS: 452.2 [M+H]⁺.

Example 61

Synthesis of N-(3-(dimethylamino)propyl)-2-methyl-7-[1,2-dihydro-5-fluoro-2-oxo-3H-indol-(Z)-3-ylidene]-4,5,6,7-tetrahydro-1H-indole-3-carboxamide (I-38)

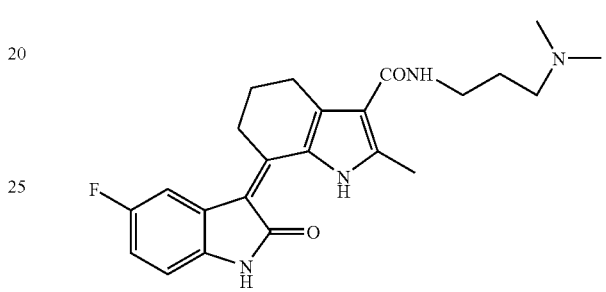

I-38

Similar procedure as Example 25, 5-fluoroindolin-2-one 0.15 g (1.0 mmol) and N-(3-(dimethylamino)propyl)-2-methyl-7-oxo-4,5,6,7-tetrahydro-1H-indole-3-carboxamide (II-4) 0.22 g (0.80 mmol) were reacted to give 0.11 g (34%) of the titled compound as a yellow solid.

¹HNMR (300 MHz, CDCl₃) δ 14.30 (s, 1H, —NH-1), 7.79 (s, 1H, —NH-1'), 7.36 (dd, 1H, J=10.49 Hz, H-4'), 7.09 (bs, 1H, —CONH—), 6.85 (m, 2H, H-6', H-7'), 3.55 (q, 2H, —CONHCH₂), 3.11 (t, 2H, —CH₂-4), 2.96 (t, 2H, —CH₂-6), 2.60 (s, 3H, —CH₃-2), 2.56 (s, 2H, —CH₂CH₂N(CH₃)₂), 2.32 (s, 6H, —N(CH₃)₂)), 2.08 (m, 2H, —CH₂-5), 1.82 (s, 2H, —CH₂CH₂N(CH₃)₂);

ESI-MS: 411.2 [M+H]⁺; 433.2 [M+Na]⁻.

Example 62

Synthesis of N-(2-(diethylamino)ethyl)-2-methyl-7-[1,2-dihydro-5-methoxy carbonyl-2-oxo-3H-indol-(Z)-3-ylidene]-4,5,6,7-tetrahydro-1H-indole-3-carboxamide (I-39)

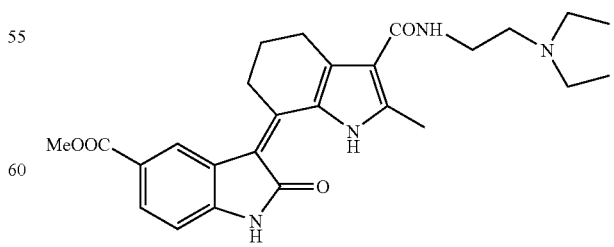

I-39

Similar procedure as Example 25, methyl 2-oxoindoline-5-carboxylate 0.19 g (1.0 mmol) and N-(2-(diethylamino)ethyl)-2-methyl-7-oxo-4,5,6,7-tetrahydro-1H-indole-3-carboxamide (II-1) 0.26 g (0.90 mmol) were reacted to give 0.13 g (31%) of the titled compound as a yellow solid.

¹HNMR (300 MHz, CDCl₃) δ 14.18 (s, 1H, —NH-1), 8.32 (s, 1H, H-4'), 8.15 (s, 1H, —NH-1'), 7.90 (d, 1H, J=8.2 Hz, H-6'), 6.95 (d, 1H, J=8.2 Hz, H-7'), 6.46 (bs, 1H, —CONH—), 3.93 (s, 3H, —OCH₃), 3.51 (q, 2H, —CONHCH₂—), 3.25 (t, 2H, —CH₂-4), 2.96 (t, 2H, —CH₂-6), 2.67~2.55 (m, 9H, —CH₃-2, —NHCH₂CH₂N(CH₂CH₃)₂), 2.08 (m, 2H, —CH₂-5), 1.06 (t, 6H, —(CH₂CH₃)₂);

ESI-MS: 465.2 [M+H]⁺; 487.2 [M+Na]⁺.

Example 63

Synthesis of N-(2-(diethylamino)ethyl)-2-methyl-7-[1,2-dihydro-7-fluoro-2-oxo-3H-indol-(Z)-3-ylidene]-4,5,6,7-tetrahydro-1H-indole-3-carboxamide (I-40)

I-40

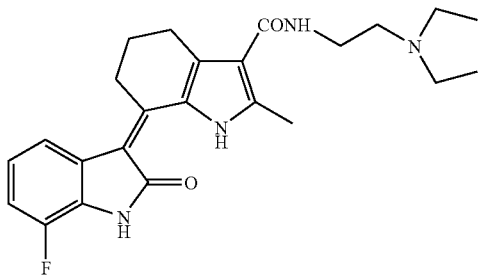

Similar procedure as Example 25, 7-fluoroindolin-2-one 0.15 g (1.0 mmol) and N-(2-(diethylamino)ethyl)-2-methyl-7-oxo-4,5,6,7-tetrahydro-1H-indole-3-carboxamide (II-1) 0.22 g (0.75 mmol) were reacted to give 0.11 g (34%) of the titled compound as a yellow solid.

¹HNMR (300 MHz, CDCl₃) δ 14.22 (s, 1H, —NH-1), 9.41 (s, 1H, —NH-1'), 7.31 (dd, 1H, J=7.36 Hz, H-4'), 6.86 (m, 2H, H-5', H-6'), 6.39 (s, 1H, —CONH—), 3.43 (q, 2H, —CONHCH₂CH₂—), 3.05 (t, 2H, —CH₂-4), 2.87 (t, 2H, —CH₂-6), 2.67~2.55 (m, 9H, —CH₃-2, —NHCH₂CH₂N(CH₂CH₃)₂), 2.00 (m, 2H, —CH₂-5), 0.97 (t, 6H, —(CH₂CH₃)₂);

ESI-MS: 425.2 [M+H]⁺.

Example 64

Synthesis of N-(2-(diethylamino)ethyl)-2-methyl-7-[N-(4-fluorophenyl)-1,2-dihydro-2-oxo-3H-indol-5-sulfonamide-(Z)-3-ylidene]-4,5,6,7-tetrahydro-1H-indole-3-carboxamide (I-41)

I-41

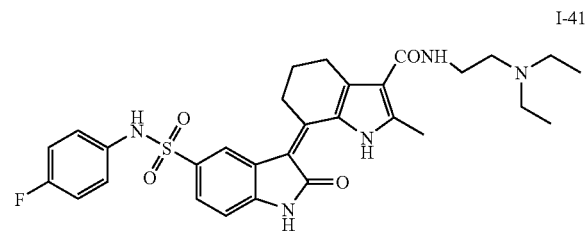

Similar procedure as Example 25, N-(4-fluorophenyl)-2-oxoindoline-5-sulfonamide 0.31 (1.0 mmol) and N-(2-(diethylamino)ethyl)-2-methyl-7-oxo-4,5,6,7-tetrahydro-1H-indole-3-carboxamide (II-1) 0.26 g (0.90 mmol) were reacted to give 0.10 g (19%) of the titled compound as a yellow solid.

¹HNMR (300 MHz, DMSO-d₆) δ 14.34 (s, 1H, —NH-1), 11.31 (s, 1H, —NH-1'), 9.97 (s, 1H, —SO₂NH—), 7.78 (s, 1H, H-4'), 7.51 (dd, 1H, J=8.2 Hz, H-6'), 7.30 (t, 1H, —CONH—), 7.09 (m, 4H, 4-F-Ph), 7.00 (d, 1H, J=8.2 Hz, H-7'), 3.27 (q, 2H, —CONHCH₂), 2.89 (m, 4H, —CH₂-4, —CH₂-6), 2.53 (m, 6H, —NHCH₂CH₂N(CH₂CH₃)₂), 2.47 (s, 3H, —CH₃-2), 1.94 (m, 2H, —CH₂-5), 1.00 (t, 6H, —CH₂N(CH₂CH₃)₂);

ESI-MS: 580.3 [M+H]⁺;

Example 65

Synthesis of N-(2-(diethylamino)ethyl)-2-methyl-7-[5-(piperidin-1-ylsulfonyl)-1,2-dihydro-2-oxo-3H-indol-5-sulfonamide-(Z)-3-ylidene]-4,5,6,7-tetrahydro-1H-indole-3-carboxamide (I-42)

I-42

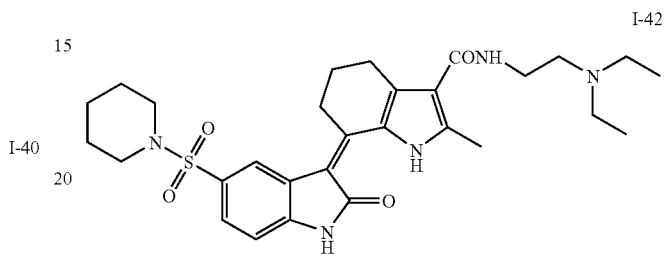

Similar procedure as Example 25, 5-(piperidin-1-ylsulfonyl)indolin-2-one 0.28 g (1.0 mmol) and N-(2-(diethylamino)ethyl)-2-methyl-7-oxo-4,5,6,7-tetrahydro-1H-indole-3-carboxamide (II-1) 0.26 g (0.90 mmol) were reacted to give 0.11 g (22%) of the titled compound as a yellow solid.

¹HNMR (300 MHz, DMSO-d₆) δ 14.41 (s, 1H, —NH-1), 11.37 (s, 1H, —NH-1'), 7.84 (s, 1H, H-4'), 7.52 (dd, 1H, J=8.2 Hz, H-6'), 7.29 (t, 1H, —CONH—), 7.12 (d, 1H, J=8.2 Hz, H-7'), 3.29 (t, 2H, —CONHCH₂), 3.14 (t, 2H, —CH₂-4), 2.87 (m, 6H, —CH₂-6, —SO₂N(CH²CH₂)₂CH₂), 2.51 (m, 9H, —CH₃-2, —CH₂N(CH₂CH₃)₂), 1.98 (m, 2H, —CH₂-5), 1.54 (m, 4H, —SO₂N(CH₂CH₂)₂CH₂), 1.35 (m, 2H, —SO₂N(CH₂CH₂)₂CH₂), 0.96 (t, 6H, —CH₂N(CH₂CH₂)₂);

ESI-MS: 554.3 [M+H]⁺.

Example 66

Synthesis of N-(3-(diethylamino)propyl)-2-methyl-7-[1,2-dihydro-5-fluoro-2-oxo-3H-indol-(Z)-3-ylidene]-4,5,6,7-tetrahydro-1H-indole-3-carboxamide (I-43)

I-43

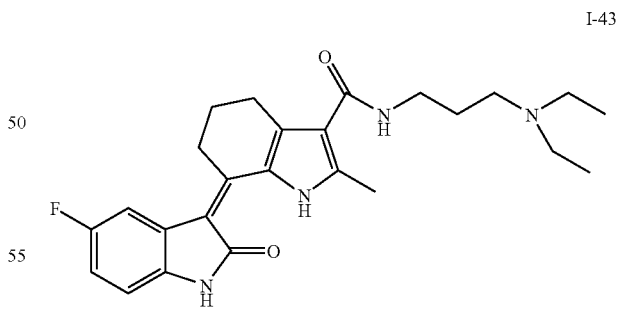

Similar procedure as Example 25, 5-fluoroindolin-2-one 0.15 g (1.0 mmol) and N-(3-(diethylamino)propyl)-2-methyl-7-oxo-4,5,6,7-tetrahydro-1H-indole-3-carboxamide (II-9) 0.23 g (0.75 mmol) were reacted to give 0.12 g (36%) of the titled compound as a yellow solid.

¹HNMR (300 MHz, DMSO-d₆) δ 14.54 (s, 1H, —NH-1), 10.91 (s, 1H, —NH-1'), 7.52 (t, 1H, —CONH—), 7.45 (d, 1H, J=10.7 Hz, H-4'), 6.92 (m, 2H, H-6', H-7'), 3.26 (q, 2H, —CONHCH₂CH₂—), 3.05 (t, 2H, —CH₂-4), 2.82 (t, 2H, —CH₂-6), 2.49~2.44 (m, 9H, CH₃-2, —CH₂CH₂N (CH$_2$CH$_3$)$_2$), 1.95 (m, 2H, —CH$_2$-5), 1.61 (m, 2H, —NHCH$_2$CH$_2$CH$_2$—), 1.01 (t, 6H, —(CH$_2$CH$_3$)$_2$);
ESI-MS: 439.2 [M+H]$^+$; 461.2 [M+Na]$^+$.

Example 67

Synthesis of N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide (I-44)

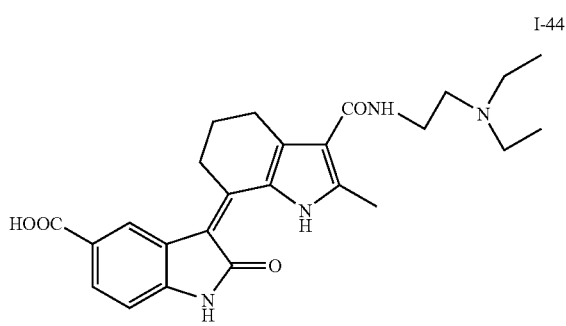

I-44

N-(2-(diethylamino)ethyl)-2-methyl-7-[1,2-dihydro-5-methoxy carbonyl-2-oxo-3H-indol-(Z)-3-ylidene]-4,5,6,7-tetrahydro-1H-indole-3-carboxamide (I-39) 123 mg (0.26 mmol) was dissolved in 12 ml MeOH/H$_2$O(3:1), then 5 ml aq. LiOH (4 mol/L) was added. The mixture was stirred for 15 hours at 5° C., acidified with 2 mol/L HCl aq. to pH 6. The precipitate was collected by filtration, washed with water and dried in vacuum condition to give 70 mg (60%) of the titled compound as a yellow solid.

$^1$HNMR (300 MHz, DMSO-d$_6$) δ 14.35 (s, 1H, —NH-1), 11.18 (s, 1H, —NH-1'), 8.18 (s, 1H, H-4'), 7.77 (d, 1H, J=7.9 Hz, H-6'), 7.33 (t, 1H, —CONH—), 7.04 (d, 1H, J=8.1 Hz, H-7'), 3.32 (q, 2H, —CONHCH$_2$), 3.16 (t, 2H, —CH$_2$-4), 2.85 (t, 2H, —CH$_2$-6), 2.62 (m, 6H, —CH$_2$N(CH$_2$CH$_3$)$_2$), 2.46 (s, 3H, —CH$_3$-2), 1.98 (m, 2H, —CH$_2$-5), 1.00 (t, 6H, —CH$_2$N(CH$_2$CH$_3$)$_2$);
ESI-MS: 451.2 [M+H]$^+$; 473.2 [M+Na]$^+$.

Example 68

Synthesis of N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide (I-45)

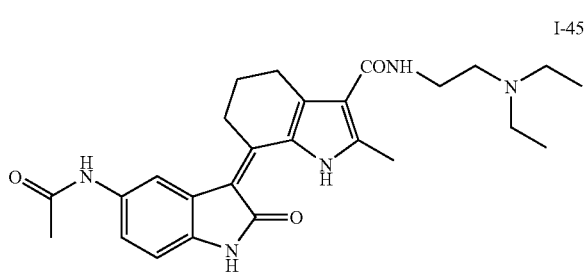

I-45

Iron powder 0.1 g and 6 mol/L HCl aq. 1 ml were added to a suspension of N-(2-(diethylamino)ethyl)-2-methyl-7-[1,2-dihydro-5-nitro-2-oxo-3H-indol-(Z)-3-ylidene]-4,5,6,7-tetrahydro-1H-indole-3-carboxamide (I-37) 0.10 g (0.22 mmol) in 20 ml water. The mixture was stirred for 40 hours at 30° C. under N$_2$, then the iron power was filtered off. The filtrate was basified to pH about 10 with saturated K$_2$CO$_3$ solution and extracted with CH$_2$Cl$_2$. The organic layer separated was dried over anhydrous Na$_2$SO$_4$ and filtered. Acetyl chloride 30 mg (0.38 mmol) and a drop of pyridine were added to the filtrate and stirred for 6 hours at room temperature, then a small amount of ice water was added to stop the reaction. The mixture was basified to pH about 10 with K$_2$CO$_3$ a.q. solution, then the organic layer was separated, dried over anhydrous Na$_2$SO$_4$ and concentrated in vacuo. The residue was purified by a silica gel column, eluted with CH$_2$Cl$_2$/MeOH (25:1), to give 47 mg (46%) of the titled compound as an orange solid.

$^1$HNMR (300 MHz, DMSO-d$_6$) δ 14.50 (s, 1H, —NH-1), 10.77 (s, 1H, —NH-1'), 9.75 (s, 1H, CH$_3$CONH—), 7.84 (s, 1H, H-4'), 7.35 (d, 1H, J=8.2 Hz, H-6'), 7.18 (bs, 1H, —CONH—), 6.77 (d, 1H, J=8.2 Hz, H-7'), 3.29 (m, 2H, —CONHCH$_2$), 3.00 (t, 2H, —CH$_2$-4), 2.79 (t, 2H, —CH$_2$-6), 2.44 (m, 9H, —CH$_3$-2, —CH$_2$N(CH$_2$CH$_3$)$_2$), 1.96~1.85 (m, 5H, —CH$_2$-5, CH$_3$CO—), 0.98 (t, 6H, —CH$_2$N(CH$_2$CH$_3$)$_2$);
ESI-MS: 464.2 [M+H]$^+$.

Example 69

Synthesis of N-(2-(diethylamino)ethyl)-2-methyl-7-[1,2-dihydro-6-chloro-2-oxo-3H-indol-(Z)-3-ylidene]-4,5,6,7-tetrahydro-1H-indole-3-carboxamide (I-46)

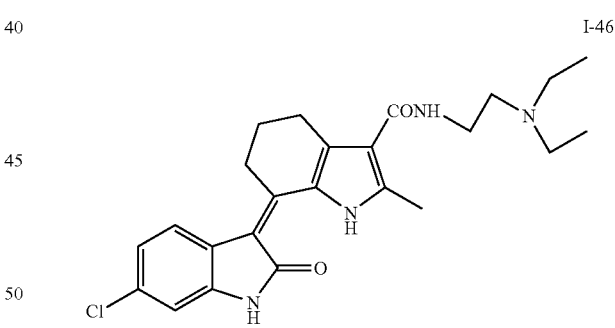

I-46

Similar procedure as Example 25, 6-chloroindolin-2-one 0.17 g (1.0 mmol) and N-(2-(diethylamino)ethyl)-2-methyl-7-oxo-4,5,6,7-tetrahydro-1H-indole-3-carboxamide (II-1) 0.23 g (0.80 mmol) were reacted to give 0.12 g (34%) of the titled compound as a yellow solid.

$^1$HNMR (300 MHz, CDCl$_3$) δ 14.16 (s, 1H, —NH-1), 8.02 (s, 1H, —NH-1'), 7.51 (d, 1H, J=8.4 Hz, H-4'), 7.02 (dd, 1H, J=8.4 Hz, H-5'), 6.90 (d, 1H, J=2 Hz, H-7'), 6.45 (bs, 1H, —CONH—), 3.49 (q, 2H, —CONHCH$_2$CH$_2$—), 3.07 (t, 2H, —CH$_2$-4), 2.90 (t, 2H, —CH$_2$-6), 2.67~2.55 (m, 9H, —CH$_3$-2, —NHCH$_2$CH$_2$N(CH$_2$CH$_3$)$_2$), 2.07 (m, 2H, —CH$_2$-5), 1.03 (t, 6H, —(CH$_2$CH$_3$)$_2$);
ESI-MS: 441.2 [M+H]$^+$; 463.1 [M+Na]$^+$.

Example 70

Synthesis of N-(3-(diethylamino)propyl)-2-methyl-7-[1,2-dihydro-6-chloro-2-oxo-3H-indol-(Z)-3-ylidene]-4,5,6,7-tetrahydro-1H-indole-3-carboxamide (I-47)

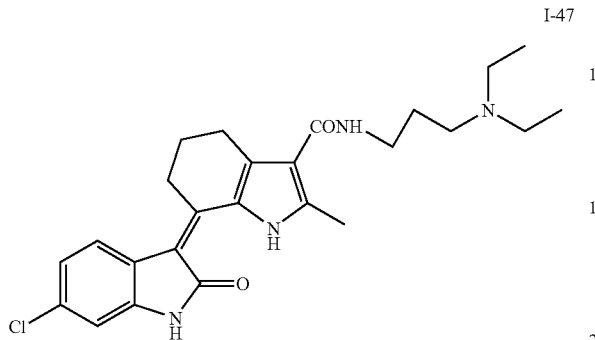

Similar procedure as Example 25, 6-chloroindolin-2-one 0.17 g (1.0 mmol) and N-(3-(diethylamino)propyl)-2-methyl-7-oxo-4,5,6,7-tetrahydro-1H-indole-3-carboxamide (II-9) 0.23 g (0.75 mmol) were reacted to give 0.11 g (32%) of the titled compound as a yellow solid.

$^1$HNMR (300 MHz, DMSO-$d_6$) δ 14.37 (s, 1H, —NH-1), 11.03 (s, 1H, —NH-1'), 7.63 (d, 1H, J=8.5 Hz, H-4'), 7.52 (t, 1H, —CONH—), 7.02 (dd, 1H, J=8.4 Hz, H-5'), 6.91 (d, 1H, J=2 Hz, H-7'), 3.25 (q, 2H, —CONHCH$_2$CH$_2$—), 3.08 (t, 2H, —CH$_2$-4), 2.84 (t, 2H, —CH$_2$-6), 2.52 (m, 6H, —CH$_2$CH$_2$N(CH$_2$CH$_3$)$_2$), 2.45 (s, 3H, —CH$_3$-2), 1.93 (m, 2H, —CH$_2$-5), 1.65 (bs, 2H, —NHCH$_2$CH$_2$CH$_2$—), 0.97 (s, 6H, —N(CH$_2$CH$_3$)$_2$);

ESI-MS: 455.2 [M+H]$^+$; 477.2 [M+Na]$^+$.

Example 71

Synthesis of N-(3-(diethylamino)propyl)-2-methyl-7-[1,2-dihydro-5-bromo-2-oxo-3H-indol-(Z)-3-ylidene]-4,5,6,7-tetrahydro-1H-indole-3-carboxamide (I-48)

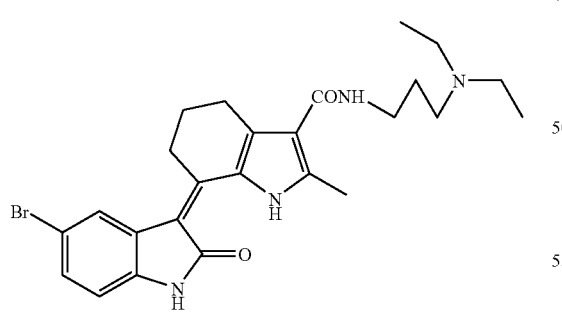

Similar procedure as Example 25, 5-bromoindolin-2-one 0.21 g (1.0 mmol) and N-(3-(diethylamino)propyl)-2-methyl-7-oxo-4,5,6,7-tetrahydro-1H-indole-3-carboxamide (II-9) 0.23 g (0.75 mmol) were reacted to give 0.13 g (35%) of the titled compound as a yellow solid.

$^1$HNMR (300 MHz, DMSO-$d_6$) δ 14.47 (s, 1H, —NH-1), 11.03 (s, 1H, —NH-1'), 7.72 (d, 1H, J=1.5 Hz, H-4'), 7.52 (t, 1H, —CONH—), 7.29 (dd, 1H, J=8.2 Hz, H-6'), 6.87 (d, 1H, J=8.2 Hz, H-7'), 3.24 (q, 2H, —CONHCH$_2$CH$_2$—), 3.08 (t, 2H, —CH$_2$-4), 2.82 (t, 2H, —CH$_2$-6), 2.46~2.40 (m, 9H, —CH$_3$-2, —CH$_2$CH$_2$N(CH$_2$CH$_3$)$_2$), 1.96 (m, 2H, —CH$_2$-5), 1.61 (m, 2H, —NHCH$_2$CH$_2$CH$_2$—), 0.94 (t, 6H, —N(CH$_2$CH$_3$)$_2$);

ESI-MS: 500.2 [M+H]$^+$.

Example 72

Synthesis of N-(2-(diethylamino)ethyl)-2-methyl-7-[1,2-dihydro-4-fluoro-2-oxo-3H-indol-(Z)-3-ylidene]-4,5,6,7-tetrahydro-1H-indole-3-carboxamide (I-49)

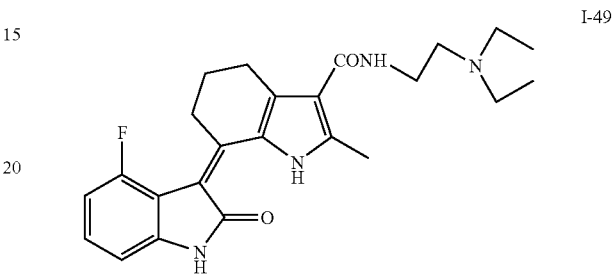

Similar procedure as Example 25, 4-fluoroindolin-2-one 0.15 g (1.0 mmol) and N-(2-(diethylamino)ethyl)-2-methyl-7-oxo-4,5,6,7-tetrahydro-1H-indole-3-carboxamide (II-1) 0.23 g (0.79 mmol) were reacted to give 0.13 g (39%) of the titled compound as a yellow solid.

$^1$HNMR (300 MHz, CDCl$_3$) δ 14.20 (s, 1H, —NH-1), 9.56 (s, 1H, —NH-1'), 7.49 (q, 1H, H-6'), 6.83 (dd, 1H, J=8.69 Hz, H-7'), 6.68 (t, 1H, H-5'), 6.50 (bs, 1H, —CONH—), 3.51 (m, 2H, —CONHCH$_2$CH$_2$—), 3.05 (t, 2H, —CH$_2$-4), 2.89 (t, 2H, —CH$_2$-6), 2.67-2.55 (m, 9H, —CH$_3$-2, —NHCH$_2$CH$_2$N(CH$_2$CH$_3$)$_2$), 2.04 (m, 2H, —CH$_2$-5), 1.06 (t, 6H, —(CH$_2$CH$_3$)$_2$);

ESI-MS: 425.2 [M+H]$^+$.

Example 73

Synthesis of N-(2-(diethylamino)ethyl)-2-methyl-7-[5-(pyrrolidine-1-carbonyl)-1,2-dihydro-2-oxo-3H-indol-(Z)-3-ylidene]-4,5,6,7-tetrahydro-1H-indole-3-carboxamide (I-50)

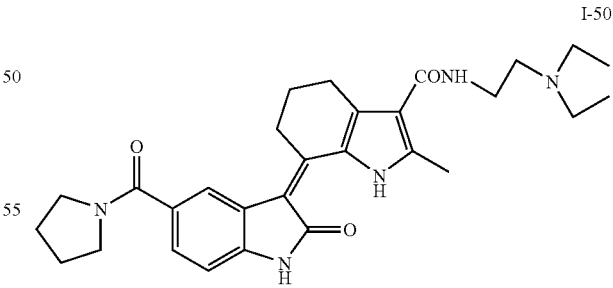

Similar procedure as Example 2, N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide (I-44) 50 mg (0.11 mmol) and pyrrolidine 71 mg (1.0 mmol) were reacted to give 38 mg (69%) of the titled compound as a yellow solid.

$^1$HNMR (300 MHz, DMSO-$d_6$) δ 14.45 (s, 1H, —NH-1), 11.05 (s, 1H, —NH-1'), 7.76 (s, 1H, H-4'), 7.34 (dd, 1H, J=8.0

Hz, H-6'), 7.25 (t, 1H, —CONH—), 6.94 (d, 1H, J=8.0 Hz, H-7'), 3.48 (t, 4H, —N(CH$_2$CH$_2$)$_2$), 3.28 (q, 2H, —CONHCH$_2$), 3.10 (t, 2H, —CH$_2$-4), 2.85 (t, 2H, —CH$_2$-6), 2.51 (m, 6H, —CH$_2$N(CH$_2$CH$_3$)$_2$), 2.47 (s, 3H, —CH$_3$-2), 1.86 (m, 2H, —CH$_2$-5), 1.85 (bs, 4H, —N(CH$_2$CH$_2$)$_2$), 0.97 (t, 6H, —CH$_2$N(CH$_2$CH$_3$)$_2$);

ESI-MS: 504.3 [M+H]$^+$; 526.3 [M+Na]$^+$.

Example 74

Synthesis of N-(2-(diethylamino)ethyl)-2-methyl-7-[N-(4-fluorophenyl)-5-carboxamide-1,2-dihydro-2-oxo-3H-indol-(Z)-3-ylidene]-4,5,6,7-tetrahydro-1H-indole-3-carboxamide (I-51)

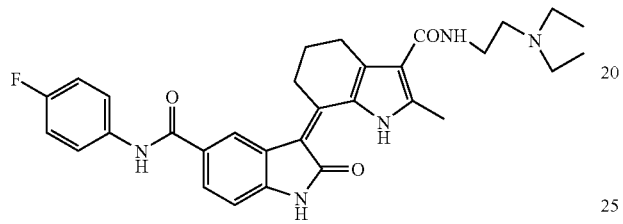

I-51

Similar procedure as Example 2, N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide (I-44) 50 mg (0.11 mmol) and 4-fluorobenzenamine 0.10 g (0.9 mmol) were reacted to give 43 mg (72%) of the titled compound as a yellow solid.

$^1$HNMR (300 MHz, DMSO-d$_6$) δ 14.45 (s, 1H, —NH-1), 11.23 (s, 1H, —NH-1'), 10.21 (s, 1H, —CONH-ph), 8.18 (s, 1H, H-4'), 7.78 (m, 3H, ph, H-6'), 7.29 (bs, 1H, —CONH—), 7.21 (t, 2H, ph), 7.03 (d, 1H, J=8.1 Hz, H-7'), 3.24 (q, 2H, —CONHCH$_2$), 2.87 (s, 2H, —CH$_2$-4), 2.57~2.49 (m, 11H, —CH$_2$-6, —CH$_2$N(CH$_2$CH$_3$)$_2$, —CH$_3$-2), 1.98 (m, 2H, —CH$_2$-5), 1.00 (s, 6H, —CH$_2$N(CH$_2$CH$_2$)$_2$);

ESI-MS: 544.3 [M+H]$^+$.

Example 75

Synthesis of N-(3-(diethylamino)propyl)-2-methyl-7-[1,2-dihydro-7-fluoro-2-oxo-3H-indol-(Z)-3-ylidene]-4,5,6,7-tetrahydro-1H-indole-3-carboxamide (I-52)

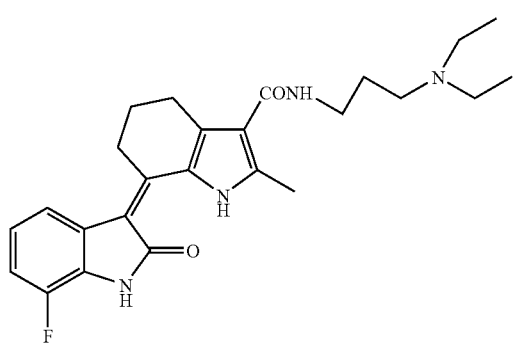

I-52

Similar procedure as Example 25, 7-fluoroindolin-2-one 0.15 g (1.0 mmol) and N-(3-(diethylamino)propyl)-2-methyl-7-oxo-4,5,6,7-tetrahydro-1H-indole-3-carboxamide (II-9) 0.23 g (0.75 mmol) were reacted to give 0.11 g (33%) of the titled compound as a yellow solid.

$^1$HNMR (300 MHz, CDCl$_3$) δ 14.24 (s, 1H, —NH-1), 8.47 (s, 1H, —NH-1'), 7.41 (d, 1H, J=7.65 Hz, H-4'), 6.95 (m, 3H, H-5', H-6', —CONH—), 3.56 (q, 2H, —CONHCH$_2$CH$_2$—), 3.17 (t, 2H, —CH$_2$-4), 2.96 (t, 2H, —CH$_2$-6), 2.61 (s, 3H, —CH$_3$-2), 2.54 (m, 6H, —CH$_2$CH$_2$N(CH$_2$CH$_3$)$_2$), 2.07 (m, 2H, —CH$_2$-5), 1.76 (m, 2H, —NHCH$_2$CH$_2$CH$_2$—), 1.01 (t, 6H, —(CH$_2$CH$_3$)$_2$);

ESI-MS: 439.2 [M+H]$^+$; 461.2 [M+Na]$^+$.

Example 76

Synthesis of N-(2-(diethylamino)ethyl)-2-methyl-7-[1,2-dihydro-5-methoxy-2-oxo-3H-indol-(Z)-3-ylidene]-4,5,6,7-tetrahydro-1H-indole-3-carboxamide (I-53)

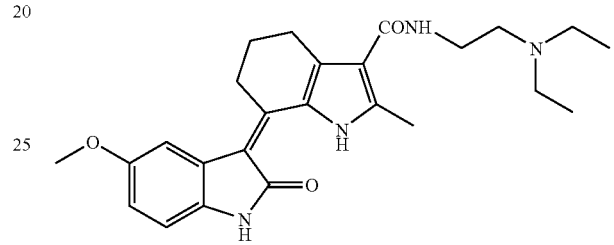

I-53

Similar procedure as Example 25, 5-methoxyindolin-2-one 0.16 g (1.0 mmol) and N-(2-(diethylamino)ethyl)-2-methyl-7-oxo-4,5,6,7-tetrahydro-1H-indole-3-carboxamide (II-1) 0.22 g (0.75 mmol) were reacted to give 0.12 g (37%) of the titled compound as a yellow solid.

$^1$HNMR (300 MHz, CDCl$_3$) δ 14.33 (s, 1H, —NH-1), 7.73 (s, 1H, —NH-1'), 7.23 (d, 1H, J=2.1 Hz, H-4'), 7.90 (d, 1H, J=8.4 Hz, H-6'), 6.95 (d, 1H, J=8.4 Hz, H-7'), 6.42 (bs, 1H, —CONH—), 3.83 (s, 3H, —OCH$_3$), 3.50 (q, 2H, —CONH CH$_2$CH$_2$—), 3.14 (t, 2H, —CH$_2$-4), 2.95 (t, 2H, —CH$_2$-6), 2.66~2.53 (m, 9H, —CH$_3$-2, —NHCH$_2$CH$_2$N(CH$_2$CH$_3$)$_2$), 2.08 (m, 2H, —CH$_2$-5), 1.05 (t, 6H, —(CH$_2$CH$_3$)$_2$);

ESI-MS: 437.2 [M+H]$^+$.

Example 77

Synthesis of N-(2-(diethylamino)ethyl)-2-methyl-7-[1,2-dihydro-5-trifluoromethoxy-2-oxo-3H-indol-(Z)-3-ylidene]-4,5,6,7-tetrahydro-1H-indole-3-carboxamide (I-54)

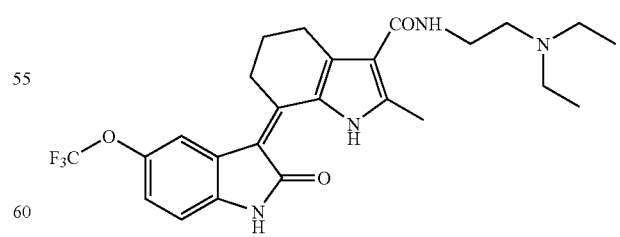

I-54

Similar procedure as Example 25, 5-(trifluoromethoxy)indolin-2-one 0.15 g (0.69 mmol) and N-(2-(diethylamino)ethyl)-2-methyl-7-oxo-4,5,6,7-tetrahydro-1H-indole-3-carboxamide (II-1) 0.17 g (0.60 mmol) were reacted to give 0.10 g (34%) of the titled compound as a yellow solid.

¹HNMR (300 MHz, CDCl₃) δ 14.22 (s, 1H, —NH-1), 8.62 (s, 1H, —NH-1'), 7.45 (s, 1H, H-4'), 7.04 (dd, 1H, J=8.4 Hz, H-6'), 6.87 (d, 1H, J=8.4 Hz, H-7'), 6.53 (s, 1H, —CONH—), 3.53 (q, 2H, —CONHCH₂CH₂—), 3.06 (t, 2H, —CH₂-4), 2.86 (t, 2H, —CH₂-6), 2.69~2.57 (m, 9H, —CH₃-2, —NHCH₂CH₂N(CH₂CH₃)₂), 2.03 (m, 2H, —CH₂-5), 1.06 (t, 6H, —N(CH₂CH₃)₂);

ESI-MS: 491.2 [M+H]⁺.

Example 78

Synthesis of N-(2-(diethylamino)ethyl)-2-methyl-7-[N-methyl-1,2-dihydro-2-oxo-3H-indol-5-sulfonamide-(Z)-3-ylidene]-4,5,6,7-tetrahydro-1H-indole-3-carboxamide (I-55)

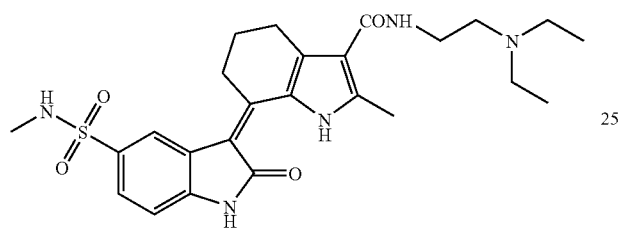

I-55

Similar procedure as Example 25, N-methyl-2-oxoindoline-5-sulfonamide 0.23 g (1.0 mmol) and N-(2-(diethylamino)ethyl)-2-methyl-7-oxo-4,5,6,7-tetrahydro-1H-indole-3-carboxamide (II-1) 0.26 g (0.90 mmol) were reacted to give 0.06 g (13%) of the titled compound as a yellow solid.

¹HNMR (300 MHz, DMSO-d₆) δ 14.42 (s, 1H, —NH-1), 11.32 (s, 1H, —NH-1'), 7.99 (s, 1H, —SO₂NH—), 7.57 (dd, 1H, J=8.1 Hz, H-6'), 7.31 (m, 2H, —CONH—, H-4'), 7.05 (d, 1H, J=8.1 Hz, H-7'), 3.30 (m, 2H, —CONHCH₂), 3.15 (t, 2H, —CH₂-4), 2.87 (t, 2H, —CH₂-6), 2.51 (m, 9H, —CH₃-2, —CH₂N(CH₂CH₃)₂), 2.39 (d, 3H, J=5.1 Hz, CH₃NH—), 1.97 (m, 2H, —CH₂-5), 0.97 (t, 6H, —CH₂N(CH₂CH₃)₂);

ESI-MS: 500.2 [M+H]⁺.

Example 79

Synthesis of N-(2-(pyridin-2-yl)ethyl)-2-methyl-7-[1,2-dihydro-5-fluoro-2-oxo-3H-indol-(Z)-3-ylidene]-4,5,6,7-tetrahydro-1H-indole-3-carboxamide (I-56)

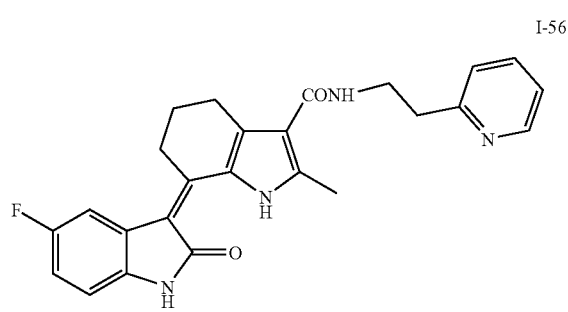

I-56

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and 2-(pyridin-2-yl)ethanamine 85 mg (0.70 mmol) were reacted. The mixture was poured into ice water, basified to pH about 10 and extracted with CH₂Cl₂. The organic layer separated was dried and concentrated in vacuo. The residue was purified by a silica gel column, eluted with CH₂Cl₂/MeOH (8:1), to give 0.07 g (35%) of the titled compound as a yellow solid.

¹HNMR (300 MHz, DMSO-d₆) δ 14.54 (s, 1H, —NH-1), 10.91 (s, 1H, —NH-1'), 8.52 (d, 1H, Py-6), 7.74 (t, 1H, Py-4), 7.56 (t, 1H, —CONH—), 7.45 (dd, 1H, J=10.80 Hz, H-4'), 7.31 (d, 1H, J=7.78 Hz, Py-3), 7.23 (t, 1H, Py-5), 6.95 (t, 1H, H-6'), 6.87 (dd, 1H, J=8.4 Hz, H-7'), 3.60 (q, 2H, —CONHCH₂), 3.06 (t, 2H, —CH₂-4), 2.99 (t, 2H, —CH₂-Py), 2.72 (t, 2H, —CH₂-6), 2.40 (s, 3H, —CH₃-2), 1.90 (m, 2H, —CH₂-5);

ESI-MS: 431.1 [M+H]⁺; 453.1 [M+Na]⁺.

Example 80

Synthesis of N-(2-(dimethylamino)ethyl)-N,2-dimethyl-7-[1,2-dihydro-5-fluoro-2-oxo-3H-indol-(Z)-3-ylidene]-4,5,6,7-tetrahydro-1H-indole-3-carboxamide (I-57)

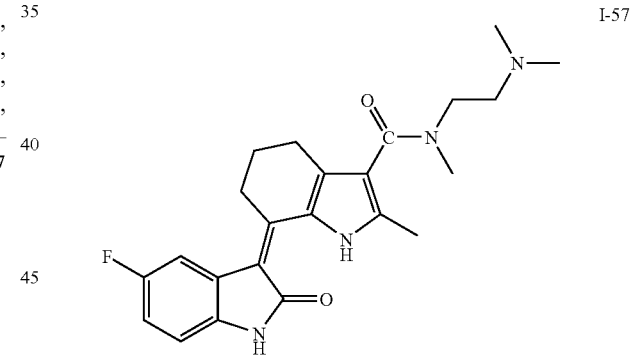

I-57

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and N,N,N'-trimethyl-1,2-ethylenediamine 71 mg (0.70 mmol) were reacted to give 0.10 g (53%) of the titled compound as a yellow solid.

¹HNMR (300 MHz, DMSO-d₆) δ 14.46 (s, 1H, —NH-1), 10.89 (s, 1H, —NH-1'), 7.44 (dd, 1H, J=10.9 Hz, H-4'), 6.95 (t, 1H, H-6'), 6.86 (dd, 1H, J=8.4 Hz, H-7'), 3.50 (bs, 2H, —CON(CH₃)CH₂—), 3.08 (s, 2H, —CH₂-4), 2.92 (s, 3H, —CON(CH₃)—), 2.56 (s, 2H, —CH₂-6), 2.42 (bs, 2H, —CH₂N(CH₃)₂), 2.29 (s, 3H, —CH₃-2), 2.18 (bs, 2H, —CH₂-5), 1.96 (m, 6H, —N—(CH₃)₂);

ESI-MS: 411.2 [M+H]⁺; 433.2 [M+Na]⁻.

Example 81

Synthesis of N-(2-(dimethylamino)ethyl)-N,2-dimethyl-7-[1,2-dihydro-6-chloro-2-oxo-3H-indol-(Z)-3-ylidene]-4,5,6,7-tetrahydro-1H-indole-3-carboxamide (I-58)

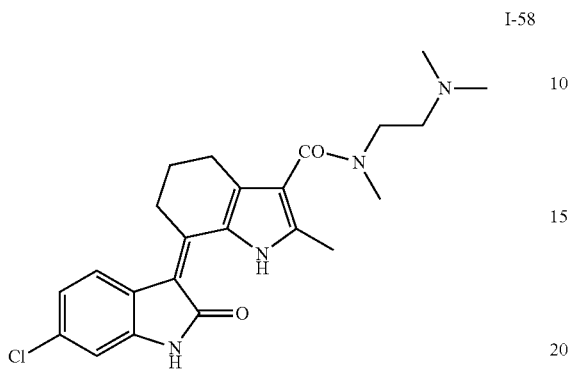

I-58

Similar procedure as Example 20, 6-chloroindolin-2-one 0.10 g (0.6 mmol) and 2-methyl-7-oxo-4,5,6,7-tetrahydro-1H-indole-3-carboxylic acid (S4) 0.18 g (0.55 mmol) were reacted to give 2-methyl-7-[1,2-dihydro-6-chloro-2-oxo-3H-indol-(Z)-3-ylidene]-4,5,6,7-tetrahydro-1H-indole-3-carboxylic acid 0.16 g as a brown crude solid. Similar procedure as Example 2, the crude product above-mentioned without further purified and N,N,N'-trimethyl-1,2-ethylenediamine 60 mg (0.59 mmol) were reacted to give 0.05 g (19%) of the titled compound as a yellow solid.

$^1$HNMR (300 MHz, DMSO-$d_6$) δ 14.30 (s, 1H, —NH-1), 11.14 (s, 1H, —NH-1'), 7.63 (d, 1H, J=8.5 Hz, H-4'), 7.01 (d, 1H, J=8.3 Hz, H-5'), 6.90 (s, 1H, H-7'), 3.50 (m, 2H, —CON(CH$_3$)CH$_2$—), 3.08 (s, 2H, —CH$_2$-4), 2.92 (s, 3H, —CON(CH$_3$)—), 2.59 (s, 2H, —CH$_2$-6), 2.42 (bs, 2H, —CH$_2$N(CH$_3$)$_2$), 2.29 (s, 3H, —CH$_3$-2), 2.18 (bs, 2H, —CH$_2$-5), 1.93 (m, 6H, —N(CH$_3$)$_2$);

ESI-MS: 427.2 [M+H]$^+$.

Example 82

Synthesis of N-benzyl-N,2-dimethyl-7-[1,2-dihydro-5-fluoro-2-oxo-3H-indol-(Z)-3-ylidene]-4,5,6,7-tetrahydro-1H-indole-3-carboxamide (I-59)

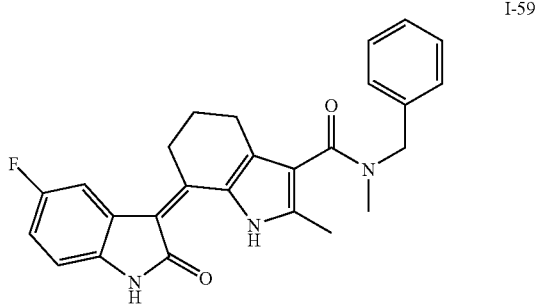

I-59

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and N-methyl-benzylamine 85 mg (0.70 mmol) were reacted to give 0.13 g (66%) of the titled compound as a yellow solid.

$^1$HNMR (300 MHz, DMSO-$d_6$) δ 14.51 (s, 1H, —NH-1), 10.91 (s, 1H, —NH-1'), 7.40 (m, 6H), 6.95 (t, 1H), 6.87 (t, 1H), 4.62 (s, 2H, ph-CH$_2$—), 3.09 (s, 2H, —CH$_2$-4), 2.84 (s, 3H, —NCH$_3$), 2.64 (s, 2H, —CH$_2$-6), 2.33 (s, 3H, —CH$_3$-2), 1.97 (m, 2H, —CH$_2$-5);

ESI-MS: 430.2 [M+H]$^+$; 452.1 [M+Na]$^+$.

Example 83

Synthesis of 2-methyl-3-[(S)-2-(pyrrolidin-1-ylmethyl)pyrrolidin-1-carbonyl]-7-[1,2-dihydro-5-fluoro-2-oxo-3H-indol-(Z)-3-ylidene]-4,5,6,7-tetrahydro-1H-indole (I-60)

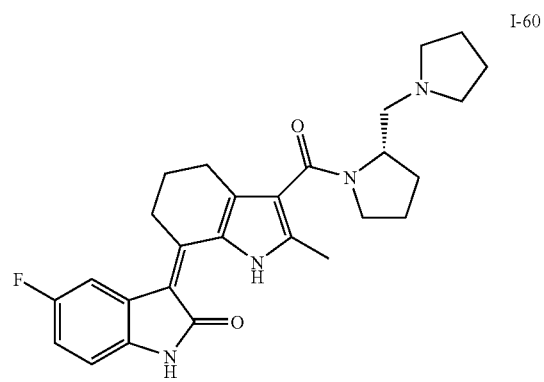

I-60

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and (S)-1,2'-methylenedipyrrolidine 0.11 g (0.71 mmol) were reacted to give 0.12 g (56%) of the titled compound as a yellow solid.

$^1$HNMR (300 MHz, DMSO-$d_6$) δ 14.47 (s, 1H, —NH-1), 10.90 (s, 1H, —NH-1'), 7.44 (dd, 1H, J=10.7 Hz, H-4'), 6.98~6.84 (m, 2H, H-6', H-7'), 4.29 (bs, 1H), 3.08 (m, 2H, —CH$_2$-4), 2.63~2.49 (m, 10H), 2.31 (s, 3H, —CH$_3$-2), 1.99~1.84 (m, 6H), 1.62 (bs, 4H)

ESI-MS: 463.2 [M+H]$^+$.

Example 84

Synthesis of 2-methyl-3-[4-(2-hydroxyethyl)-piperazin-1-carbonyl]-7-[1,2-dihydro-5-fluoro-2-oxo-3H-indol-(Z)-3-ylidene]-4,5,6,7-tetrahydro-1H-indole (I-61)

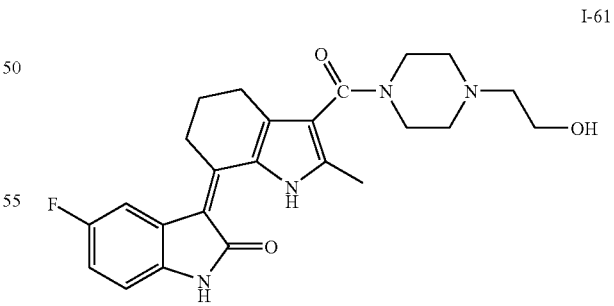

I-61

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and 2-(piperazin-1-yl)ethanol 0.09 g (0.70 mmol) were reacted to give 0.10 g (50%) of the titled compound as a yellow solid.

$^1$HNMR (300 MHz, DMSO-$d_6$) δ 14.50 (s, 1H, —NH-1), 10.90 (s, 1H, —NH-1'), 7.44 (dd, 1H, J=10.9 Hz, H-4'), 6.95

(t, 1H, H-6'), 6.88 (dd, 1H, J=8.1 Hz, H-7'), 4.42 (t, 1H, —OH), 3.47 (m, 6H, —CON($CH_2CH_2$)$_2$N—$CH_2$—, —$CH_2$—OH), 2H, —$CH_2$-4), 2.59 (t, 2H, —$CH_2$-6), 2.40 (6H, —$CH_2$—N($CH_2CH_2$)$_2$N—), 2.31 (s, 3H, $CH_3$-2), 1.94 (bs, 2H, —$CH_2$-5);

ESI-MS: 439.2 [M+H]$^+$; 461.1 [M+Na]$^+$.

Example 85

Synthesis of 2-methyl-3-(1,4'-bipiperidin-1'-carbonyl)-7-[1,2-dihydro-5-fluoro-2-oxo-3H-indol-(Z)-3-ylidene]-4,5,6,7-tetrahydro-1H-indole (I-62)

I-62

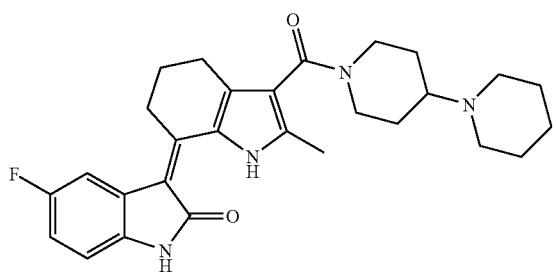

Similar procedure as Example 2, 2-methyl-7-[1,2-dihydro-5-fluoro-2-oxo-3H-indol-(Z)-3-ylidene]-4,5,6,7-tetrahydro-1H-indole-3-carboxylic acid (IV-2) 0.10 g (0.46 mmol) and 1,4'-bipiperidine 0.12 g (0.71 mmol) were reacted to give 0.14 g (64%) of the titled compound as a yellow solid.

$^1$HNMR (300 MHz, DMSO-d$_6$) δ 14.49 (s, 1H, —NH-1), 10.90 (s, 1H, —NH-1'), 7.45 (dd, 1H, J=10.9 Hz, H-4'), 6.95 (t, 1H, H-6'), 6.88 (dd, 1H, J=7.0 Hz, H-7'), 3.09 (s, 2H, —$CH_2$-4), 2.59 (s, 2H, —$CH_2$-6), 2.50 (m, 4H, piperidine), 2.42 (m, 5H, piperidine), 2.30 (s, 3H, —$CH_3$-2), 1.94 (s, 2H, —$CH_2$-5), 1.72 (m, 2H, piperidine), 1.46 (m, 4H, piperidine), 1.37 (m, 4H, piperidine);

ESI-MS: 477.2 [M+H]$^+$; 499.3 [M+Na]$^+$.

Example 86

Synthesis of N-(3-(diethylamino)-2-hydroxypropyl)-2-methyl-7-[1,2-dihydro-2-oxo-3H-indol-(Z)-3-ylidene]-4,5,6,7-tetrahydro-1H-indole-3-carboxamide (I-63)

I-63

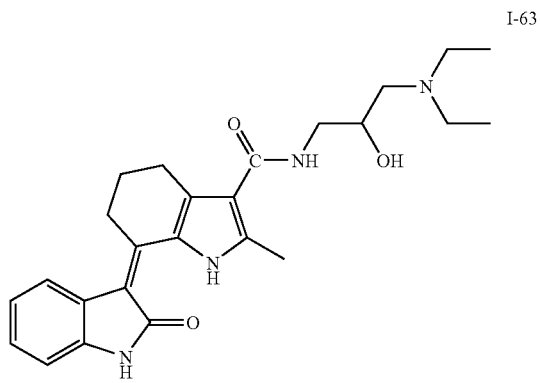

Indolin-2-one 0.11 g (0.83 mmol) and N-(3-(diethylamino)-2-hydroxypropyl)-2-methyl-7-oxo-4,5,6,7-tetrahydro-1H-indole-3-carboxamide (II-12) 0.24 g (0.75 mmol) were dissolved in 10 ml anhydrous pyridine, then TiCl$_4$ 0.3 ml was added. The mixture was stirred for 10 hours at 100 to 110° C., then poured into the ice water and extracted with $CH_2Cl_2$. The organic layer separated was washed with water and saturated sodium chloride solution, then dried over anhydrous $Na_2SO_4$ and concentrated in vacuo. The residue was purified by a silica gel column, eluted with $CH_2Cl_2$/MeOH (108:1), to give 0.09 g (28%) of the titled compound as a yellow solid.

$^1$HNMR (500 MHz, CDCl$_3$) δ 14.26 (s, 1H, —NH-1), 8.20 (bs, 1H, —NH-1'), 7.61 (d, 1H, J=7.90 Hz, H-4'), 7.15 (t, 1H, H-6'), 7.04 (t, 1H, H-5'), 6.90 (d, 1H, J=7.61 Hz, H-7'), 6.23 (s, 1H, —CONH—), 3.86 (m, 1H, —CONHCH(H)—), 3.73 (m, 1H, —CONHCH(H)—), 3.33 (m, 1H, —CH(OH)—), 3.11 (t, 2H, —$CH_2$-4), 2.87 (t, 2H, —$CH_2$-6), 2.69 (m, 2H, —$CH_2$N($CH_2CH_3$)$_2$), 2.59~2.40 (m, 7H, —$CH_3$-2, —$CH_2$N($CH_2CH_3$)$_2$), 2.01 (m, 2H, —$CH_2$-5), 1.05 (t, 6H, —$CH_2$N($CH_2CH_3$)$_2$);

ESI-MS: 437.2 [M+H]$^+$.

Example 87

Synthesis of N-(3-(diethylamino)-2-hydroxypropyl)-2-methyl-7-[1,2-dihydro-5-fluoro-2-oxo-3H-indol-(Z)-3-ylidene]-4,5,6,7-tetrahydro-1H-indole-3-carboxamide (I-64)

I-64

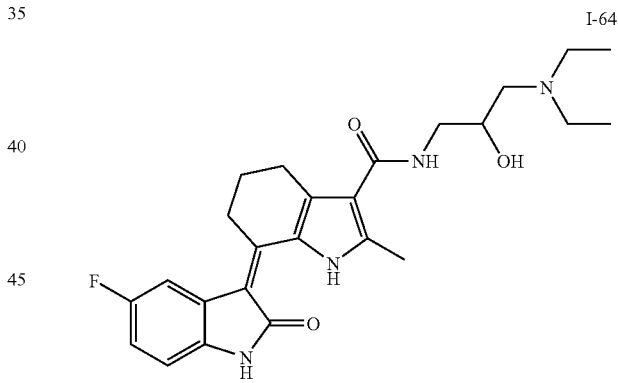

Similar procedure as Example 86, 5-fluoroindolin-2-one 0.12 g (0.79 mmol) and N-(3-(diethylamino)-2-hydroxypropyl)-2-methyl-7-oxo-4,5,6,7-tetrahydro-1H-indole-3-carboxamide (II-12) 0.23 g (0.72 mmol) were reacted to give 0.11 g (34%) of the titled compound as a yellow solid.

$^1$HNMR (300 MHz, CDCl$_3$) δ 14.32 (s, 1H, —NH-1), 8.27 (bs, 1H, —NH-1'), 7.35 (dd, 1H, J=10.67 Hz, H-4'), 6.92~6.80 (m, 2H, H-6', H-7'), 6.28 (t, 1H, —CONH—), 3.90 (m, 1H, —CONHCH(H)—), 3.74 (m, 1H, —CONHCH(H)—), 3.38 (m, 1H, —CH(OH)—), 3.09 (t, 2H, —$CH_2$-4), 2.92 (t, 2H, —$CH_2$-6), 2.72 (m, 2H, —$CH_2$N($CH_2CH_3$)$_2$), 2.62 (s, 3H, —$CH_3$-2), 2.61~2.40 (m, 4H, —$CH_2$N($CH_2CH_3$)$_2$), 2.07 (m, 2H, —$CH_2$-5), 1.08 (t, 6H, —$CH_2$N($CH_2CH_3$)$_2$);

ESI-MS: 455.3 [M+H]$^+$.

Example 88

Synthesis of N-(3-(diethylamino)-2-hydroxypropyl)-2-methyl-7-[1,2-dihydro-5-chloro-2-oxo-3H-indol-(Z)-3-ylidene]-4,5,6,7-tetrahydro-1H-indole-3-carboxamide (I-65)

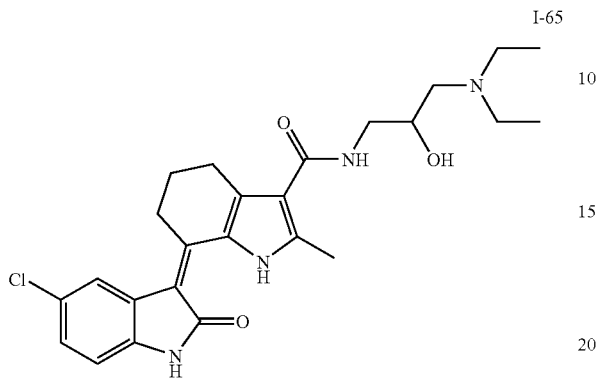

I-65

Similar procedure as Example 86, 5-chloroindolin-2-one 0.13 g (0.78 mmol) and N-(3-(diethylamino)-2-hydroxypropyl)-2-methyl-7-oxo-4,5,6,7-tetrahydro-1H-indole-3-carboxamide (II-12) 0.23 g (0.72 mmol) were reacted to give 0.10 g (30%) of the titled compound as a yellow solid.

$^1$HNMR (300 MHz, CDCl$_3$) δ 14.25 (s, 1H, —NH-1), 8.18 (bs, 1H, —NH-1'), 7.57 (s, 1H, H-4'), 7.12 (dd, 1H, J=8.23 Hz, H-6'), 6.83 (d, 1H, J=8.23 Hz, H-7'), 6.25 (s, 1H, —CONH—), 3.87 (m, 1H, —CONHCH(H)—), 3.70 (m, 1H, —CONHCH(H)—), 3.34 (m, 1H, —CH(OH)—), 3.07 (t, 2H, —CH$_2$-4), 2.89 (t, 2H, —CH$_2$-6), 2.71 (m, 2H, —CH$_2$N(CH$_2$CH$_3$)$_2$), 2.66~2.40 (m, 7H, —CH$_3$-2, —CH$_2$N(CH$_2$CH$_3$)$_2$), 2.06 (m, 2H, —CH$_2$-5), 1.07 (t, 6H, —CH$_2$N(CH$_2$CH$_3$)$_2$);

ESI-MS: 471.3 [M+H]$^+$, 493.2 [M+Na]$^+$.

Example 89

Synthesis of N-(3-(dimethylamino)-2-hydroxypropyl)-2-methyl-7-[1,2-dihydro-5-fluoro-2-oxo-3H-indol-(Z)-3-ylidene]-4,5,6,7-tetrahydro-1H-indole-3-carboxamide (I-66)

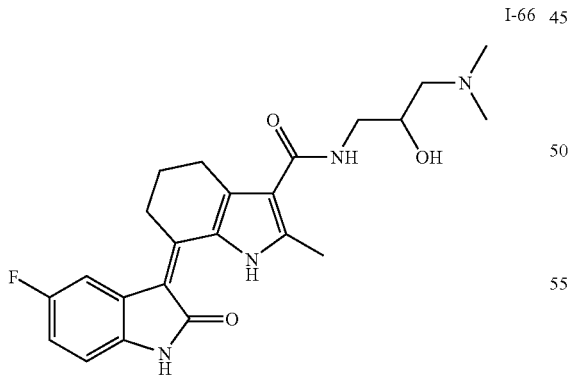

I-66

Similar procedure as Example 86, 5-fluoroindolin-2-one 0.12 g (0.79 mmol) and N-(3-(dimethylamino)-2-hydroxypropyl)-2-methyl-7-oxo-4,5,6,7-tetrahydro-1H-indole-3-carboxamide (II-13) 0.21 g (0.72 mmol) were reacted to give 0.08 g (26%) of the titled compound as a yellow solid.

$^1$HNMR (300 MHz, CDCl$_3$) δ 14.33 (s, 1H, —NH-1), 7.77 (bs, 1H, —NH-1'), 7.35 (dd, 1H, J=10.39 Hz, H-4'), 6.91~6.78 (m, 2H, H-6', H-7'), 6.19 (bs, 1H, —CONH—), 3.90 (m, 1H, —CONHCH(H)—), 3.69 (m, 1H, —CONHCH(H)—), 3.37 (m, 1H, —CH(OH)—), 3.09 (t, 2H, —CH$_2$-4), 2.92 (t, 2H, —CH$_2$-6), 2.61 (s, 3H, —CH$_3$-2), 2.44~2.34 (m, 8H, —CH$_2$N(CH$_3$)$_2$), 2.06 (m, 2H, —CH$_2$-5);

ESI-MS: 427.3 [M+H]$^+$.

Example 90

Synthesis of N-(2-hydroxy-3-morpholinopropyl)-2-methyl-7-[1,2-dihydro-2-oxo-3H-indol-(Z)-3-ylidene]-4,5,6,7-tetrahydro-1H-indole-3-carboxamide (I-67)

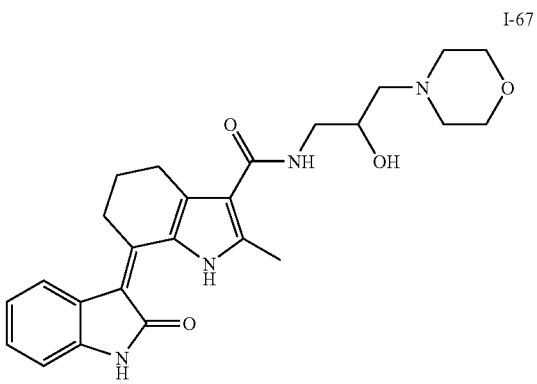

I-67

Similar procedure as Example 86, indolin-2-one 0.11 g (0.83 mmol) and N-(2-hydroxy-3-morpholinopropyl)-2-methyl-7-oxo-4,5,6,7-tetrahydro-1H-indole-3-carboxamide (II-14) 0.25 g (0.75 mmol) were reacted to give 0.12 g (35%) of the titled compound as a yellow solid.

$^1$HNMR (300 MHz, CDCl$_3$) δ 14.29 (s, 1H, —NH-1), 7.99 (s, 1H, —NH-1'), 7.62 (d, 1H, J=7.86 Hz, H-4'), 7.17 (t, 1H, H-6'), 7.06 (t, 1H, H-5'), 6.90 (d, 1H, J=7.47 Hz, H-7'), 6.12 (s, 1H, —CONH—), 3.95 (s, 1H, —CONHCH(H)—), 3.69 (s, 6H, —OH, —CONHCH(H)—, —CH$_2$N(CH$_2$CH$_2$)$_2$O), 3.37 (m, 1H, —CH(OH)—), 3.13 (t, 2H, —CH$_2$-4), 2.90 (t, 2H, —CH$_2$-6), 2.69 (m, 2H, —CH$_2$N(CH$_2$CH$_2$)$_2$O), 2.60 (s, 3H, —CH$_3$-2), 2.46 (m, 4H, —CH$_2$N(CH$_2$CH$_2$)$_2$O), 2.04 (m, 2H, —CH$_2$-5);

ESI-MS: 451.3 [M+H]$^+$.

Example 91

Synthesis of N-(2-hydroxy-3-morpholinopropyl)-2-methyl-7-[1,2-dihydro-5-fluoro-2-oxo-3H-indol-(Z)-3-ylidene]-4,5,6,7-tetrahydro-1H-indole-3-carboxamide (I-68)

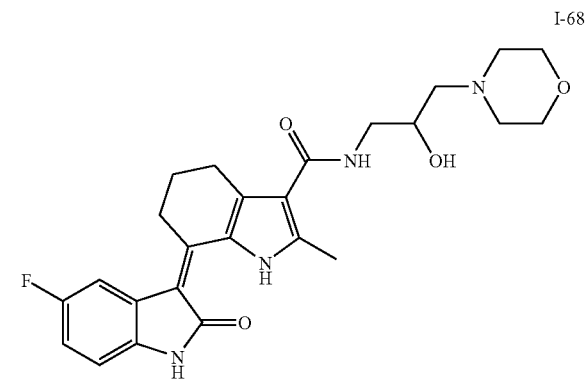

I-68

Similar procedure as Example 86, 5-fluoroindolin-2-one 0.12 g (0.79 mmol) and N-(2-hydroxy-3-morpholinopropyl)-2-methyl-7-oxo-4,5,6,7-tetrahydro-1H-indole-3-carboxamide (II-14) 0.24 g (0.72 mmol) were reacted to give 0.11 g (33%) of the titled compound as a yellow solid.
¹HNMR (300 MHz, CDCl₃) δ 14.34 (s, 1H, —NH-1), 7.65 (s, 1H, —NH-1'), 7.32 (d, 1H, J=11.4 Hz, H-4'), 6.87~6.79 (m, 2H, H-6', H-7'), 6.06 (s, 1H, —CONH—), 3.92 (s, 1H, —CONHCH(H)—), 3.72 (bs, 6H, —OH, —CONHCH(H)—, —CH₂N(CH₂CH₂)₂O), 3.34 (m, 1H, —CH(OH)—), 3.10 (t, 2H, —CH₂-4), 2.96 (s, 2H, —CH₂-6), 2.65~2.60 (m, 5H, —CH₂N(CH₂CH₂)₂O, —CH₃-2), 2.45 (m, 4H, —CH₂N(CH₂CH₂)₂O), 2.07 (m, 2H, —CH₂-5);
ESI-MS: 469.2 [M+H]⁺, 491.2 [M+Na]⁺; 467.3 [M−H]⁻.

Example 92

Synthesis of N-(2-hydroxy-3-morpholinopropyl)-2-methyl-7-[1,2-dihydro-5-chloro-2-oxo-3H-indol-(Z)-3-ylidene]-4,5,6,7-tetrahydro-1H-indole-3-carboxamide (I-69)

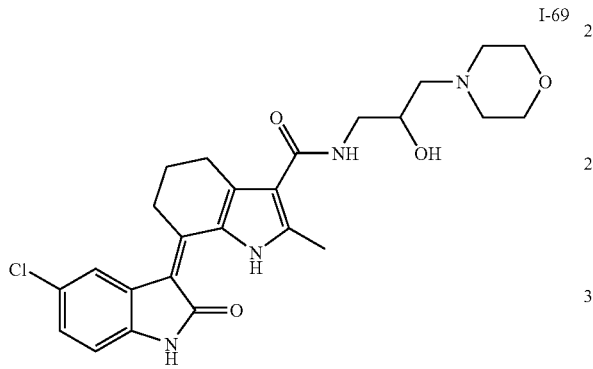

I-69

Similar procedure as Example 86, 5-chloroindolin-2-one 0.12 g (0.72 mmol) and N-(2-hydroxy-3-morpholinopropyl)-2-methyl-7-oxo-4,5,6,7-tetrahydro-1H-indole-3-carboxamide (II-14) 0.22 g (0.66 mmol) were reacted to give 0.11 g (34%) of the titled compound as a yellow solid.
¹HNMR (500 MHz, CDCl₃) δ 14.30 (s, 1H, —NH-1), 7.70 (s, 1H, —NH-1'), 7.59 (s, 1H, H-4'), 7.12 (d, 1H, J=7.95 Hz, H-6'), 6.83 (d, 1H, J=8.35 Hz, H-7'), 6.09 (s, 1H, —CONH—), 3.93 (s, 1H, —CONHCH(H)—), 3.72 (bs, 6H, —OH, —CONHCH(H)—, —CH₂N(CH₂CH₂)₂O), 3.34 (m, 1H, —CH(OH)—), 3.12 (t, 2H, —CH₂-4), 2.95 (s, 2H, —CH₂-6), 2.67 (s, 2H, —CH₂N(CH₂CH₂)₂O), 2.61 (s, 3H, —CH₃-2), 2.46 (m, 4H, —CH₂N(CH₂CH₂)₂O), 2.09 (m, 2H, —CH₂-5);
ESI-MS: 485.2 [M+H]⁺; 483.1 [M−H]⁻.

Example 93

Synthesis of N-(2-hydroxy-3-(pyrrolidin-1-yl)propyl)-2-methyl-7-[1,2-dihydro-2-oxo-3H-indol-(Z)-3-ylidene]-4,5,6,7-tetrahydro-1H-indole-3-carboxamide (I-70)

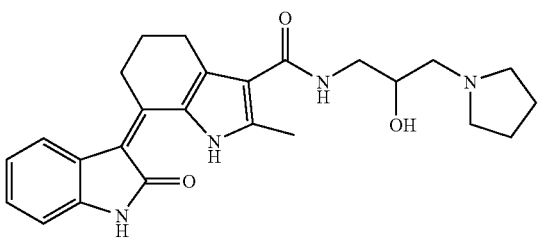

I-70

Similar procedure as Example 86, indolin-2-one 0.11 g (0.83 mmol) and N-(2-hydroxy-3-(pyrrolidin-1-yl)propyl)-2-methyl-7-oxo-4,5,6,7-tetrahydro-1H-indole-3-carboxamide (II-15) 0.24 g (0.75 mmol) were reacted to give 0.10 g (31%) of the titled compound as a yellow solid.
¹HNMR (500 MHz, CDCl₃) δ 14.32 (s, 1H, —NH-1), 7.80 (bs, 1H, —NH-1'), 7.63 (d, 1H, J=7.95 Hz, H-4'), 7.15 (t, 1H, H-6'), 7.05 (t, 1H, H-5'), 6.91 (d, 1H, J=7.73 Hz, H-7'), 6.44 (bs, 1H, —CONH—), 4.02 (s, 1H, —CONHCH(H)—), 3.75 (m, 1H, —CONHCH(H)—), 3.51 (m, 1H, —CH(OH)—), 3.15 (s, 2H, —CH₂-4), 2.94 (m, 4H, —CH₂-6, —CH₂N(CH₂)₄), 2.85 (m, 4H, —CH₂N(CH₂CH₂CH₂CH₂)), 2.61 (s, 3H, —CH₃-2), 2.06 (m, 2H, —CH₂-5), 1.94 (s, 4H, —CH₂N(CH₂CH₂CH₂CH₂));
ESI-MS: 435.3 [M+H]⁺, 457.2 [M+Na]⁺.

Example 94

Synthesis of N-(2-hydroxy-3-(pyrrolidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide (I-71)

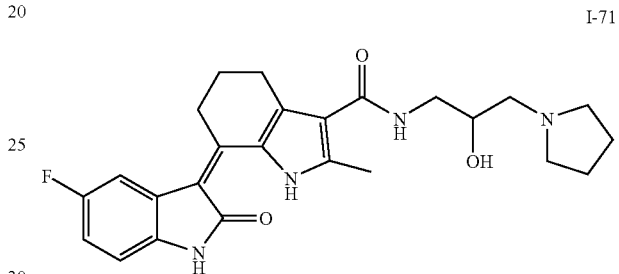

I-71

Similar procedure as Example 86, 5-fluoroindolin-2-one 0.12 g (0.79 mmol) and N-(2-hydroxy-3-(pyrrolidin-1-yl)propyl)-2-methyl-7-oxo-4,5,6,7-tetrahydro-1H-indole-3-carboxamide (II-15) 0.23 g (0.72 mmol) were reacted to give 0.09 g (28%) of the titled compound as a yellow solid.
¹HNMR (300 MHz, CDCl₃) δ 14.33 (s, 1H, —NH-1), 7.89 (bs, 1H, —NH-1'), 7.36 (d, 1H, J=10.92 Hz, H-4'), 6.86~6.80 (m, 2H, H-6', H-7'), 6.22 (s, 1H, —CONH—), 3.91 (s, 1H, —CONHCH(H)—), 3.73 (m, 1H, —CONHCH(H)—), 3.37 (m, 1H, —CH(OH)—), 3.08 (s, 2H, —CH₂-4), 2.93 (s, 2H, —CH₂-6), 2.74 (m, 2H, —CH₂N(CH₂)₄), 2.67~2.45 (m, 7H, —CH₃-2, —CH₂N(CH₂CH₂CH₂CH₂)), 2.06 (m, 2H, —CH₂-5), 1.81 (bs, 4H, —CH₂N(CH₂CH₂CH₂CH₂));
ESI-MS: 453.3 [M+H]⁺, 475.2 [M+Na]⁺.

Example 95

Synthesis of N-(2-hydroxy-3-(pyrrolidin-1-yl)propyl)-2-methyl-7-[1,2-dihydro-5-chloro-2-oxo-3H-indol-(Z)-3-ylidene]-4,5,6,7-tetrahydro-1H-indole-3-carboxamide (I-72)

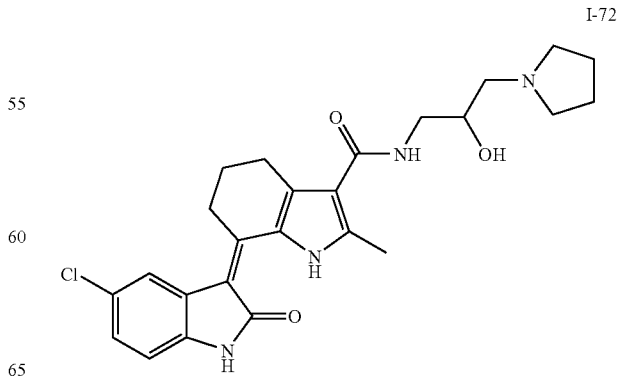

I-72

Similar procedure as Example 86, 5-chloroindolin-2-one 0.14 g (0.84 mmol) and N-(2-hydroxy-3-(pyrrolidin-1-yl)

propyl)-2-methyl-7-oxo-4,5,6,7-tetrahydro-1H-indole-3-carboxamide (II-15) 0.23 g (0.72 mmol) were reacted to give 0.11 g (33%) of the titled compound as a yellow solid.

$^1$HNMR (300 MHz, DMSO-$d_6$) δ 14.52 (s, 1H, —NH-1), 11.02 (s, 1H, —NH-1'), 7.61 (s, 1H, H-4'), 7.52 (t, 1H, —CONH—), 7.18 (dd, 1H, J=8.24 Hz, H-6'), 6.93 (d, 1H, J=8.25 Hz, H-7'), 5.71 (bs, 1H, —CH(OH)—), 3.99 (bs, 1H, —CH(OH)—), 3.31 (m, 7H, —CH$_2$CH(OH)CH$_2$—, —CH$_3$-2), 3.10 (m, 6H, —CH$_2$N(CH$_2$CH$_2$CH$_2$CH$_2$), —CH$_2$-4), 2.86 (t, 2H, —CH$_2$-6), 1.96 (m, 6H, —CH$_2$-5, —CH$_2$N(CH$_2$CH$_2$CH$_2$));

ESI-MS: 469.2 [M+H]$^+$.

Example 96

Synthesis of N-(2-hydroxy-3-(piperidin-1-yl)propyl)-2-methyl-7-[1,2-dihydro-2-oxo-3H-indol-(Z)-3-ylidene]-4,5,6,7-tetrahydro-1H-indole-3-carboxamide (I-73)

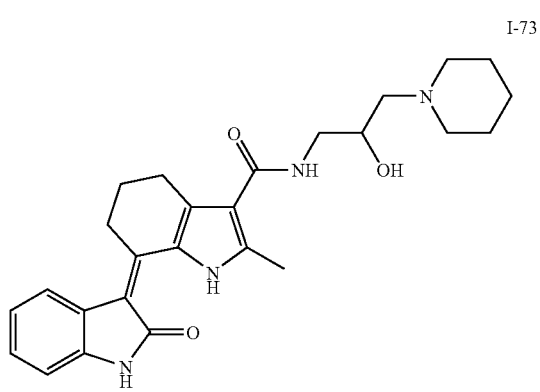

I-73

Similar procedure as Example 86, indolin-2-one 0.11 g (0.83 mmol) and N-(2-hydroxy-3-(piperidin-1-yl)propyl)-2-methyl-7-oxo-4,5,6,7-tetrahydro-1H-indole-3-carboxamide (II-16) 0.24 g (0.72 mmol) were reacted to give 0.09 g (28%) of the titled compound as a yellow solid.

$^1$HNMR (300 MHz, CDCl$_3$) δ 14.31 (s, 1H, —NH-1), 7.75 (bs, 1H, —NH-1'), 7.64 (d, 1H, J=7.99 Hz, H-4'), 7.16 (t, 1H, H-6'), 7.07 (t, 1H, H-5'), 6.91 (d, 1H, J=7.67 Hz, H-7'), 6.19 (bs, 1H, —CONH—), 3.95 (m, 1H, —CONHCH(H)—), 3.69 (m, 1H, —CONHCH(H)—), 3.38 (m, 1H, —CH(OH)—), 3.13 (t, 2H, —CH$_2$-4), 2.94 (s, 2H, —CH$_2$-6), 2.67 (bs, 2H, —CH$_2$N(CH$_2$)$_5$), 2.60 (s, 3H, —CH$_3$-2), 2.45 (bs, 4H, —CH$_2$N(CH$_2$CH$_2$CH$_2$CH$_2$CH$_2$)), 2.06 (m, 2H, —CH$_2$-5), 1.64~1.43 (m, 6H, —CH$_2$N(CH$_2$CH$_2$—CH$_2$—CH$_2$CH$_2$));

ESI-MS: 449.4 [M+H]$^+$, 471.3 [M+Na]$^+$.

Example 97

Synthesis of N-(2-hydroxy-3-(piperidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide (I-74)

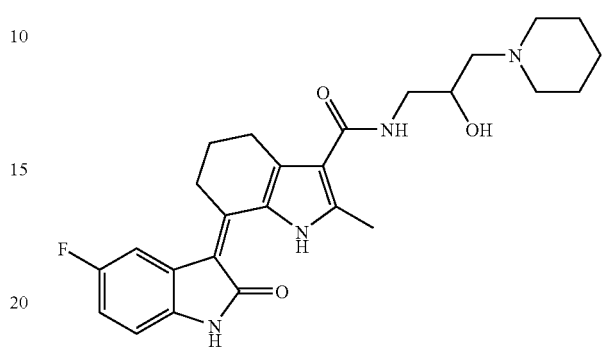

I-74

Similar procedure as Example 86, 5-fluoroindolin-2-one 0.12 g (0.79 mmol) and N-(2-hydroxy-3-(piperidin-1-yl)propyl)-2-methyl-7-oxo-4,5,6,7-tetrahydro-1H-indole-3-carboxamide (II-16) 0.23 g (0.69 mmol) were reacted to give 0.10 g (31%) of the titled compound as a yellow solid.

$^1$HNMR (300 MHz, CDCl$_3$) δ 14.30 (s, 1H, —NH-1), 8.09 (bs, 1H, —NH-1'), 7.35 (d, 1H, J=10.5 Hz, H-4'), 6.93~6.80 (m, 2H, H-6', H-7'), 6.21 (s, 1H, —CONH—), 3.93 (s, 1H, —CONHCH(H)—), 3.71 (d, 1H, —CONHCH(H)—), 3.30 (m, 1H, —CH(OH)—), 3.01 (s, 2H, —CH$_2$-4), 2.88 (s, 2H, —CH$_2$-6), 2.59 (bs, 5H, —CH$_3$-2, —CH$_2$N(CH$_2$)$_5$), 2.38 (m, 4H, —CH$_2$N(CH$_2$CH$_2$CH$_2$CH$_2$CH$_2$)), 2.03 (m, 2H, —CH$_2$-5), 1.60 (bs, 6H, —CH$_2$N(CH$_2$CH$_2$CH$_2$CH$_2$));

ESI-MS: 465.3 [M—H]$^-$.

Example 98

Synthesis of N-(2-hydroxy-3-(piperidin-1-yl)propyl)-2-methyl-7-[1,2-dihydro-5-chloro-2-oxo-3H-indol-(Z)-3-ylidene]-4,5,6,7-tetrahydro-1H-indole-3-carboxamide (I-75)

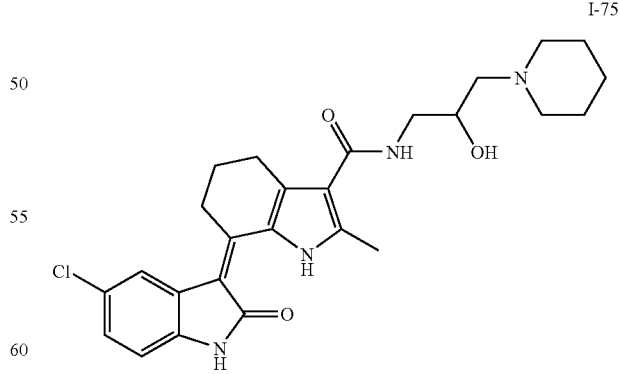

I-75

Similar procedure as Example 86, 5-chloroindolin-2-one 0.14 g (0.84 mmol) and N-(2-hydroxy-3-(piperidin-1-yl)propyl)-2-methyl-7-oxo-4,5,6,7-tetrahydro-1H-indole-3-carboxamide (II-16) 0.23 g (0.69 mmol) were reacted to give 0.12 g (36%) of the titled compound as a yellow solid.

¹HNMR (300 MHz, CDCl₃) δ 14.25 (s, 1H, —NH-1), 8.11 (bs, 1H, —NH-1'), 7.57 (s, 1H, H-4'), 7.13 (d, 1H, J=8.67 Hz, H-6'), 6.83 (d, 1H, J=8.46 Hz, H-7'), 6.20 (s, 1H, —CONH—), 3.92 (m, 1H, —CONHCH(H)—), 3.72 (m, 1H, —CONHCH(H)—), 3.32 (m, 1H, —CH(OH)—), 3.08 (s, 2H, —CH₂-4), 2.89 (s, 2H, —CH₂-6), 2.59 (s, 5H, —CH₃-2, —CH₂N(CH₂)₅), 2.40 (m, 4H, —CH₂N(CH₂CH₂CH₂CH₂CH₂)), 2.05 (m, 2H, —CH₂-5), 1.60~1.43 (m, 6H, —CH₂N(CH₂CH₂—CH₂—CH₂CH₂));

ESI-MS: 483.3 [M+H]⁺.

Example 99

Synthesis of N-[2-hydroxy-3-(4-methylpiperazin-1-yl)propyl]-2-methyl-7-[1,2-dihydro-2-oxo-3H-indol-(Z)-3-ylidene]-4,5,6,7-tetrahydro-1H-indole-3-carboxamide (I-76)

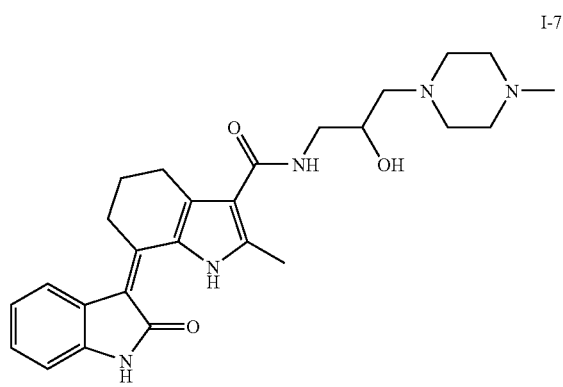

I-76

Similar procedure as Example 86, indolin-2-one 0.11 g (0.83 mmol) and N-(2-hydroxy-3-(4-methylpiperazin-1-yl)propyl)-2-methyl-7-oxo-4,5,6,7-tetrahydro-1H-indole-3-carboxamide (II-17) 0.25 g (0.72 mmol) were reacted to give 0.11 g (33%) of the titled compound as a yellow solid.

¹HNMR (300 MHz, CDCl₃) δ 14.29 (s, 1H, —NH-1), 7.96 (s, 1H, —NH-1'), 7.63 (d, 1H, J=8.14 Hz, H-4'), 7.15 (t, 1H, H-6'), 7.06 (t, 1H, H-5'), 6.91 (dd, 1H, J=7.69 Hz, H-7'), 6.13 (t, 1H, —CONH—), 3.94 (m, 1H, —CONHCH(H)—), 3.70 (m, 1H, —CONHCH(H)—), 3.36 (m, 1H, —CH(OH)—), 3.14 (t, 2H, —CH₂-4), 2.90 (t, 2H, —CH₂-6), 2.72 (bs, 2H, —CH₂N(CH₂CH₂)₂NCH₃), 2.60 (s, 3H, —CH₃-2), 2.46~2.37 (m, 8H, —N(CH₂CH₂)₂NCH₃), 2.30 (s, 3H, —N(CH₂CH₂)₂NCH₃), 2.06 (m, 2H, —CH₂-5);

ESI-MS: 464.1 [M+H]⁺, 486.0 [M+Na]⁺.

Example 100

Synthesis of N-[2-hydroxy-3-(4-methylpiperazin-1-yl)propyl]-2-methyl-7-[1,2-dihydro-5-fluoro-2-oxo-3H-indol-(Z)-3-ylidene]-4,5,6,7-tetrahydro-1H-indole-3-carboxamide (I-77)

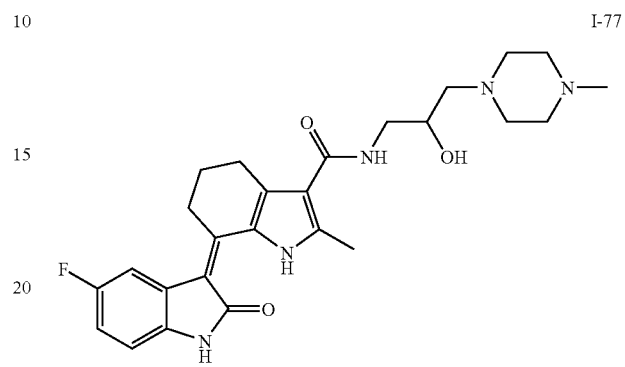

I-77

Similar procedure as Example 86, 5-fluoroindolin-2-one 0.13 g (0.86 mmol) and N-(2-hydroxy-3-(4-methylpiperazin-1-yl)propyl)-2-methyl-7-oxo-4,5,6,7-tetrahydro-1H-indole-3-carboxamide (II-17) 0.25 g (0.72 mmol) were reacted to give 0.10 g (29%) of the titled compound as a yellow solid.

¹HNMR (300 MHz, CDCl₃) δ 14.32 (s, 1H, —NH-1), 8.07 (bs, 1H, —NH-1'), 7.35 (dd, 1H, J=10.6 Hz, H-4'), 6.89~6.78 (m, 2H, H-6', H-7'), 6.16 (t, 1H, —CONH—), 3.94 (s, 1H, —CONHCH(H)—), 3.73 (m, 1H, —CONHCH(H)—), 3.33 (m, 1H, —CH(OH)—), 3.09 (t, 2H, —CH₂-4), 2.90 (t, 2H, —CH₂-6), 2.74 (s, 2H, —CH₂N(CH₂CH₂)₂NCH₃), 2.60 (s, 3H, —CH₃-2), 2.47~2.37 (m, 8H, —N(CH₂CH₂)₂NCH₃), 2.30 (s, 3H, —N(CH₂CH₂)₂NCH₃), 2.07 (m, 2H, —CH₂-5);

ESI-MS: 482.0 [M+H]⁺.

Example 101

Synthesis of N-[2-hydroxy-3-(4-methylpiperazin-1-yl)propyl]-2-methyl-7-[1,2-dihydro-5-chloro-2-oxo-3H-indol-(Z)-3-ylidene]-4,5,6,7-tetrahydro-1H-indole-3-carboxamide (I-78)

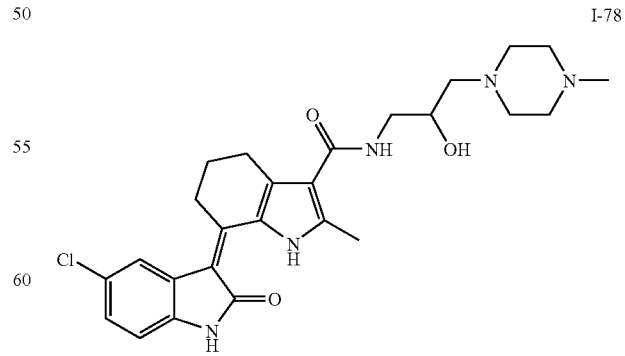

I-78

Similar procedure as Example 86, 5-chloroindolin-2-one 0.14 g (0.84 mmol) and N-(2-hydroxy-3-(4-methylpiperazin-1-yl)propyl)-2-methyl-7-oxo-4,5,6,7-tetrahydro-1H-indole- 3-carboxamide (II-17) 0.25 g (0.72 mmol) were reacted to give 0.11 g (31%) of the titled compound as a yellow solid.

$^1$HNMR (300 MHz, CDCl$_3$) δ 14.28 (s, 1H, —NH-1), 7.97 (s, 1H, —NH-1'), 7.59 (s, 1H, H-4'), 7.13 (dd, 1H, J=8.22 Hz, H-6'), 6.83 (d, 1H, J=8.23 Hz, H-7'), 6.15 (s, 1H, —CONH—), 3.94 (m, 1H, —CONHCH(H)—), 3.73 (m, 1H, —CONHCH(H)—), 3.35 (m, 1H, —CH(OH)—), 3.11 (t, 2H, —CH$_2$-4), 2.92 (t, 2H, —CH$_2$-6), 2.77 (bs, 2H, —CH$_2$N(CH$_2$CH$_2$)$_2$NCH$_3$), 2.60 (s, 3H, —CH$_3$-2), 2.52~2.40 (m, 8H, —N(CH$_2$CH$_2$)$_2$NCH$_3$), 2.33 (s, 3H, —N(CH$_2$CH$_2$)$_2$NCH$_3$), 2.08 (m, 2H, —CH$_2$-5);

ESI-MS: 498.0 [M+H]$^+$, 520.0 [M+Na]$^+$.

Example 102

Synthesis of N-[3-(cyclohexyl(methyl)amino)-2-hydroxypropyl]-2-methyl-7-[1,2-dihydro-5-methyl-2-oxo-3H-indol-(Z)-3-ylidene]-4,5,6,7-tetrahydro-1H-indole-3-carboxamide (I-79)

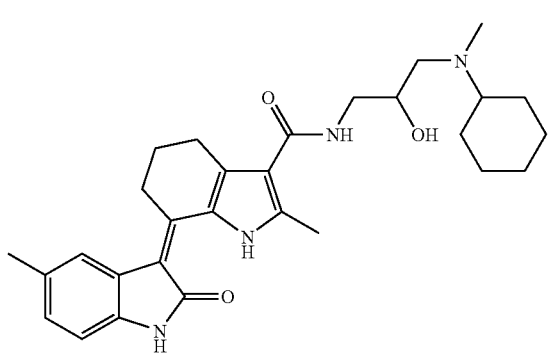

Similar procedure as Example 86, 5-methylindolin-2-one 0.13 g (0.88 mmol) and N-(3-(cyclohexyl(methyl)amino)-2-hydroxypropyl)-2-methyl-7-oxo-4,5,6,7-tetrahydro-1H-indole-3-carboxamide (II-18) 0.27 g (0.75 mmol) were reacted to give 0.14 g (38%) of the titled compound as a yellow solid.

$^1$HNMR (300 MHz, CDCl$_3$) δ 14.29 (s, 1H, —NH-1), 8.06 (s, 1H, —NH-1'), 7.42 (s, 1H, H-4'), 6.97 (d, 1H, J=7.88 Hz, H-6'), 6.80 (d, 1H, J=7.82 Hz, H-7'), 6.23 (t, 1H, —CONH—), 3.88 (m, 1H, —CONHCH(H)—), 3.74 (m, 1H, —CONHCH(H)—), 3.33 (m, 1H, —CH(OH)—), 3.12 (t, 2H, —CH$_2$-4), 2.89 (t, 2H, —CH$_2$-6), 2.59 (s, 3H, —CH$_3$-2), 2.52 (m, 2H, —CONHCH$_2$CH(OH)—CH$_2$N—), 2.38 (s, 3H, —NCH$_3$), 2.33 (s, 3H, —CH$_3$-5'), 2.05 (m, 2H, —CH$_2$-5), 1.88~1.62 (m, 6H, Cyclohexyl), 1.32~1.04 (m, 5H, Cyclohexyl);

ESI-MS: 491.1 [M+H]$^+$.

Example 103

Synthesis of N-(3-(diethylamino)-2-hydroxypropyl)-2-methyl-7-[1,2-dihydro-5-bromo-2-oxo-3H-indol-(Z)-3-ylidene]-4,5,6,7-tetrahydro-1H-indole-3-carboxamide (I-80)

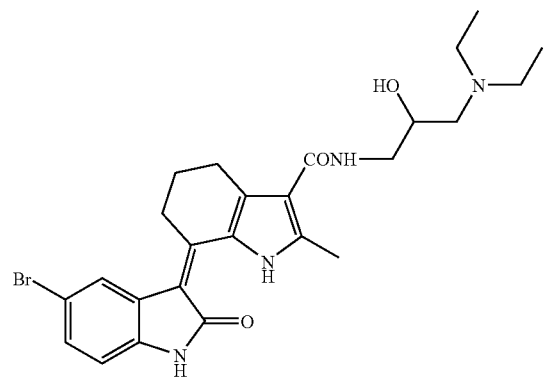

Similar procedure as Example 86, 5-bromoindolin-2-one 0.18 g (0.85 mmol) and N-(3-(diethylamino)-2-hydroxypropyl)-2-methyl-7-oxo-4,5,6,7-tetrahydro-1H-indole-3-carboxamide 0.25 g (0.78 mmol) were reacted to give 0.12 g (30%) of the titled compound as a yellow solid.

$^1$HNMR (300 MHz, CDCl$_3$) δ 14.22 (s, 1H, —NH-1), 8.33 (bs, 1H, —NH-1'), 7.70 (s, 1H, H-4'), 7.24 (1H, H-6'), 6.78 (d, 1H, J=8.2 Hz, H-7'), 6.28 (t, 1H, —CONH—), 3.86 (m, 1H, —CONHCH(H)—), 3.70 (m, 1H, —CONHCH(H)—), 3.34 (m, 1H, —CH(OH)—), 3.07 (t, 2H, —CH$_2$-4), 2.88 (t, 2H, —CH$_2$-6), 2.71 (m, 2H, —CH$_2$N(CH$_2$CH$_3$)$_2$), 2.58~2.37 (m, 7H, —CH$_3$-2, —CH$_2$N(CH$_2$CH$_3$)$_2$), 2.01 (m, 2H, —CH$_2$-5), 1.07 (t, 6H, —CH$_2$N(CH$_2$CH$_3$)$_2$);

ESI-MS: 516.2 [M+H]$^+$.

Example 104

Synthesis of N-(2-hydroxy-3-morpholinopropyl)-2-methyl-7-[1,2-dihydro-6-chloro-2-oxo-3H-indol-(Z)-3-ylidene]-4,5,6,7-tetrahydro-1H-indole-3-carboxamide (I-81)

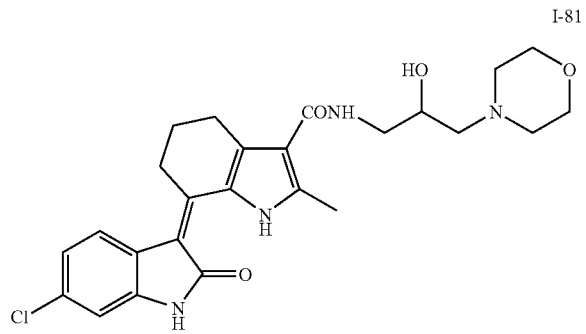

Similar procedure as Example 86, 6-chloroindolin-2-one 0.15 g (0.90 mmol) and N-(2-hydroxy-3-morpholinopropyl)-

2-methyl-7-oxo-4,5,6,7-tetrahydro-1H-indole-3-carboxamide (II-14) 0.25 g (0.75 mmol) were reacted to give 0.12 g (33%) of the titled compound as a yellow solid.

$^1$HNMR (300 MHz, CDCl$_3$) δ 14.20 (s, 1H, —NH-1), 7.69 (s, 1H, —NH-1'), 7.53 (d, 1H, J=8.7 Hz, H-4'), 7.02 (d, 1H, J=8.4 Hz, H-5'), 6.90 (s, 1H, H-7'), 6.08 (bs, 1H, —CONH—), 3.92 (s, 1H, —CONHCH(H)—), 3.72 (s, 6H, —OH, —CONHCH(H)—, —CH$_2$N(CH$_2$CH$_2$)$_2$O), 3.40 (m, 1H, —CH(OH)—), 3.11 (t, 2H, —CH$_2$-4), 2.95 (t, 2H, —CH$_2$-6), 2.67 (m, 2H, —CH$_2$N(CH$_2$CH$_2$)$_2$O), 2.61 (s, 3H, —CH$_3$-2), 2.44 (m, 4H, —CH$_2$N(CH$_2$CH$_2$)$_2$O), 2.08 (m, 2H, —CH$_2$-5);

ESI-MS: 485.2 [M+H]$^+$; 507.2 [M+Na]$^+$.

Example 105

Synthesis of N-[3-(cyclohexyl(methyl)amino)-2-hydroxypropyl]-2-methyl-7-[1,2-dihydro-5-fluoro-2-oxo-3H-indol-(Z)-3-ylidene]-4,5,6,7-tetrahydro-1H-indole-3-carboxamide (I-82)

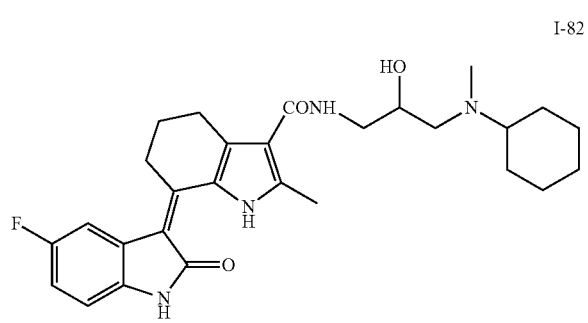

I-82

Similar procedure as Example 86, 5-fluoroindolin-2-one 0.15 g (1.0 mmol) and N-(3-(cyclohexyl(methyl)amino)-2-hydroxypropyl)-2-methyl-7-oxo-4,5,6,7-tetrahydro-1H-indole-3-carboxamide (II-18) 0.30 g (0.83 mmol) were reacted to give 0.12 g (29%) of the titled compound as a yellow solid.

$^1$HNMR (300 MHz, CDCl$_3$) δ 14.26 (s, 1H, —NH-1), 8.90 (bs, 1H, —NH-1'), 7.24 (dd, 1H, J=10.7 Hz, H-4'), 6.85 (m, 2H, H-6', H-7'), 6.22 (t, 1H, —CONH—), 3.79 (m, 1H, —CONHCH(H)—), 3.65 (m, 1H, —CONHCH(H)—), 3.22 (m, 1H, —CH(OH)—), 2.95 (t, 2H, —CH$_2$-4), 2.76 (t, 2H, —CH$_2$-6), 2.49 (s, 3H, —CH$_3$-2), 2.42 (m, 2H, —CH(OH)—CH$_2$N—), 2.22 (s, 3H, —NCH$_3$—), 1.94 (m, 2H, —CH$_2$-5), 1.77~1.53 (m, 6H, cyclohexyl), 1.23~1.00 (m, 5H, cyclohexyl);

ESI-MS: 495.3 [M+H]$^+$; 517.3 [M+Na]+.

Example 106

Synthesis of N-(2-hydroxy-3-morpholinopropyl)-2-methyl-7-[1,2-dihydro-5-bromo-2-oxo-3H-indol-(Z)-3-ylidene]-4,5,6,7-tetrahydro-1H-indole-3-carboxamide (I-83)

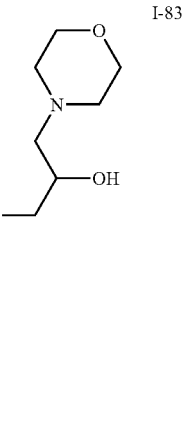

I-83

Similar procedure as Example 86, 5-bromoindolin-2-one 0.18 g (0.85 mmol) and N-(2-hydroxy-3-morpholinopropyl)-2-methyl-7-oxo-4,5,6,7-tetrahydro-1H-indole-3-carboxamide (II-14) 0.25 g (0.75 mmol) were reacted to give 0.10 g (25%) of the titled compound as a yellow solid.

$^1$HNMR (300 MHz, CDCl$_3$) δ 14.30 (s, 1H, —NH-1), 7.72 (s, 2H, —NH-1', H-4'), 7.26 (1H, H-6') 6.80 (d, 1H, J=8.22 Hz, H-7'), 6.24 (bs, 1H, —CONH—), 3.94 (s, 1H, —CONHCH(H)—), 3.69 (s, 6H, —OH, —CONHCH(H)—, —CH$_2$N(CH$_2$CH$_2$)$_2$O), 3.37 (m, 1H, —CH(OH)—), 3.13 (t, 2H, —CH$_2$-4), 2.94 (t, 2H, —CH$_2$-6), 2.69 (m, 2H, —CH$_2$N(CH$_2$CH$_2$)$_2$O), 2.61 (s, 3H, —CH$_3$-2), 2.46 (m, 4H, —CH$_2$N(CH$_2$CH$_2$)$_2$O), 2.06 (m, 2H, —CH$_2$-5);

ESI-MS: 530.2 [M+H]$^+$.

Biological Examples

The following assays are employed to find those compounds demonstrating the optimal degree of the desired activity.

1. Protein Kinase Activity by ELISA Assays In Vitro

The following assays may be used to determine the level of activity and effect of the different compounds of the present invention on one or more of the Pks. Similar assays can be designed along the same lines for any PK using techniques well knows in the art.

Enzyme linked immunosorbent assays (ELISA) may be used to detect and measure the presence of PK activity. The ELISA may be conducted according to known protocols which are described in, for example, Voller, et al., 1980, "Enzyme-Linkd Immunosorbent Assay," In: Manual of Clinical Immunology, 2nd., edited by Rose and Friedman, pp 359-371, Am. Soc. Of. Microbiology, Washington, D.C.

Tyrosine kinases such as VEGFR-2, PDGFR-β and c-Kit etc. catalyze the phosphorylation reaction of ATP and biotin-labeled peptide substrate, which will be ceased when the kinase activity is inhibited. According to the principle of ELISA, a monoclonal antibody can react with phosphorylated substrate specially, so biotin-labeled substrate is binded to streptavidin-coated ELISA plate, and then binded to a HRP-labeled goat anti-mouse antibody. Finally TMB is added for a color reaction and the value of A450-A630 is read by ELISA plate reader. The OD value can reflect the inhibitory activity of the VEGFR-2, PDGFR-β c-Kit tyrosine kinases treated with the test compounds at the different concentrations. So, the assay may be used to measure the inhibition ratio of the compounds for the tyrosine kinase activity. Similar assays can be designed along the same lines for any PK using techniques well known in the art.

1.1 Materials and Methods

VEGF Receptor 2, PDGF Receptor-beta and c-kit kinase assay kit (include kinase, 1.25M DTT, substrate peptide, 10 mM ATP, P-Tyr-100 Mouse antibody, 4×HTScan tyrosine kinase buffer), Cell Signaling Technology CO.; HRP labeled goat anti mouse IgG, Protein Tech CO.; TMB, Pierce CO.; Streptavidin Microtitration Plate, Greiner Bio-one CO.; Infinite M200 Reader, Tecan CO.

1.2 Method 1.2.1 Immediately transfer enzyme from −80° C. to ice. Allow enzyme to thaw on ice then at 4° C. and centrifugate transiently to the bottom of centrifuge tube, then lay back on ice quickly 1.2.2 Add 10 μl of DTT (1.25 M) to 2.5 ml of 4×HTScan tyrosine kinase buffer (240 mM HEPES pH 7.5, 20 mM MgCl2, 20 mM MnCl2, 12 μM $Na_3VO_4$). Transfer 0.6 ml of DTT/Kinase buffer to each enzyme tube to make 4× reaction Cocktail. Incubate 12.5 μl of the 4× reaction cocktail with 12.5 μl/well prediluted compound of interest for 5 minutes at room temperature, and set blank control, free-enzyme control, negative control and positive control.

1.2.3 Add 10 μl 10 mM ATP to 1.25 ml 6 μM substrate peptide. Dilute the mixture with dH20 to 2.5 ml to make 2×ATP/substrate cocktail. Add 25 μl of 2×ATP/substrate cocktail to 25 μl/well preincubated reaction cocktail/compound. Incubate reaction plate at room temperature for 30 minutes.

1.2.4 Add 50 μl/well stop Buffer (50 mM EDTA, pH 8) to stop the reaction. Transfer 25 μl of each reaction and 75 μl dH2O/well to a 96-well streptavidin coated plate and incubate at room temperature for 60 minutes. Wash three times with 200 μl/well PBS/T(1×PBS, 0.05% Tween-20).

1.2.5 Dilute primary antibody, Phospho-Tyrosine mAb (P-Tyr-100), 1:500 in PBS/T with 1% BSA. Add 100 μl/well primary antibody. Incubate at room temperature for 60 minutes. Wash three times with 200 μl/well PBS/T(1×PBS, 0.05% Tween-20).

1.2.6 Prepare appropriate dilution of HRP labeled secondary antibody, 1:500 in PBS/T with 1% BSA. Add 100 μl/well secondary antibody solution. Incubate at room temperature for 30 minutes. Wash five times with 200 μl/well PBS/T 1.2.7 Add 100 μl/well TMB substrate and incubate at room temperature for 1-10 minutes. Add 50 μl 2M $H_2SO_4$ to stop the color reaction. Read the absorbance of $A_{450}$-$A_{630}$ with the Infinite M200 microtiter plate reader.

1.2.8 Calculate the inhibition ratio with the following formula:

$$\text{Inhibition ratio (\%)} = \left(1 - \frac{OD \text{ of the compounds} - OD \text{ of no Enzyme}}{OD \text{ of negative} - OD \text{ of no Enzyme}}\right) \times 100\%$$

According to the inhibition ratio of enzyme activity at the different concentrations of the compound, activity inhibition ratio of 50% of the test compound is calculated through the logarithm of the concentration of the compound with the Logit [I] linear regressionl.

1.3 Result 1.3.1 Kinase Inhibition Ratio of Compounds

At the concentration of $10^{-7}$ mol/L, the kinase inhibition ratio of the compounds shows in Table 1.

TABLE 1

| Kinase | Comp. | | | | | | | | |
|---|---|---|---|---|---|---|---|---|---|
| | I-2 | I-3 | I-4 | I-5 | I-6 | I-7 | I-8 | I-63 | I-70 |
| VEGFR-2 | 75% | 54% | 76% | 74% | 79% | 82% | 76% | 80% | 84% |
| PDGFR-β | 90% | 88% | 86% | 87% | 85% | 86% | 89% | 87% | 85% |
| c-Kit | 46% | 43% | 60% | 67% | 77% | 74% | 77% | 73% | 76% |

1.3.2 $IC_{50}$ (nmol/L) of the VEGF Receptor Kinase $IC_{50}$ (umol/L) of some compounds of the present invention shows in Table 2.

TABLE 2

| | Comp. | | | | | | | | | | | | |
|---|---|---|---|---|---|---|---|---|---|---|---|---|---|
| | I-2 | I-3 | I-4 | I-5 | I-9 | I-14 | I-19 | I-21 | I-26 | I-34 | I-36 | I-40 | I-44 |
| $IC_{50}$ nmol/L | 76 | 5.3 | 5.6 | 9 | 30 | 79 | 31 | 27 | 9.1 | 11 | 6.3 | 82 | 6.8 |

| | Comp. | | | | | | | | | | | | |
|---|---|---|---|---|---|---|---|---|---|---|---|---|---|
| | I-45 | I-46 | I-49 | I-51 | I-53 | I-55 | I-56 | I-57 | I-60 | I-68 | I-71 | I-74 | I-77 |
| $IC_{50}$ nmol/L | 8.0 | 11 | 12 | 54 | 13 | 19 | 17 | 13 | 14 | 43 | 34 | 13 | 25 |

2. Tumor Cell Proliferation Assay (MTT Assay)

The assay used generally is the blue tetrazolium bromide (MTT) method. The yellow 3-(4,5-dimethylthiazolyl-2)-2,5-diphenyltetrazolium bromide (MTT) can be reduced to purple insoluble formazan by the succinodehydrogenase in the mitochondria of the active cells, but the dead cells do not have the same function. Intracellular purple formazan salt crystals can be solved in DMSO and the absorption value at 570 nm is detected by the microplate reader, then the number of living cells can be detected indirectly. So MTT assay may be used to determine the ability of a compound of the present invention to inhibit cell proliferation. Similar assays can be designed along the same lines for any cancer cell using techniques well known in the art.

2.1 Material and Equipment

RPMI 1640 medium (RPMI 1640+12% calf serum +HEPES 3.5 g/L+ NaHCO$_3$ 2.2 g/l+ penicillin 0.13 g/L+ streptomycin 0.15 g/L);

RPMI 1640 medium (RPMI 1640+12% fetal bovine serum +HEPES 3.5 g/L+ NaHCO$_3$ 2.2 g/l+ penicillin 0.13 g/L+ streptomycin 0.15 g/L);

DMEM/High glucose medium (DMEM+12% calf serum +HEPES 3.5 g/L+ NaHCO$_3$ 2.2 g/l+ penicillin 0.13 g/L+ streptomycin 0.15 g/L);

DMEM/High glucose medium (DMEM+12% fetal bovine serum +HEPES 3.5 g/L+ NaHCO$_3$ 2.2 g/l+ penicillin 0.13 g/L+ streptomycin 0.15 g/L);

MC COYS 5-A medium (MC COYS 5-A+12% fetal bovine serum +HEPES 3.5 g/L+ NaHCO$_3$ 2.2 g/l+ penicillin 0.13 g/L+ streptomycin 0.15 g/L);

Trypsin;

MTT (Amresco, Co., USA);

Microtiter plate reader (Tecan infinite M200)

2.2 Cancer Cell Lines 2.2.1 Human Gastric Cancer Cell Line (BGC)
2.2.2 Human Non-Small Cell Lung Cancer Cell Line (A549)
2.2.3 Human Leukemia Line (K562)
2.2.4 Human Pancreatic Carcinoma Cells (PANC-1)
2.2.5 Human Small Cell Lung Cancer Cell Line (NCI-H446)

The cells of the 2.2.1, 2.2.2, 2.2.3, 2.2.4, 2.2.5 cultured with RPMI 1640 containing 12% calf serum in the condition of 37° C., 5% CO$_2$.

2.2.6 Human Pancreatic Carcinoma Cell Line (BXPC-3);
2.2.7 Human Bladder Cancer Cell Line (T24);

The cells of 2.2.6, 2.2.7 cultured in RPMI 1640 medium containing 12% fetal bovine serum in the condition of 37° C., 5% CO$_2$.

2.2.8 Human Hepatocellular Carcinoma Cell Line (HEPG2);
2.2.9 Human Breast Cancer Cell Line (MCF-7);

The cells of 2.2.8, 2.2.9 cultured in DMEM/High glucose medium containing 12% calf serum in the condition of 37° C., 5% CO$_2$.

2.2.10 Human Colon Cancer Cell Line (CACO-2)

The cell of 2.2.10 cultured in DMEM/High glucose medium containing 12% fetal bovine serum in the condition of 37° C., 5% CO$_2$.

2.2.11 Human Colon Cancer Cell Line (HT-29);
2.2.12 Human Colon Cancer Cell Line (HCT 116);
2.2.13 Human Ovarian Cancer Cell Line (SK-OV-3).

The cells of 2.2.11, 2.2.12, 2.2.13 were cultured in MC COYS 5-A medium containing 12% fetal bovine serum in the condition of 37° C., 5% CO$_2$.

2.3 Methods 2.3.1 Cell seeding: Trypsinize the cell by 0.05% trypsin-EDTA and add RPMI 1640 medium (DMEM or 5A) containing 12% calf serum. Count the number, then dilute to 1.67×10$^4$/ml. Add 180 ul/well to the 96 well plate (3000 cells/well).

2.3.2 Culture: cells are incubated for 24 hours at 37° C. under 5% CO2.

2.3.3 Preliminary screening: The compounds are firstly diluted to 0.1 mol/L with DMSO, and then diluted to three concentrations of 10$^{-5}$ mol/L, 10$^{-6}$ mol/L and 10$^{-7}$ mol/L. Add 20 ul test compounds to the 96 well plate and incubate for 72 hours. Each group has three parallel wells and all experiments repeat three times. Each inhibition ratio is calculated, then an average value of three times is taken as the measured value.

2.3.4 Staining 2.3.4.1 Attached cell: add 20 ul/well MTT to the 96-well plates; incubate for 4 hours in the incubator. Pour out the culture medium in the well and add 100 ul/well DMSO. Shake the plate for 5 min.

2.3.4.2 Suspension cell: add 20 ul/well MTT to the 96-well plates; incubate for 4 hours in the incubator. Add 50 ul/well 20% SDS and incubate for overnight in the incubator.

2.3.5 Reading the plates: read the absorbance A570-A630 with the Infinite M200 microtiter plate reader. Calculate the inhibition ratio of the test compounds.

2.3.6 Secondary screening: the compounds whose inhibition ratio is greater than 50% at the concentrations of 10$^{-5}$ mol/L in the preliminary screening will be picked out for Secondary screening. Dilute these compounds to ten concentrations: 10$^{-5}$ mol/L, 0.5×10$^{-5}$ mol/L, 10$^{-6}$ mol/L, 0.8×10$^{-6}$ mol/L, 0.6×10$^{-6}$ mol/L, 0.4×10$^{-6}$ mol/L, 0.2×10$^{-6}$ mol/L, 10$^{-7}$ mol/L, 0.8×10$^{-7}$ mol/L and 0.4×10$^{-7}$ mol/L. Add 20 ul test compound solution to the 96 well plate and incubate for 48 hours. Each group has three parallel wells and all experiments repeat for three times. Read the plates and calculate the inhibition ratio according to the preliminary screening method.

2.3.7 Calculate the Inhibition Ratio of Cell Proliferation and the IC$_{50}$ $$\text{Inhibition ratio} = \frac{\left(\begin{array}{l}\text{average } OD \text{ value of the control group} - \\ \text{average } OD \text{ value of the compound group}\end{array}\right)}{\text{average } OD \text{ value of the control group}} \times 100\%$$

According to the inhibition ratio of cell proliferation at the different concentrations of the compound, inhibition ratio of 50% of the test compound is calculated through the logarithm of the concentration of the compound with the Logit [I] linear regression, and an average value of three times is taken as the measured value of a sample.

2.4 Result 2.4.1 Inhibition Ratio of Cell Proliferation

At the concentration of 10$^{-5}$ mol/L, inhibition ratio of some compounds of the present invention shows in table 3 and table 4.

TABLE 3

| | Cell Lines | | | | | | | | | | |
|---|---|---|---|---|---|---|---|---|---|---|---|
| | (Inhibition rate %) | | | | | | | | | | |
| Comp. | HEPG2 | A549 | BXPC-3 | BGC | T24 | HT29 | PANC-1 | HCT116 | CACO-2 | SK-OV-3 | NCI-H446 |
| I-2 | 64.0 | 10.2 | 79.4 | 71.0 | 81.4 | 97.4 | 70.6 | 99.4 | 43.0 | 92.2 | |
| I-3 | 98.2 | 55.5 | 96.0 | 78.1 | 98.1 | 65.1 | 69.8 | | | 86.7 | 69.9 |
| I-4 | | 67.5 | 78.4 | 70.1 | | 89.9 | | | | 57.1 | 57.7 |
| I-5 | 64.6 | 6.71 | 89.4 | 64.0 | 74.5 | 91.5 | 47.8 | 99.9 | 44.1 | 77.5 | |
| I-6 | | | 64.9 | 32.3 | | 61.9 | 19.8 | | | 32.2 | 27.1 |

TABLE 3-continued

| Comp. | HEPG2 | A549 | BXPC-3 | BGC | T24 | HT29 | PANC-1 | HCT116 | CACO-2 | SK-OV-3 | NCI-H446 |
|---|---|---|---|---|---|---|---|---|---|---|---|
| I-7 | | | 69.5 | 75.9 | | 78.4 | 51.8 | | | 63.3 | 62.7 |
| I-8 | 53.8 | 0.24 | 74.9 | 47.0 | 64.6 | 84.8 | 5.66 | 79.1 | 17.0 | 38.1 | |
| I-9 | 47.5 | 16.3 | 63.7 | 42.1 | 56.1 | 66.7 | 0 | 61.9 | 18.0 | | |
| I-10 | 43.5 | 7.64 | 51.7 | 15.2 | 27.5 | 30.9 | 11.7 | | 0 | | |
| I-11 | 2.92 | | | | 0 | | | | | | |
| I-12 | 12.8 | 1.10 | 29.5 | 31.9 | 14.6 | 78.4 | 23.3 | 36.5 | 11.7 | | |
| I-13 | 46.0 | 3.82 | 42.4 | 11.1 | 9.04 | 63.2 | 0 | | 9.79 | | |
| I-14 | 30.4 | 4.43 | 68.3 | 39.4 | 34.4 | 43.3 | 14.0 | 22.1 | 2.36 | | |
| I-15 | 61.1 | | | | 74.8 | | | | | | |
| I-63 | 100 | 61.8 | 97.3 | 80.8 | 99.0 | 92.7 | 92.1 | | | 94.0 | 79.0 |
| I-64 | | | 98.5 | 84.7 | | 96.6 | | | | 93.5 | 98.1 |
| I-65 | 100 | 85.0 | 99.2 | 91.1 | 97.9 | 98.3 | 98.1 | | | 95.7 | 99.0 |
| I-66 | | | 97.9 | 76.8 | | 93.0 | | | | 85.1 | 88.7 |
| I-67 | | | 51.7 | 67.6 | | 51.9 | | | | 8.34 | 49.3 |
| I-68 | | 61.1 | 60.7 | 55.4 | | 31.3 | 34.3 | | | 11.1 | 29.1 |
| I-69 | | 18.9 | 39.9 | 30.0 | | 34.9 | 22.4 | | | 2.80 | 25.3 |
| I-70 | | 76.3 | 98.7 | 84.8 | | 94.7 | 97.4 | | | 95.6 | 87.0 |
| I-71 | | 71.7 | 98.9 | 82.3 | | 95.0 | 97.4 | | | 91.7 | 87.5 |
| I-72 | | 81.2 | 99.3 | 85.9 | | 97.4 | 98.1 | | | 95.1 | 97.9 |
| I-73 | 59.3 | 2.54 | 90.2 | 48.8 | 88.4 | 95.6 | 48.0 | 98.7 | 44.4 | 71.9 | |
| I-74 | 84.9 | 1.27 | 32.1 | 60.2 | 98.7 | 92.2 | 93.6 | 99.9 | 83.1 | 88.2 | |
| I-75 | 99.0 | 40.1 | 73.1 | 45.4 | 99.9 | 67.3 | 53.6 | | | 49.2 | 44.1 |
| I-76 | | 64.5 | 97.5 | 74.2 | | 92.1 | 80.1 | | | 90.3 | 64.6 |
| I-77 | | 50.8 | 45.9 | 84.2 | | 74.4 | 61.9 | | | 77.3 | 57.2 |
| I-78 | | 29.9 | 31.7 | 48.5 | | 24.2 | 21.8 | | | 20.2 | 8.07 |
| I-79 | | 63.3 | 99.0 | 81.0 | | 98.2 | 96.8 | | | 96.0 | |

TABLE 4

| Comp. | K562 | MCF-7 |
|---|---|---|
| I-1 | 28.6 | |
| I-2 | 95.3 | 55.4 |
| I-5 | 93.3 | 50.5 |
| I-8 | 39.4 | 25.2 |
| I-73 | 94.8 | 43.4 |
| I-74 | 95.1 | 70.7 |

2.4.2 IC$_{50}$ of Cell Proliferation (μmol/L)

IC$_{50}$ (μmol/L) of some compounds of the present invention shows in table 5 and table 6:

TABLE 5

| Comp. | BXPC-3 | T24 | BGC | HEPG2 | HT29 | A549 | NCI-H446 | PANC-1 | SK-OV-3 |
|---|---|---|---|---|---|---|---|---|---|
| I-2 | 0.52 | 3.31 | 6.11 | 7.27 | 1.2 | | | | |
| I-3 | 1.95 | 1.83 | 2.03 | 3.14 | 6.48 | 4.95 | 6.47 | 1.94 | 2.99 |
| I-4 | 2.43 | | 3.15 | | 1.73 | 1.01 | 5.17 | | 5.27 |
| I-5 | 0.52 | 3.56 | 6.73 | 7.73 | 0.54 | | | | |
| I-6 | 5.99 | | | | 4.38 | | | | |
| I-7 | 3.43 | | 2.76 | | 3.06 | | 5.99 | 6.63 | 3.04 |
| I-8 | 1.17 | | | | | | | | |
| I-63 | 1.16 | 3.04 | 1.85 | 3.15 | 1.02 | 2.01 | 2.27 | 0.66 | 1.35 |
| I-64 | 1.29 | | 2.21 | 1.3 | | 2.05 | | | 2.24 |
| I-65 | 1.15 | 2.73 | 1.72 | 2.8 | 3.06 | 2.38 | 1.5 | 1.67 | 2.23 |
| I-66 | 3.19 | | 4.66 | | 2.89 | | 3.03 | | 3.17 |
| I-67 | 7.68 | | 4.26 | | 6.9 | | 9.42 | | |
| I-68 | 6.49 | | 7.59 | | | 5.49 | | | |
| I-70 | 0.97 | | 1.49 | | 0.93 | 1.03 | 2.64 | 1.63 | 1.14 |
| I-71 | 2.73 | | 1.42 | | 0.79 | 2.35 | 2.52 | 1.48 | 1.54 |
| I-72 | 1.89 | | 2.92 | | 4.36 | 3.73 | 2.98 | 1.81 | 2.17 |
| I-73 | 1.24 | 5.9 | 10.22 | 7.36 | 0.64 | | | | |
| I-74 | 0.24 | 2.64 | 7.95 | 7.22 | 0.42 | | | | |
| I-75 | 4.47 | 3.99 | 11.1 | 3.59 | 5.17 | 14.52 | 9.25 | 3.58 | 5.69 |
| I-76 | 2.24 | | 3.63 | | 1.38 | 1.36 | 7.09 | 3.4 | 3.03 |

TABLE 5-continued

| | Cell Lines | | | | | | | | |
|---|---|---|---|---|---|---|---|---|---|
| | IC$_{50}$ (umol/L) | | | | | | | | |
| Comp. | BXPC-3 | T24 | BGC | HEPG2 | HT29 | A549 | NCI-H446 | PANC-1 | SK-OV-3 |
| I-77 | 8.7 | | 3.45 | | 8.38 | 7.12 | 8.15 | 5.53 | 6.4 |
| I-78 | | | 12.15 | | | | | | |
| I-79 | 0.84 | | 2.28 | | 2.32 | 2.84 | 3.26 | 3.99 | 1.51 |

TABLE 6

| | Cell Lines | |
|---|---|---|
| | IC$_{50}$ (umol/L) | |
| Comp. | K562 | MCF-7 |
| I-2 | 3.51 | 7.88 |
| I-5 | 2.94 | 6.94 |
| I-73 | 0.72 | |
| I-74 | 0.93 | 7.01 |

3. Conclusion

The compounds of the present invention which has the chemical structure of Formula (I) show very good inhibitory activity against many kinases, and the IC$_{50}$ of VEGFR-2 kinase is generally below $10^{-7}$ mol/L. The compound of Formula (I) may be used as a pharmaceutical composition for treating a protein kinase related disorder in an organism. Further more, the compounds of Formula (I) can inhibit proliferation of many tumor cells, wherein most compounds significantly inhibit tumor cell proliferation with IC$_{50}$ below $10^{-5}$ mol/L. The compounds of Formula (I) in the present invention also can be applied to the preparation of anti-tumor agents.

What is claimed is:

1. A compound of Formula (I) or a pharmaceutically acceptable salt thereof:

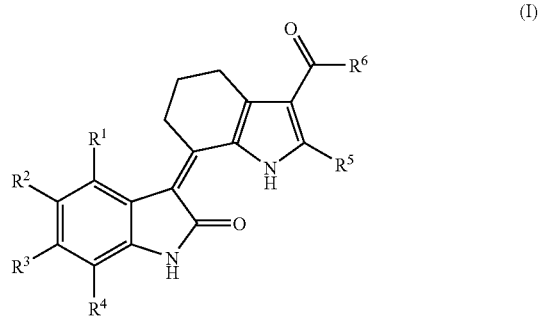

(I)

wherein:
R$^1$ is selected from the group consisting of hydrogen, halo, alkyl, cycloalkyl, aryl, heteroaryl, heteroalicyclic, hydroxy, alkoxy, —C(O)R$^7$, —NR$^8$R$^9$, —(CH$_2$)$_n$R$^{10}$ and —C(O)NR$^{11}$R$^{12}$;
R$^2$ is selected from the group consisting of hydrogen, halo, alkyl, haloalkyl, hydroxy, alkoxy, haloalkoxy, nitro, cyano, —NR$^8$R$^9$, —NR$^8$C(O)R$^9$, —C(O)R$^7$, aryl, heteroaryl, —C(O)NR$^{11}$R$^{12}$, S(O)$_2$NR$^8$R$^9$ and —SO$_2$R$^{13}$;
R$^3$ is selected from the group consisting of hydrogen, halo, alkyl, haloalkyl, hydroxy, alkoxy, —C(O)R$^7$, —NR$^8$R$^9$, aryl, heteroaryl, —NR$^8$S(O)$_2$R$^9$, —S(O)$_2$NR$^8$R$^9$, —NR$^8$C(O)R$^9$, —NR$^8$C(O)OR$^9$ and —SO$_2$R$^{13}$;
R$^4$ is selected from the group consisting of hydrogen, halo, alkyl, hydroxy, alkoxy and —NR$^8$R$^9$;
R$^5$ is selected from the group consisting of hydrogen, alkyl and —C(O)R$^{14}$;
R$^6$ is selected from the group consisting of hydroxy, alkoxy, aryloxy, —N(R$^{15}$)(CH$_2$)$_r$R$^{16}$, —NR$^8$R$^9$ and —N(R$^{17}$)—CH(R$^{18}$)—CR$^{19}$(OH)—CH(R$^{20}$)Z;
R$^7$ is selected from the group consisting of hydrogen, hydroxy, alkoxy and aryloxy;
R$^8$ and R$^9$ are each independently selected from the group consisting of hydrogen, alkyl, cycloalkyl, aryl and heteroaryl;
or R$^8$ and R$^9$ together with the atoms to which they are attached may form a heteroalicyclic ring;
R$^{10}$ is selected from the group consisting of hydroxy, —C(O)R$^7$, —NR$^8$R$^9$ and —C(O)NR$^8$R$^9$;
R$^{11}$ and R$^{12}$ are each independently selected from the group consisting of hydrogen, alkyl and aryl;
or R$^{11}$ and R$^{12}$ together with the nitrogen atom to which they are attached may form a heteroalicyclic ring;
R$^{13}$ is selected from the group consisting of alkyl, aryl, arylalkyl, heteroaryl and heteroarylalkyl;
R$^{14}$ is selected from the group consisting of hydroxy, alkoxy, aryloxy and —NR$^8$R$^9$;
R$^{15}$ is selected from the group consisting of hydrogen and alkyl;
R$^{16}$ is selected from the group consisting of hydroxy, —NR$^8$R$^9$, —C(O)R$^7$, aryl, heteroaryl, —N$^+$(O$^-$) R$^8$R$^9$, —N(OH) R$^8$ and —NHC(O)R$^a$, wherein R$^a$ is selected from the group consisting of unsubstituted alkyl, haloalkyl and arylalkyl;
R$^{17}$, R$^{18}$, R$^{19}$ and R$^{20}$ are each independently selected from the group consisting of hydrogen and alkyl;
Z is selected from the group consisting of aryl, heteroaryl and —NR$^8$R$^9$;
n and r are each independently an integer from 1 to 4.

2. The compound or a pharmaceutically acceptable salt of claim 1, wherein:
R$^1$ is selected from the group consisting of hydrogen, halo, alkyl, cycloalkyl, aryl, heteroaryl, heteroalicyclic, hydroxy, alkoxy, —C(O)R$^7$, —NR$^8$R$^9$, —(CH$_2$)$_n$R$^{10}$ and —C(O)NR$^{11}$R$^{12}$;
R$^2$ is selected from the group consisting of hydrogen, halo, alkyl, trihalomethyl, hydroxy, alkoxy, trihalomethoxy, nitro, cyano, —NR$^8$R$^9$, —NR$^8$C(O)R$^9$, —C(O)R$^7$, aryl, heteroaryl, —C(O)NR$^{11}$R$^{12}$, —S(O)$_2$NR$^8$R$^9$ and —SO$_2$R$^{13}$;
R$^3$ is selected from the group consisting of hydrogen, halo, alkyl, trihalomethyl, hydroxy, alkoxy, —C(O)R$^7$, —NR$^8$R$^9$, aryl, heteroaryl, —NR$^8$S(O)$_2$R$^9$, —S(O)$_2$NR$^8$R$^9$, —NR$^8$C(O)R$^9$, —NR$^8$C(O)OR$^9$ and —SO$_2$R$^{13}$;
R$^4$ is selected from the group consisting of hydrogen, halo, alkyl, hydroxy, alkoxy and —NR$^8$R$^9$;

$R^5$ is selected from the group consisting of hydrogen, alkyl and —C(O)R$^{14}$;

$R^6$ is selected from the group consisting of hydroxy, alkoxy, —NR$^8$R$^9$, —N(R$^{15}$)(CH$_2$)$_r$R$^{16}$ and —NHCH(R$^{18}$)—CR$^{19}$(OH)—CH(R$^{20}$)Z;

$R^7$ is selected from the group consisting of hydrogen, hydroxy, alkoxy and aryloxy;

$R^8$ and $R^9$ are each independently selected from the group consisting of hydrogen, alkyl, cycloalkyl, aryl and heteroaryl;

or $R^8$ and $R^9$ together with the atoms to which they are attached may form a heteroalicyclic ring;

$R^{10}$ is selected from the group consisting of hydroxy, —C(O)R$^7$, —NR$^8$R$^9$ and —C(O)NR$^8$R$^9$;

$R^{11}$ and $R^{12}$ are each independently selected from the group consisting of hydrogen, alkyl and aryl;

or $R^{11}$ and $R^{12}$ together with the nitrogen atom to which they are attached may form a heteroalicyclic ring;

$R^{13}$ is selected from the group consisting of alkyl, aryl, arylalkyl, heteroaryl and heteroarylalkyl;

$R^{14}$ is selected from the group consisting of hydroxy, alkoxy, aryloxy and —NR$^8$R$^9$;

$R^{15}$ is selected from the group consisting of hydrogen and alkyl;

$R^{16}$ is selected from the group consisting of hydroxy, aryl, heteroaryl and —NR$^8$R$^9$; R$^{18}$, R$^{19}$ and R$^{20}$ are each independently selected from the group consisting of hydrogen and alkyl;

Z is selected from the group consisting of aryl, heteroaryl and —NR$^8$R$^9$;

n is an integer from 1 to 4;

r is an integer from 1 to 3.

3. The compound or a pharmaceutically acceptable salt of claim 1, wherein:

$R^1$, $R^3$ and $R^4$ are each independently selected from the group consisting of hydrogen, halo and alkyl;

$R^2$ is selected from the group consisting of hydrogen, halo, alkyl, alkoxy, trihalomethoxy, nitro, —NR$^8$C(O)R$^9$, —C(O)R$^7$, —S(O)$_2$NR$^8$R$^9$ and —C(O)NR$^{11}$R$^{12}$;

$R^5$ is methyl;

$R^6$ is selected from the group consisting of hydroxy, alkoxy, —NR$^8$R$^9$, —N(R$^{15}$)(CH$_2$)$_r$R$^{16}$ and —NHCH$_2$CH(OH)CH$_2$—NR$^8$R$^9$;

$R^7$ is selected from the group consisting of hydroxy, alkoxy and aryloxy;

$R^8$ and $R^9$ are each independently selected from the group consisting of hydrogen, alkyl, cycloalkyl, aryl and heteroaryl;

or $R^8$ and $R^9$ together with the atoms to which they are attached may form a heteroalicyclic ring;

$R^{11}$ and $R^{12}$ are each independently selected from the group consisting of hydrogen, alkyl and aryl;

or $R^{11}$ and $R^{12}$ together with the nitrogen atom to which they are attached may form a heteroalicyclic ring;

$R^{15}$ is selected from the group consisting of hydrogen and alkyl;

$R^{16}$ is selected from the group consisting of hydroxy, aryl, heteroaryl and —NR$^8$R$^9$;

r is an integer from 1 to 3.

4. A method for preparing the compound of Formula (I) comprising following steps of:

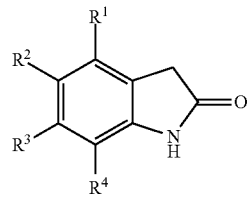

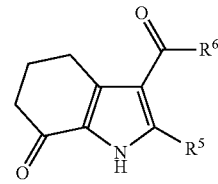

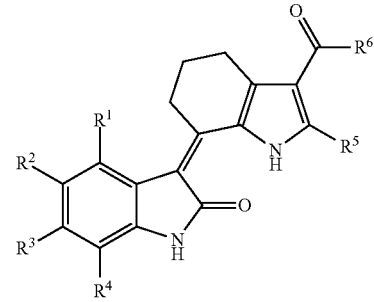

definitions of $R^1$, $R^2$, $R^3$, $R^4$, $R^5$ and $R^6$ are as described in claim 1 under lewis acid condition, the compound of Formula (III) and the compound of Formula (II) react in a non-proton solvent for 1 to 20 hours, with a reaction temperature from 50° C. to 150° C. to get the compound of Formula (I).

5. The method of claim 4, wherein the lewis acid is selected from a group consisting of AlCl$_3$, BF$_3$, SnCl$_2$, ZnCl$_2$ and TiCl$_4$.

6. The method of claim 4, wherein the non-proton solvent is non-proton protophilic solvent or inert solvent;

the non-proton protophilic solvent is selected from a group consisting of N,N-dimethylformamide, acetone, acetonitrile, dimethyl sulfoxide and pyridine; and the inert solvent is selected from a group consisting of pentane, hexane, cyclonexane, benzene and toluene.

7. The method of claim 4, wherein the non-proton solvent is selected from a group consisting of amides, ketones, nitriles, DMSO and pyridine.

8. The method of claim 4, wherein the reaction temperature is from 100° C. to 110° C. and reaction time is 8 to 10 hours.

9. A method to inhibit kinases of VEGFR-2, PDGFR-β and c-Kit and tumor cell proliferation comprising administering a pharmaceutical composition comprising a compound or salt of any one of claims 1, 2 or 3.

10. The method of claim 9, wherein said kinases and tumor cells belong to a mammal or a human.

11. A pharmaceutical composition for inhibiting kinases of VEGFR-2, PDGFR-β AND C-Kit and tumor cell proliferation, comprising a compound or pharmaceutically acceptable salt of any one of claims 1, 2 or 3 and a pharmaceutically acceptable carrier or excipient.

* * * * *